United States Patent
Yang et al.

(10) Patent No.: US 11,851,454 B2
(45) Date of Patent: *Dec. 26, 2023

(54) COMPOSITIONS AND METHODS FOR LIQUID PHASE OLIGONUCLEOTIDE SYNTHESIS

(71) Applicant: Hongene Biotech Corporation, Union City, CA (US)

(72) Inventors: Gaomai Yang, Davis, CA (US); Yun-Chiao Yao, Fremont, CA (US); David Yu, Union City, CA (US); Aldrich N. K. Lau, Palo Alto, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/146,279

(22) Filed: Dec. 23, 2022

(65) Prior Publication Data

US 2023/0212209 A1 Jul. 6, 2023

Related U.S. Application Data

(60) Provisional application No. 63/295,415, filed on Dec. 30, 2021.

(51) Int. Cl.
| | |
|---|---|
| *C07H 1/00* | (2006.01) |
| *C07H 21/00* | (2006.01) |
| *C08F 220/56* | (2006.01) |
| *C08F 265/10* | (2006.01) |
| *C08F 220/28* | (2006.01) |
| *C08F 120/68* | (2006.01) |

(52) U.S. Cl.
CPC ............. *C07H 1/00* (2013.01); *C07H 21/00* (2013.01); *C08F 120/68* (2013.01); *C08F 220/286* (2020.02); *C08F 220/56* (2013.01); *C08F 265/10* (2013.01)

(58) Field of Classification Search
CPC .. C08F 220/56; C08F 265/10; C08F 220/286; C08F 120/68; C07H 1/00; C07H 21/00; C07H 21/02; C07H 19/10; C07H 19/067; C07H 19/14
See application file for complete search history.

(56) References Cited

U.S. PATENT DOCUMENTS

| | | |
|---|---|---|
| 5,798,210 A | 8/1998 | Canard et al. |
| 6,677,120 B2 | 1/2004 | Shanghvi et al. |
| 7,276,599 B2 | 10/2007 | Moore et al. |
| 8,143,369 B2 | 3/2012 | Fujiwara et al. |
| 8,450,504 B2 | 5/2013 | Hedrick et al. |
| 8,664,357 B2 | 3/2014 | Livingston |
| 10,544,456 B2 | 1/2020 | Esfandyarpour et al. |
| 2013/0231260 A1 | 9/2013 | Lau et al. |
| 2014/0287945 A1 | 9/2014 | Lau et al. |
| 2018/0023122 A1 | 1/2018 | Crameri et al. |
| 2018/0100190 A1 | 4/2018 | Esfandyarpour et al. |

FOREIGN PATENT DOCUMENTS

| | | |
|---|---|---|
| EP | 0 850 949 | 7/1998 |
| EP | 1 710 249 | 1/2005 |
| FR | 2623510 | 5/1989 |
| WO | WO 02/079215 | 10/2002 |
| WO | WO 03/093346 | 11/2003 |
| WO | WO 05/123139 | 12/2005 |
| WO | WO 16/160475 | 10/2016 |

OTHER PUBLICATIONS

Bonora et al., Nucleic Acids Research 1993, 21(5) pp. 1213-1217 (Year: 1993).*
Gravert et al., Chem. Rev. 1997 97, pp. 489-509 (Year: 1997).*
Wang et al., Progress in Polymer Science, 2016, 53, pp. 169-206 (Year: 2016).*
Atdbio, 2021, Solid State Oligonucleotide Synthesis, https://www.atdbio.com/content/17/Solid-phase-oligonucleotide-synthesis, 26 pp.
Beaucage et al., 1992, Advances in the synthesis of oligonucleotides by the phosphoramidite approach, Tetrahedron, 48(12):2223-2311.
Bonora et al., 1993, Large scale, liquid phase synthesis of oligonucleotides by the phosphoramidite approach, Nucleic Acids Research, 21(5):1213-1217.
Carey, 1992, Organic Chemistry, 2d ed., McGraw-Hill, Inc., New York, pp. 328-331.
Creusen et al., 2020, Scalable one-pot—liquid-phase oligonucleotide synthesis for model network hydrogels, ChemRxiv., preprint. https://doi.org/10.26434/chemrxiv.12327569.v1.
Gorelov et al., 1979, Thermal decomposition of poly(phenyl- and poly(pentafluorophenyl acrylates)), Vysokomolekularnye Soedineniya, Seriya B: Bratkie Soobshcheniya, 21(6):410-413 (abstract).
Gravert et al., 1997, Organic synthesis on soluble polymer supports: liquid-phase methodologies, Chem. Rev., 97:489-409.
Greene et al., 1999, Protective Groups in Organic Synthesis, 3rd Ed., John Wiley & Sons, New York (TOC).
Katayama et al., 2018, Liquid-phase synthesis of oligonucleotides, in Synthesis of Therapeutic Oligonucleotides, Obika et al., eds., Springer Nature Singapore Pte Ltd., pp. 83-95.
Kim et al., 2013, Liquid-phase RNA synthesis by using alkyl-chain-soluble support, Chem. Eur. J., 19:8615-8620.
Livingston, Jan. 2, 2020, Liquid phase oligonucleotide synthesis, Oxford Global, Biologics Series, 2 pp.
McMurry, 2000, Organic Chemistry, 5th ed., Brooks/Cole, Pacific Grove, CA, pp. 398 and 408.

(Continued)

*Primary Examiner* — Robert D Harlan
(74) *Attorney, Agent, or Firm* — Knobbe, Martens, Olson & Bear, LLP

(57) ABSTRACT

Embodiments of the present application relate to polymers used as polymeric polyvalent hub for liquid phase oligonucleotide synthesis. Methods for making an oligonucleotide by liquid phase oligonucleotide synthesis using the polyvalent hub are also provided.

28 Claims, 18 Drawing Sheets

(56) References Cited

OTHER PUBLICATIONS

McOmie, ed., 1973, Protective Groups in Organic Chemistry, Plenum Press (TOC).

Merrifield, Jul. 20, 1963, Solid phase peptide synthesis. I. The synthesis of a tetrapeptide, J. Am. Chem. Soc., 85(14):2149-2154.

Merrifield, Oct. 8, 1965, Automated synthesis of peptides: solid-phase peptide synthesis, a simple and rapid synthetic method, has now been automates, Science, 150(3693):178-185.

Molina et al., 2019, Liquid-phase oligonucleotide synthesis: past, present, and future predictions, Current Protocols in Nucleic Acid Chemistry, 77:e82, 17 pp.

Scheit, 1980, Nucleotide analogs: Synthesis and biological function. New York: John Wiley & Sons (TOC).

Streitwieser et al., 1981, Introduction to Organic Chemistry, 2d ed., Macmillan Publishing Co., Inc., New York, pp. 169-171.

Takahashi et al., 2012, Development of an efficient liquid-phase peptide synthesis protocol using a novel fluorene-derived anchor support compound with Fmoc chemistry; AJIPHASE®, Tetrahedron Lett., 53:1936-1939.

Takahashi et al., 2012, Novel diphenylmethyl-derived amide protecting group for efficient liquid-phase peptide synthesis: AJIPHASE, Organic Lett., 14:4514-4517.

Takahashi et al., 2017, AJIPHASE®: a highly efficient synthetic method for one-pot peptide elongation in the solution phase by an Fmoc strategy, Angew. Chem. Int. Ed., 56:7803-7807.

Uhlman et al., Jun. 1990, Antisense oligonucleotides: a new therapeutic principle, Chemical Reviews, 90(4):543-584.

Wang et al., 2016, Recent advances in regenerated cellulose materials, Progress in Polymer Science, 53:169-206.

\* cited by examiner

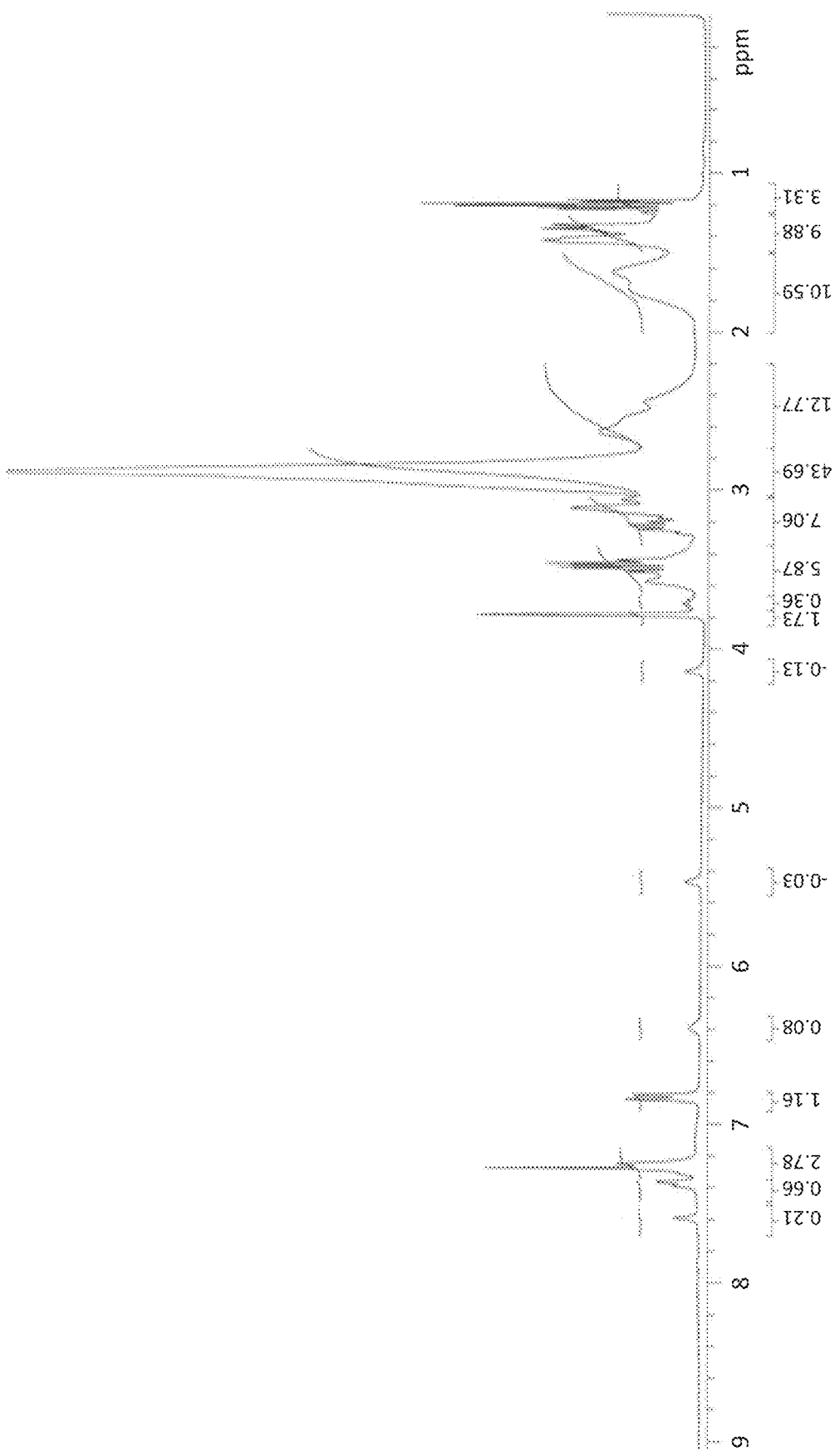

¹H-NMR of poly(NH₂-PEG-co-DMA) copolymer having 5 mol% of amino-PEG pendants with two dT conjugates, comprising a 5'-DMT protective group on the second dT.

COMPOSITIONS AND METHODS FOR LIQUID PHASE OLIGONUCLEOTIDE SYNTHESIS

BACKGROUND

Field

The present application relates to methods and compositions for liquid phase oligonucleotide synthesis employing the use of a polyvalent polymer hub.

Description of the Related Art

Oligonucleotide-based drugs have become a powerful epitome having ability to treat various diseases. Currently, the demand for oligonucleotides can be fulfilled by conventional solid phase oligonucleotide synthesis. There are certain advantages of Solid Phase Oligo Synthesis (SPOS), such as simple product isolation and the use of anhydrous synthetic environment. However, the SPOS generally has low over all yield after multiple steps for an oligo sequence and high cost for reagents, solid support and waste management. In addition, SPOS may result in mismatched oligo sequences which leads to difficulty in purification. The increasing demand for metric ton quantities of oligonucleotides far exceeds the production capacity of solid phase oligonucleotide synthesis.

Liquid phase oligonucleotide synthesis (LPOS) is a technology with the potential to provide the production capacity that will be required. One of the major advantages of LPOS over SPOS is the absence of the heterogeneous nature of the process, i.e., insoluble solid supports are not present. The use of a soluble scaffold or support employed in LPOS allows each step of the synthesis to be performed in the liquid phase.

The recent advances in the LPOS have been reported by Molina et al., *Current Protocol in Nucleic Acid Chemistry* (2019) 77, e82. The current LPOS technologies have an unfavorable E factor and additional efforts are required to address the usage of excessive reagents and solvents. In addition, one of the current challenges of LPOS is the difficulties associated in isolating and purifying the oligonucleotide products. For example, the nanofiltration technologies currently employed for isolation and purification are not economically favorable. There exists a need for improved materials and methods for conducting liquid phase oligonucleotide synthesis, for example, the need to expand the current repertoire of soluble supports with increased solubility and lower costs, while allowing for efficient removal of excess reagents and protecting groups after each LPOS cycle using a minimum amount of solvent.

SUMMARY

Some aspect of the present disclosure relates to a polymer for liquid phase oligonucleotide synthesis, comprising one or more repeating units of Formula (I):

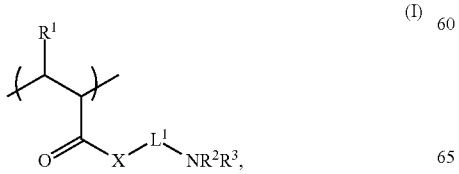

(I)

wherein:
X is $NR^4$, S, or O;
each of $R^1$, $R^2$, $R^3$ and $R^4$ is independently H or $C_1$-$C_6$ alkyl; and
$L^1$ is a heteroalkylene linker comprising one or more oxygen atoms.

In some embodiments, $R^1$ is H. In certain embodiments, the repeating unit of Formula (I) is also represented by Formula (Ia):

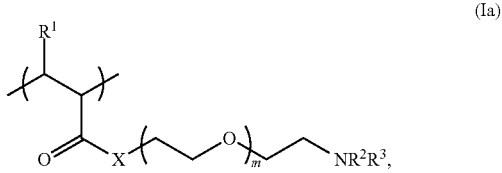

(Ia)

wherein m is an integer of 1 to 1000. In other embodiments, the repeating unit of Formula (I) is also represented by Formula (Ib):

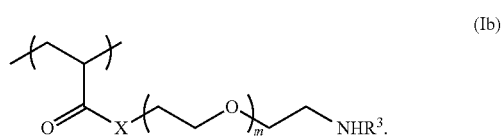

(Ib)

In some embodiments, X is NH and m is 2. In other embodiments, X is O, and m is from about 10 to 200.

In some embodiments, the polymer comprises one or more acrylamide or acrylate repeating unit of Formula (II):

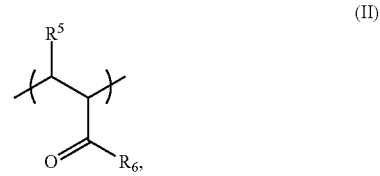

(II)

wherein
$R^5$ is H or $C_1$-$C_6$ alkyl;
$R^6$ is $-NR^7R^8$ or $-O-L^2-R^9$;
each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and
$L^2$ is a heteroalkylene linker comprising one or more oxygen atoms.

In some embodiments, $R^5$ is H. In certain embodiments, $R^6$ is $-NR^7R^8$, and the repeating unit of Formula (II) is also represented by Formula (IIa):

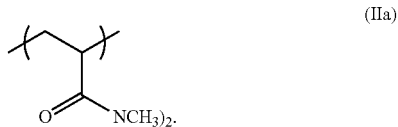

(IIa)

In other embodiments, $R^6$ is —O-$L^2$-$R^9$, and the repeating unit of Formula (II) is also represented by Formula (IIb):

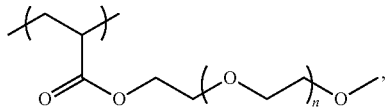
(IIb)

wherein n is an integer of 1 to 1000.

In some embodiments, the polymer comprises or has the structure:

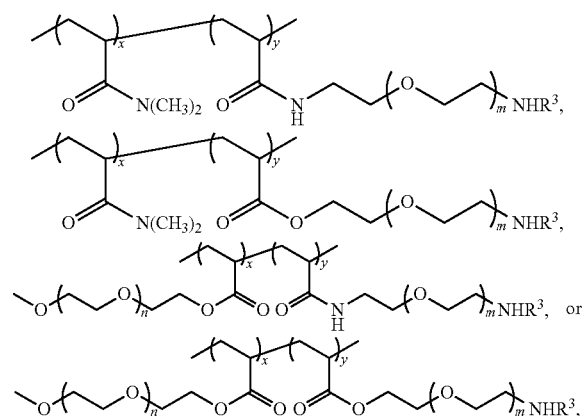

wherein each of m and n is independently an integer from about 2 to 200; and each of x and y is independently an integer from 1 to 50,000.

Some aspect of the present disclosure relates to a method for preparing oligonucleotides by liquid phase oligonucleotide synthesis, comprising:
  dissolving a polyvalent hub (PVH) comprising the polymer as described herein in a first solvent to form a reaction matrix; and
  reacting the PVH with one or more nucleoside analogs to form a first bioconjugate comprising a structure of Formula (III):

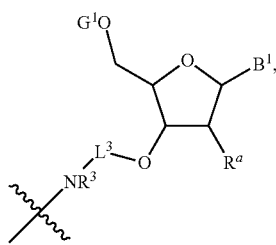
(III)

wherein
  $B^1$ is a nitrogenous base;
  $G^1$ is a 5' hydroxyl blocking group;
  $R^a$ is —H, —OH, halogen, —O—($C_1$-$C_6$ alkyl), —O—($C_1$-$C_6$ haloalkyl), or —OY, where Y is a 2' hydroxyl protecting group; and
  $L^3$ is a cleavable heteroalkylene linker where one or more carbon atoms is replaced by O, S, N, C(=O) or C(=S).

In some embodiments of the method described herein, the structure of Formula (III) is also represented by Formula (IIIa):

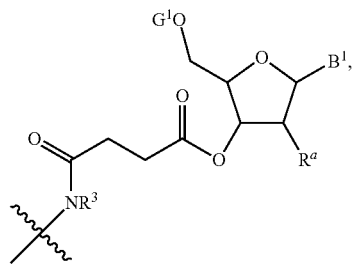
(IIIa)

In some embodiments of the method, $B^1$ is independently optionally protected adenine, optionally protected deaza adenine, optionally protected cytosine, optionally protected guanine, optionally protected deaza guanine, optionally protected thymine or optionally protected uracil. In further embodiments, $B^1$ is

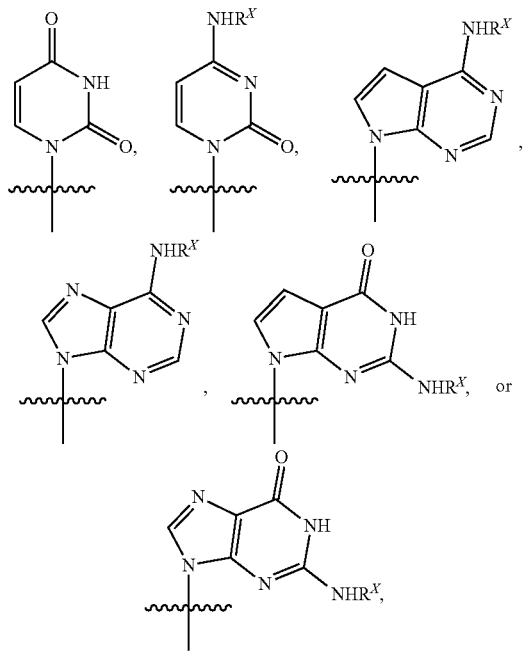

wherein $R^x$ is hydrogen, unsubstituted or substituted $C_1$-$C_6$ alkyl, or an amino protecting group, or the hydrogen in —NH$R^x$ is absent and $R^x$ is a divalent amino protecting group.

In some embodiments of the method, $G^1$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In one embodiment, $G^1$ is bis(4-methoxyphenyl)phenylmethyl (DMT).

In some embodiments, the method further comprises: removing the 5' hydroxyl blocking group ($G^1$) to form a 5' unblocked first bioconjugate; and isolating the 5' unblocked first bioconjugate. In some embodiments, isolation or purification of the 5' unblocked first bioconjugate is achieved by precipitation, dialysis, filtration, or ultrafiltration. In some further embodiments, the isolation/purification is achieved by using a membrane comprising a regenerated cellulose. In some embodiments, the regenerated cellulose has a molecular weight cutoff (MWCO) from about 5 kDa to about 50 kDa. In some embodiments, the regenerated cellulose is negatively charged.

In some embodiments, the method further comprises:
(a) reacting the 5' unblocked first bioconjugate with one or more nucleoside phosphoramidite analogs in a second solvent to form a second bioconjugate comprising the structure of Formula (IV):

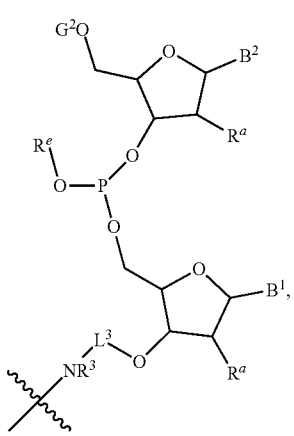

(IV)

wherein
$G^2$ is a 5' hydroxyl blocking group;
$B^2$ is a nitrogenous base; and
$R^e$ is a phosphite protecting group;
(b) oxidizing the phosphite moiety in Formula (IV);
(c) removing the 5' blocking group $G^2$ to form a 5' unblocked second bioconjugate comprising the structure of Formula (IV'):

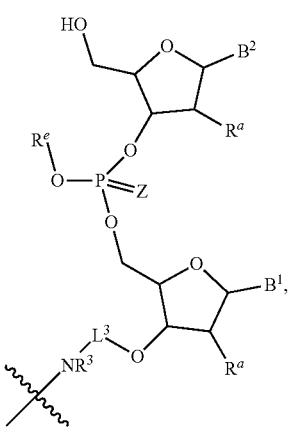

(IV')

wherein
Z is O or S; and
(d) isolating the 5' unblocked second bioconjugate.

In some embodiments of the method, the structure of Formula (IV) is also represented by (IVa) and the Formula (IV') is also represented by Formula (IV'a):

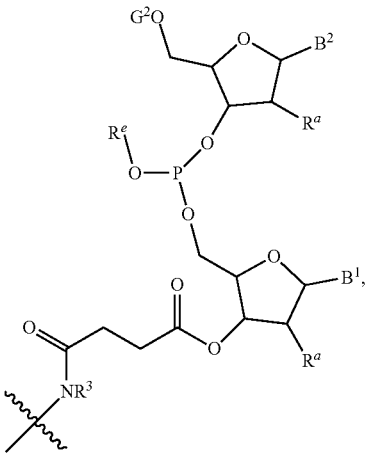

(IVa)

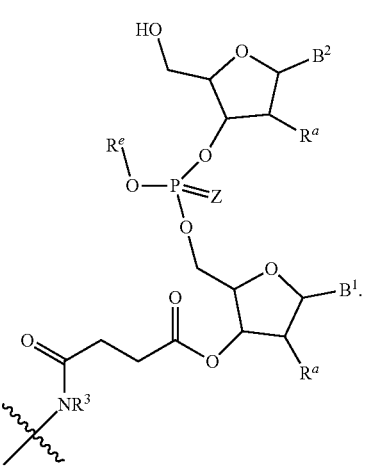

(IV'a)

In some embodiments, the method further comprises blocking unreacted 5' hydroxyl group in the 5' unblocked first bioconjugate prior to step (b).

In some embodiments of the method, $B^2$ is independently optionally protected adenine, optionally protected deaza adenine, optionally protected cytosine, optionally protected guanine, optionally protected deaza guanine, optionally protected thymine, or optionally protected uracil. In some further embodiments, $B^2$ is

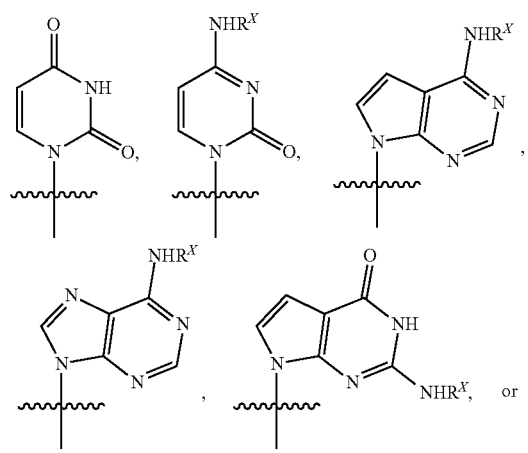

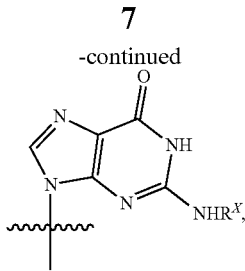

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group.

In some embodiments, $G^2$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In one embodiment, $G^2$ is bis(4-methoxyphenyl)phenylmethyl (DMT).

In some embodiments, isolation or purification of the 5' unblocked second bioconjugate is achieved by precipitation, filtration, ultrafiltration or dialysis. In further embodiments, such isolation or purification is achieved by using a regenerated cellulose membrane having a molecular weight cutoff (MWCO) from about 5 kDa to about 50 kDa.

In some embodiments of the method, steps (a)-(d) are repeated multiple cycles until one or more desired length of oligonucleotides have been synthesized. In further embodiments, steps (a)-(d) are repeated at least about 3, 4, 5, 6, 7, 8, 9, 10, 11, 12, 13, 14, 15 or 20 cycles. In some embodiments, the method further comprises removing the oligonucleotides from the PVH.

In some embodiments of the method, each of the first solvent and the second solvent comprise one or more non-protic polar solvents, or combinations thereof. In some embodiments, the one or more non-protic polar solvents comprise acetonitrile, tetrahydrofuran (THF), dimethylformamide (DMF), dimethyl sulfoxide (DMSO), dichloromethane (DCM), sulfolane, or combinations thereof.

In any embodiments of the method, the PVH has an average molecular weight from about 5 kDa to about 1000 kDa, or from about 10 kDa to about 100 kDa.

Another aspect of the present disclosure relates to oligonucleotides prepared by any of the methods described herein.

A further aspect of the present disclosure relates to a polymeric bioconjugate for liquid phase oligonucleotide synthesis comprising one or more repeating units of Formula (V):

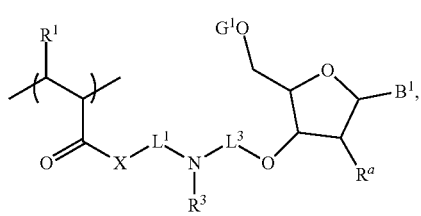

wherein

X is $NR^4$, S, or O;

each of $R^1$, $R^3$ and $R^4$ is independently H or $C_1$-$C_6$ alkyl;

$L^1$ is a heteroalkylene linker comprising one or more oxygen atoms;

$L^3$ is a cleavable heteroalkylene linker where one or more carbon atoms is replaced by O, S, N, C(=O) or C(=S);

$B^1$ is a nitrogenous base;

$G^1$ is a 5' hydroxyl blocking group; and $R^a$ is —H, —OH, halogen, —O—($C_1$-$C_6$ alkyl), —O—($C_1$-$C_6$ haloalkyl), or —OY, where Y is a 2' hydroxyl protecting group.

In some embodiments, the polymeric bioconjugate comprises a repeating unit of Formula (V) that is also represented by Formula (Va):

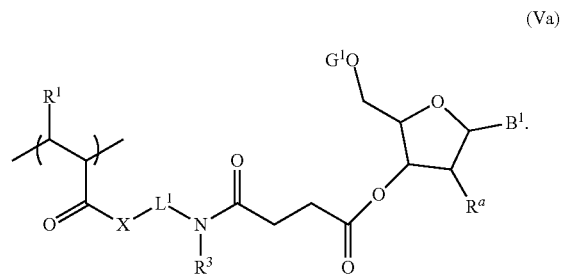

In some embodiments, the polymeric bioconjugate comprises one or more acrylamide or acrylate repeating units of Formula (II):

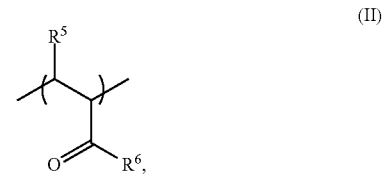

wherein:

$R^5$ is H or $C_1$-$C_6$ alkyl;

$R^6$ is —$NR^7R^8$ or —O-$L^2$-$R^9$;

each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and $L^2$ is a heteroalkylene linker comprising one or more oxygen atoms.

In some embodiments, the polymeric bioconjugate comprises or has the structure:

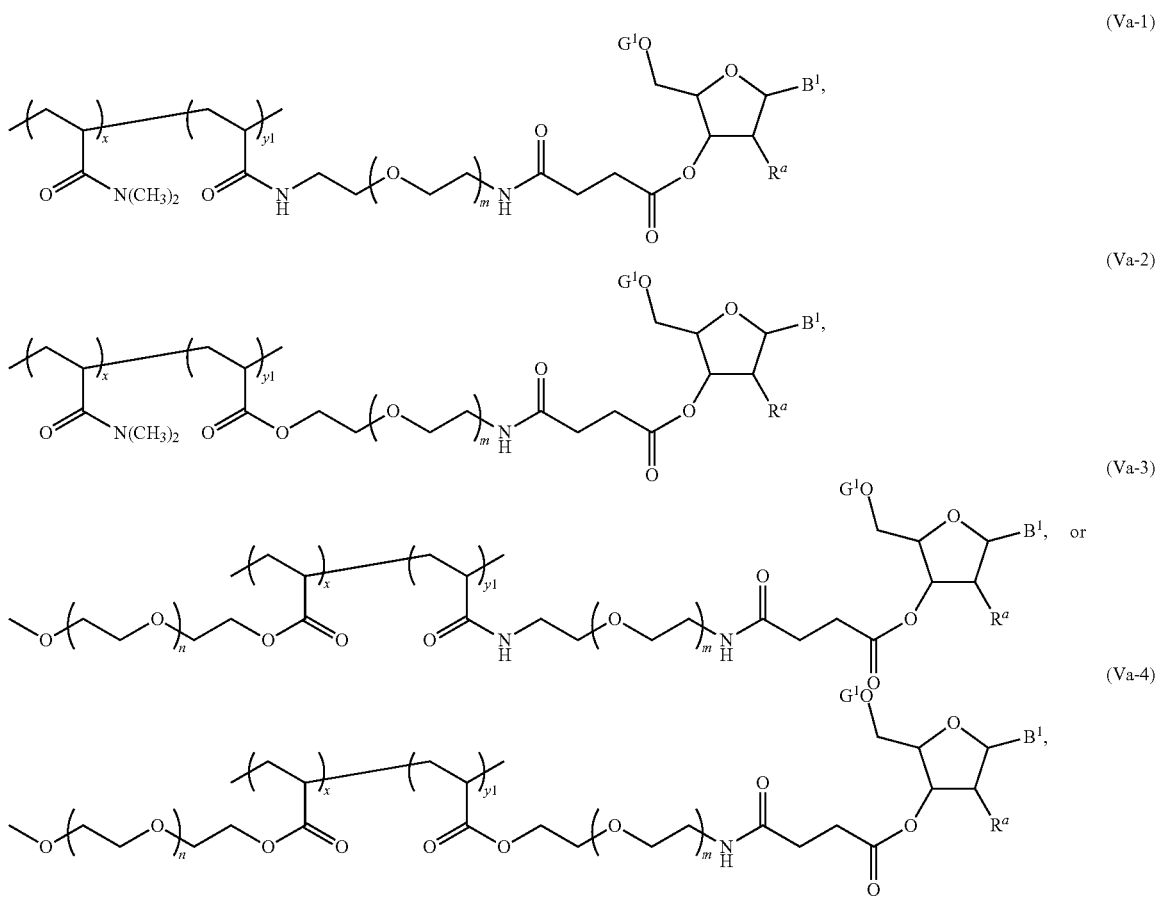

wherein each of m and n is independently an integer from about 2 to 200; and each of x and $y^1$ is independently an integer from 1 to 50,000. In further embodiments, the ratio of x to $y^1$ from about 50:1 to about 5:1. In further embodiments, y1 equals to or less than y as defined in the PVH described herein.

Another aspect of the present disclosure relates to a polymeric bioconjugate for liquid phase oligonucleotide synthesis comprising one or more repeating units of Formula (VI):

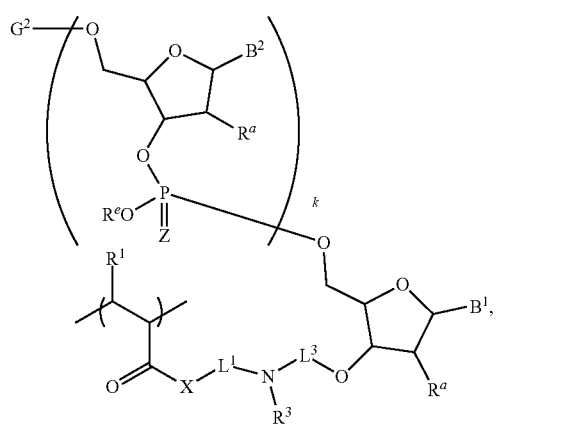

(VI)

wherein

X is $NR^4$, S, or O;

each of $R^1$, $R^3$ and $R^4$ is independently H or $C_1$-$C_6$ alkyl;

$L^1$ is a heteroalkylene linker comprising one or more oxygen atoms;

$L^3$ is a cleavable heteroalkylene linker where one or more carbon atoms is replaced by O, S, N, C(=O) or C(=S);

each of $B^1$ and $B^2$ is independently a nitrogenous base;

$G^2$ is a 5' hydroxyl blocking group; and each $R^a$ is independently H, —OH, halogen, —O—($C_1$-$C_6$ alkyl), —O—($C_1$-$C_6$ haloalkyl), or —OY, where Y is a 2' hydroxyl protecting group;

$R^e$ is unsubstituted or substituted $C_1$-$C_6$ alkyl;

Z is O or S; and k is an integer from 1 to 500.

In some embodiments, the polymeric bioconjugate comprises a repeating unit of Formula (VI) that is also represented by Formula (VIa):

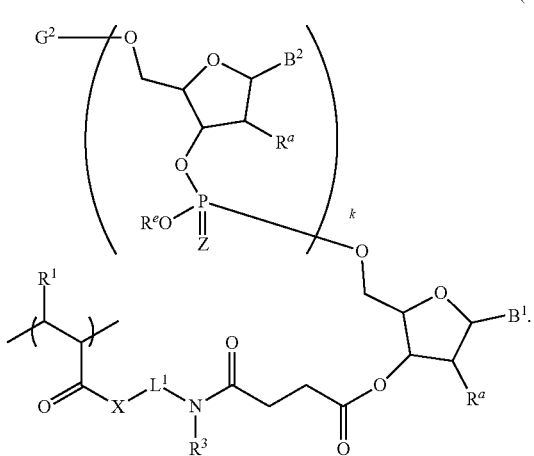
(VIa)

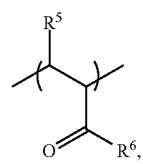
(II)

wherein:

R⁵ is H or $C_1$-$C_6$ alkyl;

R⁶ is —NR⁷R⁸ or —O-L²-R⁹;

each of R⁷, R⁸ and R⁹ is independently optionally substituted $C_1$-$C_6$ alkyl, optionally substituted phenyl, or R⁷ and R⁸ together with the nitrogen atom to which they are attached form an optionally substituted 5 or 6 membered heterocyclyl; and L² is a heteroalkylene linker comprising one or more oxygen atoms.

In some embodiments, the polymeric bioconjugate comprises the structure:

In some embodiments, the polymeric bioconjugate comprises one or more acrylamide or acrylate repeating units of Formula (II):

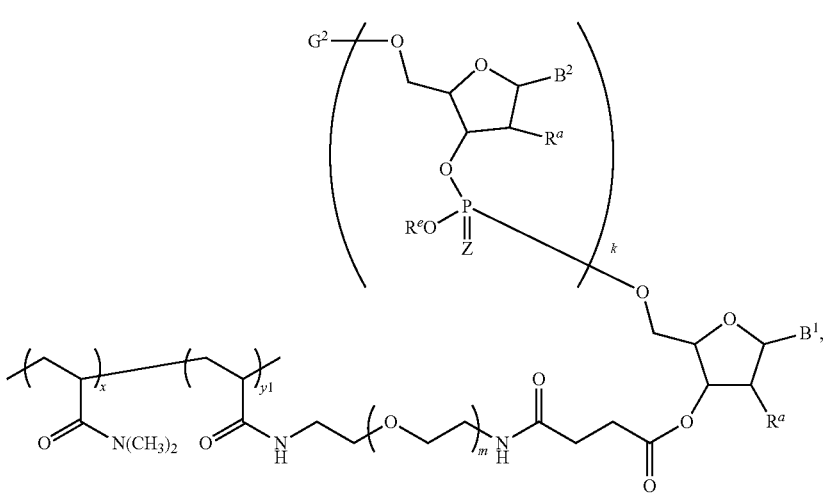
(VIa-1)

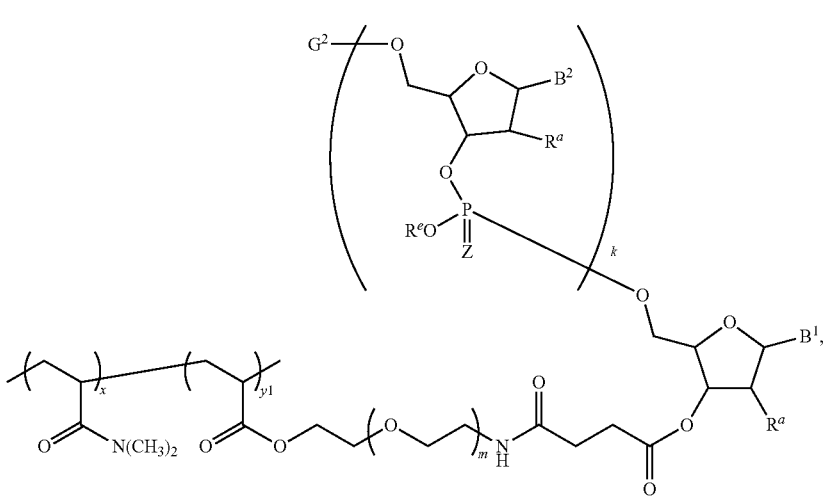
(VIa-2)

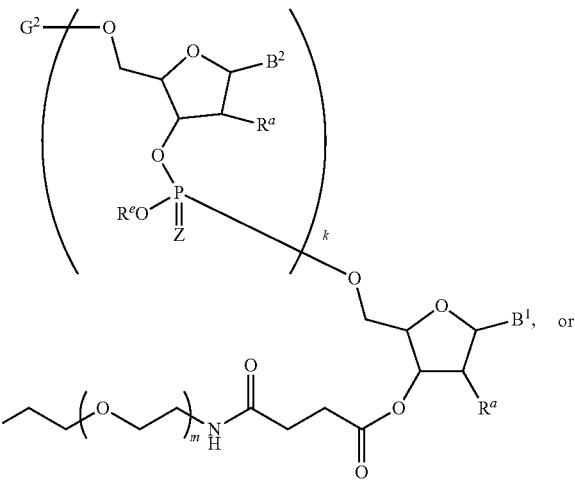

(VIa-3)

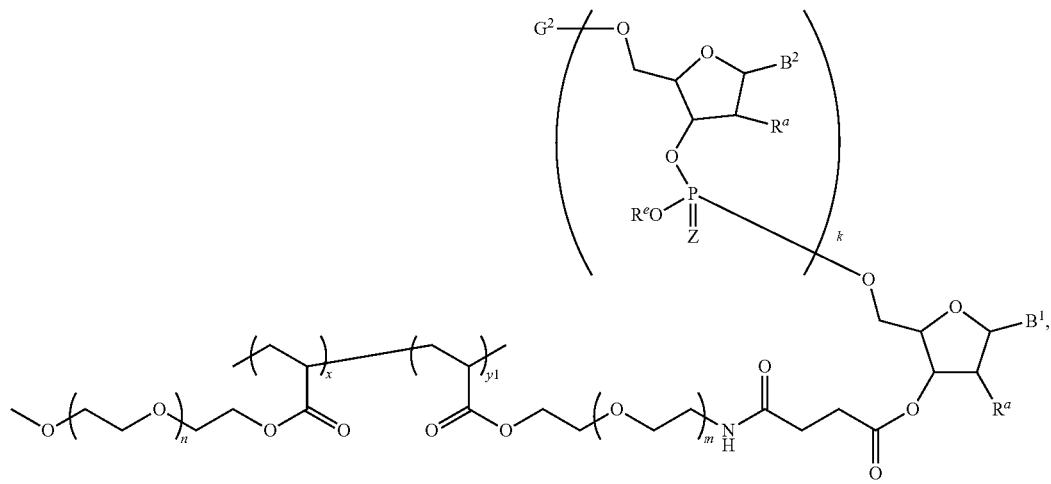

(VIa-4)

wherein each of m and n is independently an integer from about 2 to 200; each of m and n is independently an integer from about 2 to 200; and each of and each of x and $y^1$ is independently an integer from 1 to 50,000. In further embodiments, the ratio of x to $y^1$ from about 50:1 to about 5:1. In further embodiments, y1 equals to or less than y as defined in the PVH described herein.

In any embodiments of the polymers or polymeric bioconjugates described herein, it also includes the salt form thereof. For example, when the polymers or polymeric bioconjugates comprise a free amino group, the amino group may form a salt with an organic or inorganic acid, for example, trifluoroacetic acid (TFA).

BRIEF DESCRIPTION OF THE DRAWINGS

FIG. 3A is a $^1$H NMR spectrum measured in $CDCl_3$ of a DMT-dT conjugated poly($NH_2$-PEG-co-DMA) with 5 mol % of amino-PEG pendant according to an embodiment of the present application.

DETAILED DESCRIPTION

Figure 1:
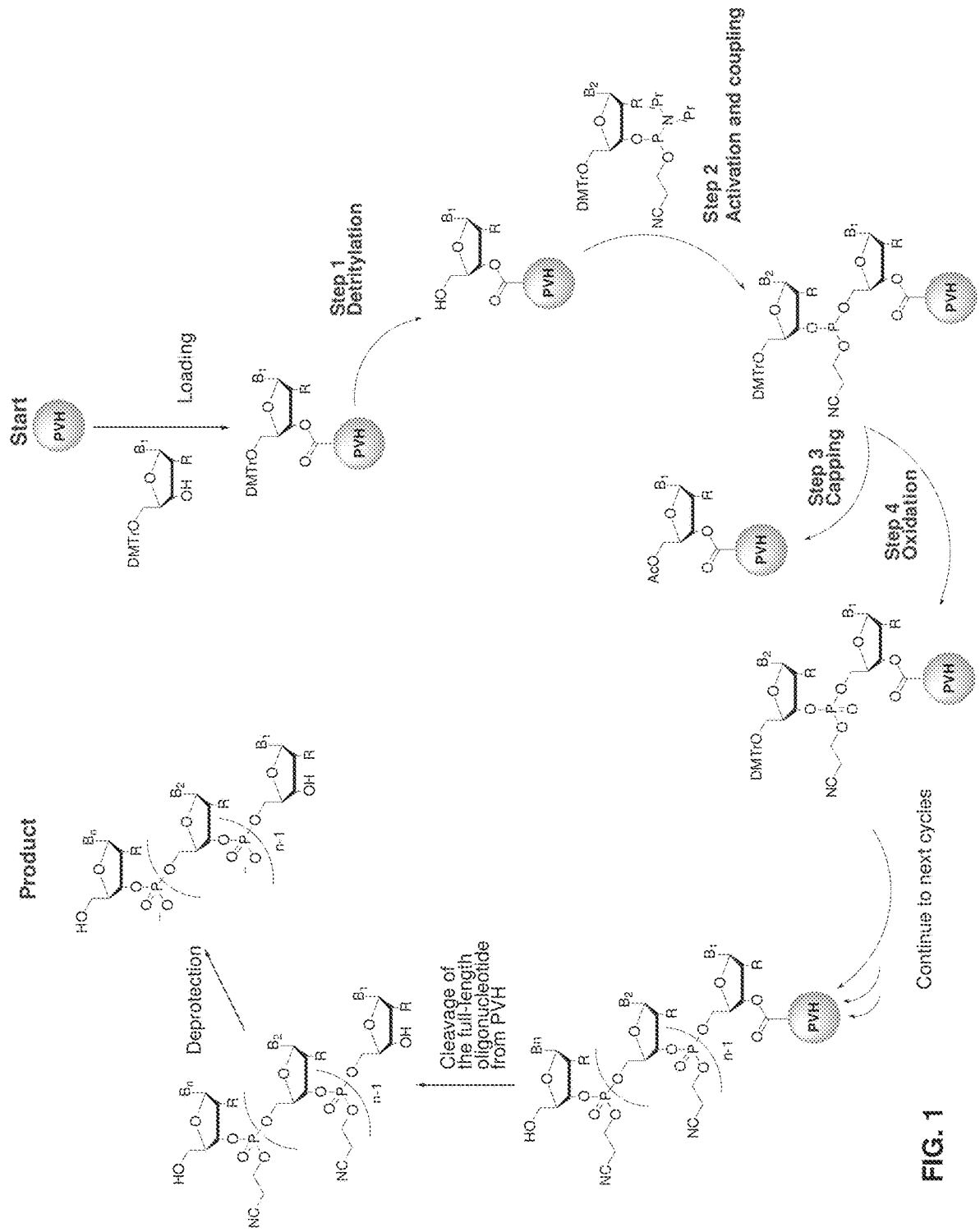
FIG. 1 is a general reaction scheme for making an oligonucleotide by liquid phase oligonucleotide synthesis according to an embodiment of the present application.

Solid phase oligonucleotide synthesis enable oligo synthesis at the solid support-liquid interface. The solid support is insoluble in the liquid medium (e.g., organic solvent). Examples of solid support include particles of controlled porous glass (CPG) and porous crosslink polystyrene. In contrast, liquid phase oligo synthesis (LPOS) relies on a soluble organic compound as support (hub) to carry out oligo synthesis in solution. Conventional LPOS typically utilizes soluble supports that have one or several functional groups as anchors to conjugate and synthesize oligos. Embodiments of the present disclosure relate to methods for liquid phase oligonucleotide synthesis by using a soluble polymeric polyvalent hub (PVH) that has a plurality of functional groups as anchors for oligo synthesis. For example, the PVH described herein may contain reactive amino groups that allows for efficient conjugation with nucleoside or nucleotide analogs with improved yield compared to known liquid phase oligonucleotide synthesis and solid phase oligonucleotide synthesis. Furthermore, the PVH of the present disclosure eliminates the use of succinate linker to attach the nucleoside or nucleotide analogs to the PVH. The methods described herein is amenable for multi-kilogram oligonucleotide synthesis and good loading capacity and oligo yield.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components. By "consisting of" is meant including, and limited to, whatever follows the phrase "consisting of." By "consisting essentially of" is meant including any elements listed after the phrase, and limited to other elements that do not interfere with or contribute to the activity or action specified in the disclosure for the listed elements.

As used herein, the term "average molecular weight" is the weight-average molecular weight (Mw) of a sample population made up of polymer species having a multiplicity of molecular weights. This quantity is defined by the equation:

$$M_w = \left(\sum_{i=1} n_i \times (M_i)^2\right) \bigg/ \sum_{i=1} n_i \times M_i$$

where $n_i$ indicates the number of molecules of species $i$ and $M_i$ is the molecular weight of $i^{th}$ species. As used herein, the term "molecular weight" refers to weight average molecular weight, unless otherwise specified.

As used herein, the term "polymer" used herein in its traditional sense, is a large molecule composed of smaller monomeric or oligomeric subunits covalently linked together to form a chain. A "homopolymer" is a polymer made up of only one monomeric repeating unit. A "copolymer" refers to a polymer made up of two or more kinds of monomeric repeating unit. Linear polymers are composed of monomeric subunits linked together in one continuous length to form polymer chains. Branched polymers are similar to linear polymers but have side chains protruding from various branch points along the main polymer. Star-shaped polymers are similar to branched polymers except that multiple side branches radiate from a single branch site, resulting in a star-shaped or wheel-and-spoke appearance.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a "cyano" group refers to a "—CN" group.

As used herein, a "nitro" group refers to a "—$NO_2$" group.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

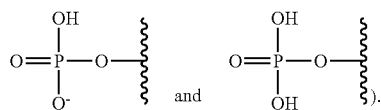

As used herein, the terms "monophosphate," "diphosphate," and "triphosphate" are used in their ordinary sense as understood by those skilled in the art, and include protonated forms.

As used herein, the terms "protecting group" and "blocking group" refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry Plenum Press*, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMT); 4,4'-dimethoxytrityl (DMT); or 4,4',4"-trimethoxytrityl (TMT)).

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the polymer or polymeric conjugate described herein may be in the form of a trifluoroacetate salt.

As used herein, the term "reactive ester" refers to either an acyclic or a cyclic ester functional group comprising the moiety —C(=O)O— that is highly susceptible toward nucleophilic attack.

As used herein, "loading capacity" or "load" is expressed in mmol or μmol of a nucleoside bound to the polyvalent hub (PVH) described herein per gram of PVH (i.e., mmol/g).

Polyvalent Polymer Hubs (PVHs) for Liquid Phase Oligonucleotide Synthesis

Several aspects of the present application relate to a polymer for liquid phase synthesis. In some embodiments, the liquid phase synthesis comprises liquid phase oligonucleotide synthesis, liquid phase peptide synthesis, liquid phase polynucleotide (i.e., nucleic acid), synthesis or liquid phase small molecule synthesis. In some embodiments, the polymer comprises or is a polymer for liquid phase oligonucleotide synthesis. The polymer is prepared from one or more monomers to produce the polymer having one or more repeating units. The monomers may include acrylic or methacrylic acid esters (e.g., acrylate) or combinations thereof, where certain acrylate monomers contain a reactive ester group that allows for reaction with nucleoside or nucleotide analogs. The polymer may also contain repeating units of acrylic or methacrylic acid amides (e.g., acrylamide), or combination thereof. The polymer may comprise a linear polymer, a branched polymer, or a star-shaped polymer, or combinations thereof. The polymer may comprise a homopolymer, a block copolymer, or a random copolymer, or combinations thereof.

In some embodiments of the polymer described herein, the polymer comprises one or more repeating units of Formula (I):

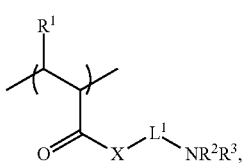
(I)

wherein X is NR⁴, S, or O; each of $R^1$, $R^2$, $R^3$ and $R^4$ is independently H or $C_1$-$C_6$ alkyl; and $L^1$ is a heteroalkylene linker comprising one or more oxygen atoms. In some such embodiments, $L^1$ comprises 3 to 5000 membered heteroalkylene. In some such embodiments, the non-limiting members of $L^1$ comprise carbon (C) and oxygen (O). In some embodiments, the moieties of $L^1$ comprise a functional group, nonlimiting examples of which include hydroxyl, alkoxy, ether, and carbonyl. In some embodiments, the moieties of $L^1$ increase the water solubility of the polymer. In some embodiments, $R^1$ is H. In certain embodiments, the repeating unit of Formula (I) is also represented by Formula (Ia):

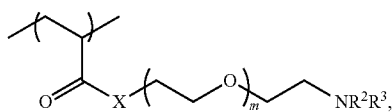
(Ia)

wherein m is an integer of 1 to 1000. In other embodiments, the repeating unit of Formula (I) is also represented by Formula (Ib):

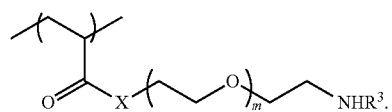
(Ib)

In some such embodiments, $R^3$ is H. In some embodiments, X is NH and m is 2. In some embodiments, X is O, and m is from about 10 to 200. In further embodiments, the number of m is at least 5, 10, 20, 30, 40, 50, 60, 70, 80, 90, 100, 200, 300, 400, 500, 600, 700, 800, 900, or 950. In further embodiment, the polymer is a homopolymer consisting of repeating units of Formula (I), (Ia) or (Ib).

In some embodiments, the polymer further comprises one or more acrylamide or acrylate repeating units of Formula (II):

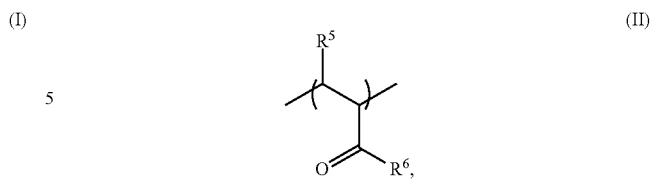
(II)

wherein $R^5$ is H or $C_1$-$C_6$ alkyl; $R^6$ is —$NR^7R^8$ or —O-$L^2$-$R^9$; each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and $L^2$ is a heteroalkylene linker comprising one or more oxygen atoms. In some embodiments, $R^5$ is H. In certain embodiments, $R^6$ is —$NR^7R^8$, and the repeating unit of Formula (II) is also represented by Formula (IIa):

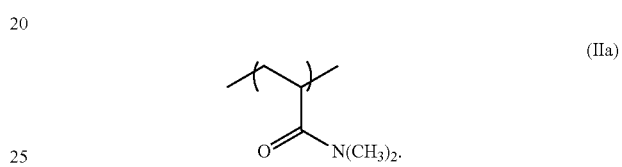
(IIa)

In other embodiments, $R^6$ is —O-$L^2$-$R^9$, and the repeating unit of Formula (II) is also represented by Formula (IIb):

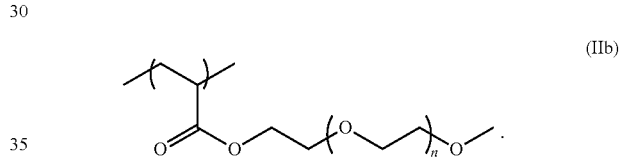
(IIb)

wherein n is an integer of 1 to 1000. In some such embodiments, the molar ratio of repeating units of Formula (I) (including Formula (Ia) or (Ib)) to the repeating units of formula (II) (including Formula (IIa) or (IIb)) is from about 1:200 to 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, from about 5:1 to about 1:5, from about 4:1 to about 1:4, from about 3:1 to about 1:3, from about 2:1 to about 1:2; or about 1:1. In some embodiments, the molar ratio of repeating units of Formula (I) (including Formula (Ia) or (Ib)) to the repeating units of formula (II) (including Formula (IIa) or (IIb)) is about 1:80, 1:79, 1:50, 1:20, 1:19, 1:10, 1:9, 1:5, 1:4, 1:3, 1:2 or 1:1. In some embodiments, the polymer comprises

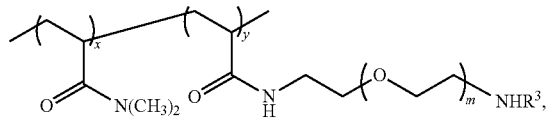 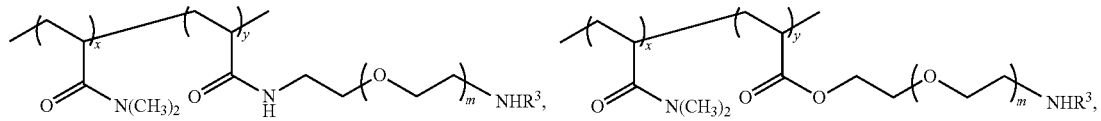

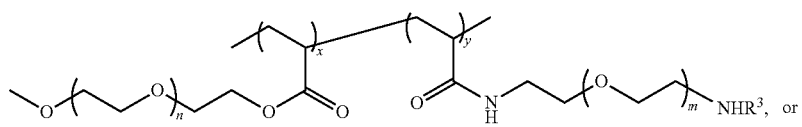, or

-continued

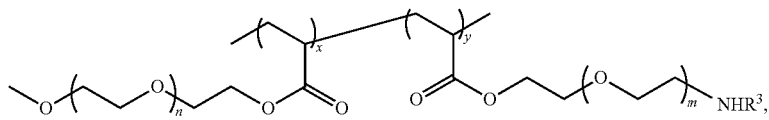

wherein each of m and n is independently an integer from about 2 to 200; and each of x and y is independently an integer from 1 to 50,000. In some such embodiments, $R^3$ is H. In further embodiments, m is 5, 10, 20, 30, 40, 50, 60, 70, 80, 90, 100, 110, 120, 130, 140, 150, 160, 170, 180, 190, or 200. In further embodiments, n is 5, 10, 20, 30, 40, 50, 60, 70, 80, 90, 100, 110, 120, 130, 140, 150, 160, 170, 180, 190, or 200. In further embodiments, x is 5, 100, 500, 1,000, 2,000, 5,000, 10,000, 15,000, 20,000, 25,000, 30,000, 35,000, 40,000, 45,000, or 50,000. In further embodiments, y is 5, 100, 500, 1,000, 2,000, 5,000, 10,000, 15,000, 20,000, 25,000, 30,000, 35,000, 40,000, 45,000, or 50,000. In some embodiments, the ratio of x:y may range from about 1:1000 to about 1000:1, from about 1:500 to about 500:1, from about 1:200 to about 200:1, from about 1:100 to about 100:1, from about 1:70 to about 70:1, from about 1:50 to about 50:1, from about 1:20 to about 20:1, from about 1:10 to about 10:1, or from about 1:5 to about 5:1, from about 4:1 to about 1:4, from about 3:1 to about 1:3, from about 2:1 to about 1:2; or about 1:1. . In further embodiments, the ratio of x:y is about 1:80, 1:79, 1:50, 1:20, 1:19, 1:10, 1:9, 1:5, 1:4, 1:3, 1:2 or 1:1. When the polymer comprises both repeating units of Formula (I) and (II), such polymer may be a block copolymer or a random copolymer.

Method of Preparing Oligonucleotide by Liquid Phase Oligonucleotide Synthesis (LPOS)

Several aspects of the present application relate to a method for making a compound by liquid phase synthesis. The compound may be an oligonucleotide, a peptide, a polynucleotide (i.e., nucleic acid), or a small molecule. In certain embodiments, the method is for making an oligonucleotide by liquid phase oligonucleotide synthesis.

In some embodiments of the method described herein, the method includes dissolving a polyvalent hub (PVH) comprising a polymer (homopolymer or copolymer) as described herein in a first solvent to form a reaction matrix, contacting, or otherwise reacting, the PVH with one or more nucleoside analogs to form a first bioconjugate comprising a structure of Formula (III):

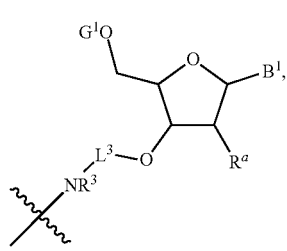

wherein $B^1$ is a nitrogenous base; $G^1$ is a 5' hydroxyl blocking group; $R^a$ is —H, —OH, halogen, —O—($C_1$-$C_6$ alkyl), —O—($C_1$-$C_6$ haloalkyl), or —OY, where Y is a 2' hydroxyl protecting group; and $L^3$ is a cleavable heteroalkylene linker where one or more carbon atoms is replaced by O, S, N, C(=O) or C(=S). In some such embodiments, the nitrogenous base comprises a purine base, a deazapurine base, or a pyrimidine base. In some embodiments, the structure of Formula (III) is also represented by Formula (IIIa):

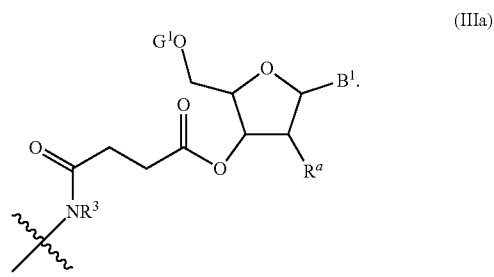

In some such embodiments, $R^3$ is H.

In further embodiments of the method, the first bioconjugate may comprise or have the repeating unit of Formula (V):

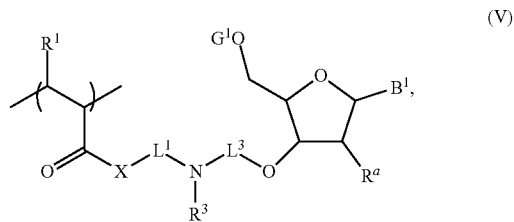

wherein the definitions of $R^1$, X, and $L^1$ are described in the PVH of formula (I) as described herein. In further embodiments, the repeating unit of Formula (V) is also represented by Formula (Va):

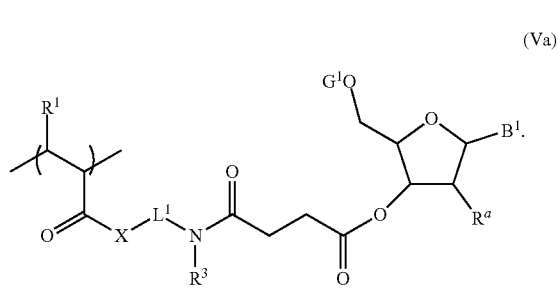

In still further embodiments, the PVH used in the LPOS is a copolymer and the first bioconjugate further comprises the repeating unit of Formula (II)

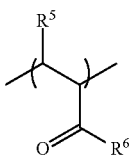

as described herein. In still further embodiments, the first bioconjugate may comprise or have the structure:

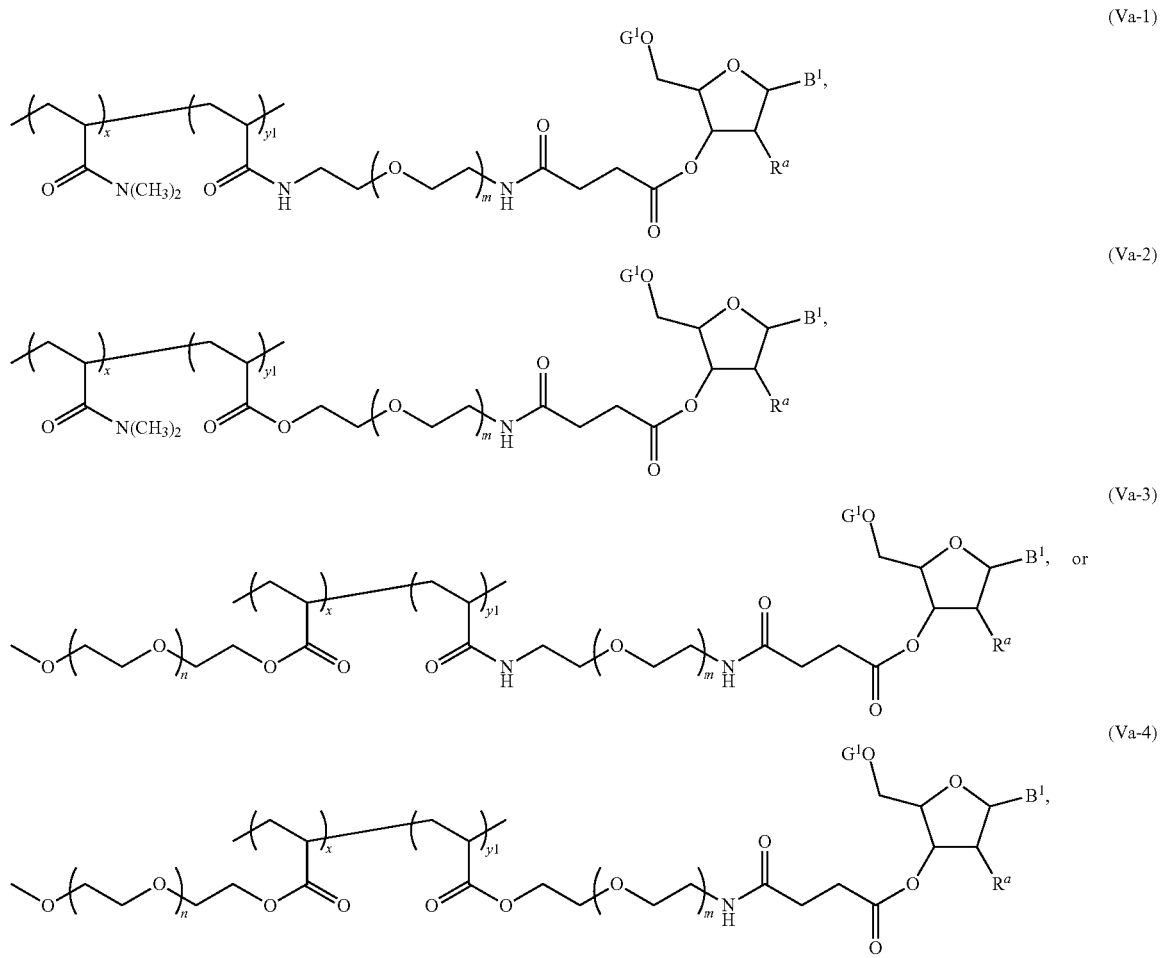

wherein each of m and n is independently an integer from about 2 to 200; and each of x and y¹ is independently an integer from 1 to 50,000. In further embodiments, y1 is equal to or less than y as defined in the PVH structure. If all reactive functional group of the PVH have been used in conjugating with the first nucleoside analog then y1 equals to y. If there are still certain reactive functional group remain unreacted, then the first bioconjugate may further comprises one or more repeating units of the structure:

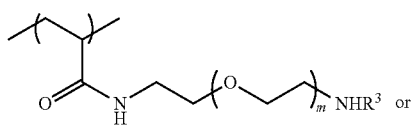

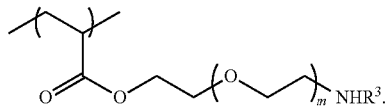

In some embodiments of the method described herein, $B^1$ is independently optionally protected adenine, optionally protected deaza adenine, optionally protected cytosine, optionally protected guanine, optionally protected deaza guanine, optionally protected thymine or optionally protected uracil. In some embodiments, $B^1$ is

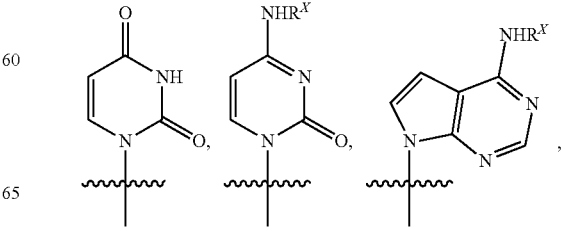

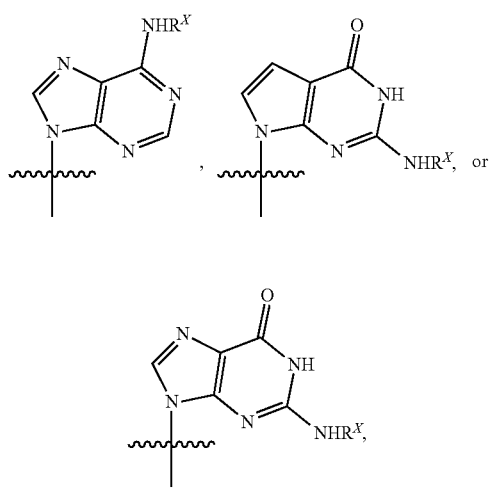

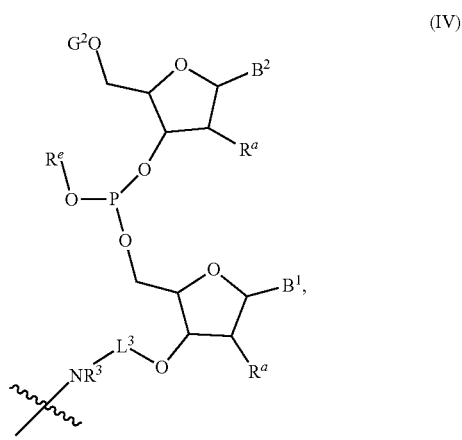

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments, $G^1$ is a trityl type of hydroxy protecting group selected from the group consisting of (4-methoxyphenyl)diphenylmethyl, bis(4-methoxyphenyl) phenylmethyl, tris(4-methoxyphenyl)methyl, 9-phenylxanthen-9-yl, and 9-(4-methoxyphenyl)xanthen-9-yl. In some embodiments, $G^1$ is bis(4-methoxyphenyl)phenylmethyl (DMT).

In some embodiments, the PVH has an average molecular weight from about 5 kDa to about 1000 kDa, or from about 10 kDa to about 1000 kDa, or from about 20 kDa to about 500 kDa, or from about 30 kDa to about 100 kDa. In some embodiments, the PVH has the average molecular weight from about 10 kDa to about 100 kDa. The PVH having an average molecular weight (MW) of about 30 KDa or higher extends into the bulk of the liquid phase, resulting in improved reaction kinetics and reaction yield. Furthermore, such PVH also facilitates rapid discharge of reaction debris and unreacted biomolecules having an average MW of about 2 K or less.

In some embodiments of the method described herein, the method further comprises: removing the 5' hydroxyl blocking group ($G^1$) to form a 5' unblocked first bioconjugate; and isolating the 5' unblocked first bioconjugate. In some such embodiments, isolation of the 5' unblocked first bioconjugate is achieved by precipitation, dialysis or filtration. In some embodiments, the isolation is achieved by a filtration step. The filtration step may include dialysis, filtration, nanofiltration, ultrafiltration, or any known filtration technology suitable for use herein, and combinations thereof. In some embodiments, the filtration step comprises dialysis or filtration. In further embodiments, filtration step includes the use of a membrane. The membrane may comprise a cellulose acetate, a glass fiber, a carbon-based polymer, a regenerated cellulose and combinations thereof. In certain embodiments, the regenerated cellulose has an electrostatic charge. In some embodiments, the regenerated cellulose membrane is negatively charged. In some embodiments, the regenerated cellulose comprises the structure:

In some embodiments, the regenerated cellulose has a molecular weight cutoff (MWCO) from about 5 kDa to about 50 kDa, from about 6 kDa to about 40 kDa, about 7kDa to about 30 kDa, or about 8kDa to about 12 kDa. The regenerated cellulose membrane is capable of retaining the PVH containing bioconjugate as an alternative to the expensive nanofiltration membranes prepared with polyimide. The negatively charged membrane capable of reducing non-specific adsorption of negatively charged biomolecules. In some embodiments, the regenerated cellulose is treated in a process including carbon disulfide followed by an aqueous metal hydroxide. In some embodiments, the regenerated cellulose comprises dithiolate groups and metal cations. In some embodiments, the metal cations comprise group 1 metals (i.e., group IA metals or alkali metals), group 2 metals (i.e., group IIA metals or alkaline earth metals) and combinations thereof. In some embodiments, the metal cations comprise sodium cations.

In some embodiments of the method described herein, the method further comprises: (a) reacting the 5' unblocked first bioconjugate with one or more nucleoside phosphoramidite analogs in a second solvent to form a second bioconjugate comprising the structure of Formula (IV):

(IV)

wherein $G^2$ is a 5' hydroxyl blocking group; $B^2$ is a nitrogenous base; and $R^e$ is a phosphite protecting group;

(b) oxidizing the phosphite moiety in Formula (IV);

(c) removing the 5' blocking group $G^2$ to form a 5' unblocked second bioconjugate comprising the structure of Formula (IV'):

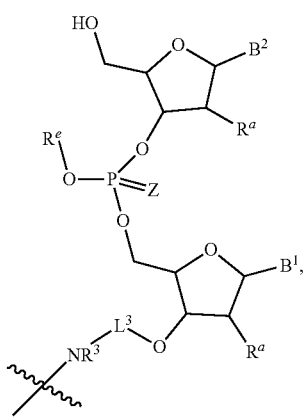

(IV')

wherein Z is O or S; and (d) isolating the 5' unblocked second bioconjugate. In some such embodiments, the structure of Formula (IV) is also represented by (IVa) and the Formula (IV') is also represented by Formula (IV'a):

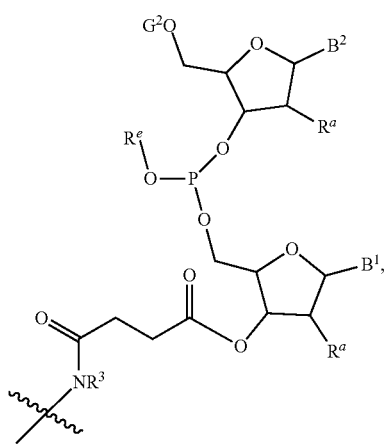

(IVa)

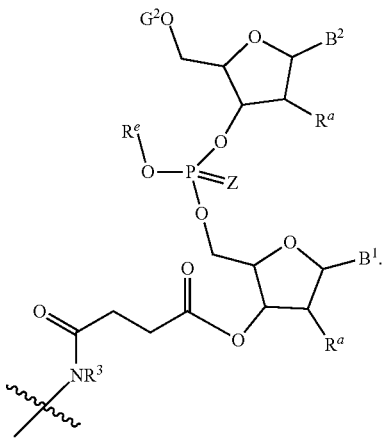

(IV'a)

In some such embodiments, $R^e$ is unsubstituted $C_1$-$C_6$ alkyl or substituted $C_1$-$C_6$ alkyl. A nonlimiting example of a substituted $C_1$-$C_6$ alkyl suitable for use as $R^e$ includes —$CH_2CH_2CN$. In some embodiments, the method further comprises blocking unreacted 5' hydroxyl group in the 5' unblocked first bioconjugate prior to step (b). In some such embodiments, $R^3$ is H.

In some further embodiments of the method, the second bioconjugate may comprise or have the repeating unit of Formula (VI):

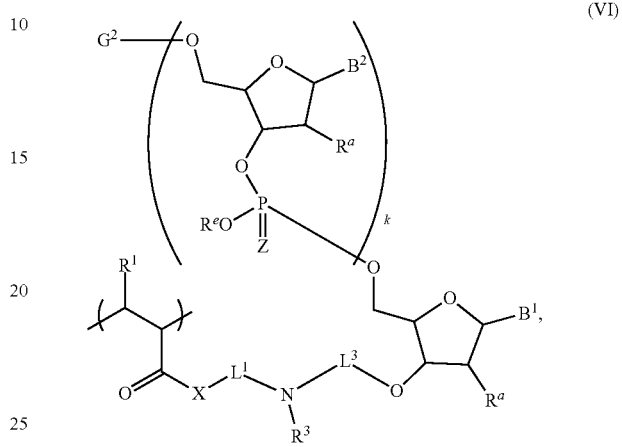

(VI)

wherein the definitions of $R^1$, X, and $L^1$ are described in the PVH of formula (I) as described herein. In further embodiments, the repeating unit of Formula (VI) is also represented by Formula (VIa):

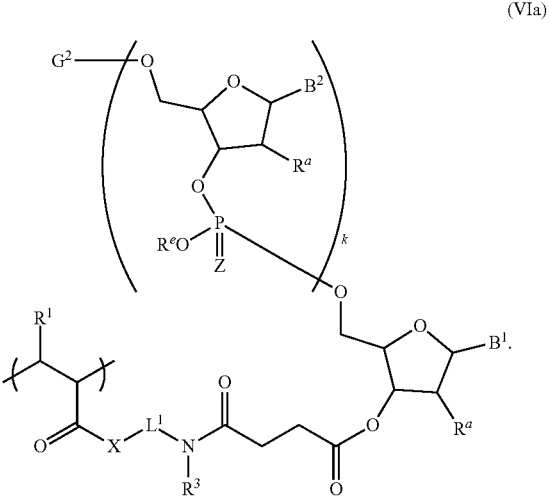

(VIa)

In still further embodiments, the PVH used in the LPOS is a copolymer and the first bioconjugate further comprises the repeating unit of Formula (II)

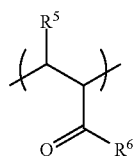

as described herein. In still further embodiments, the first bioconjugate may comprise or have the structure:
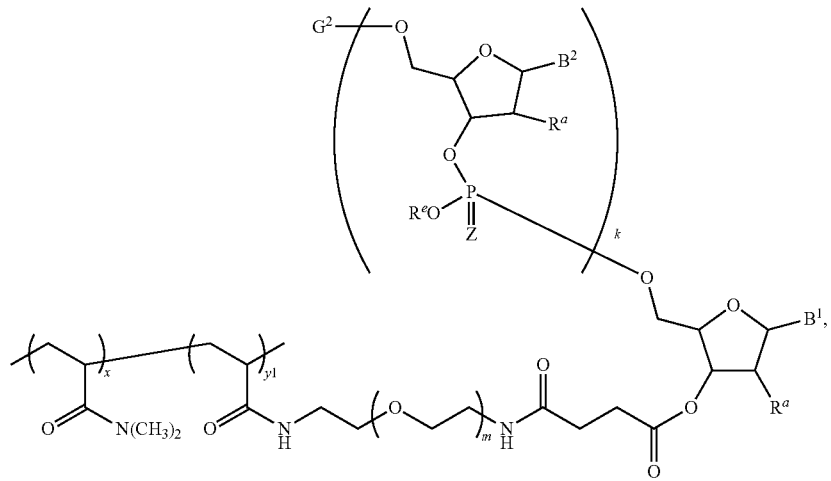
(VIa-1)
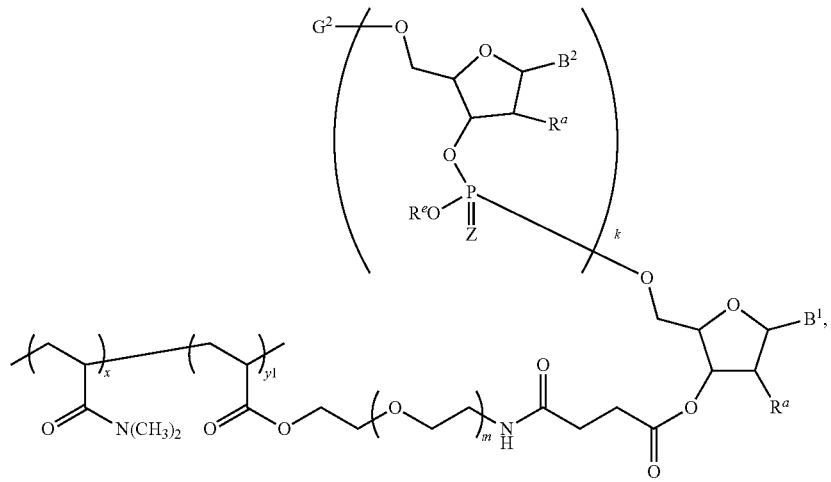
(VIa-2)
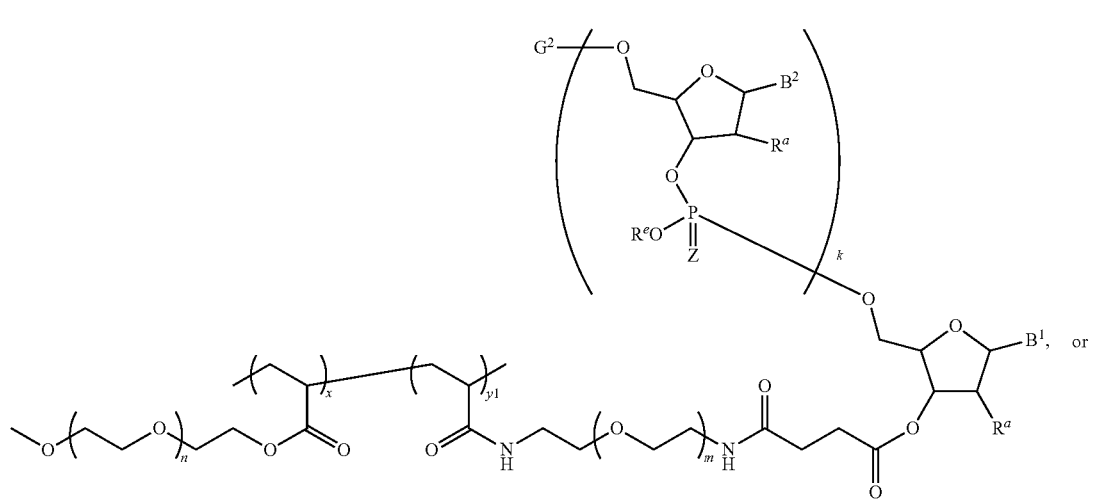
(VIa-3)

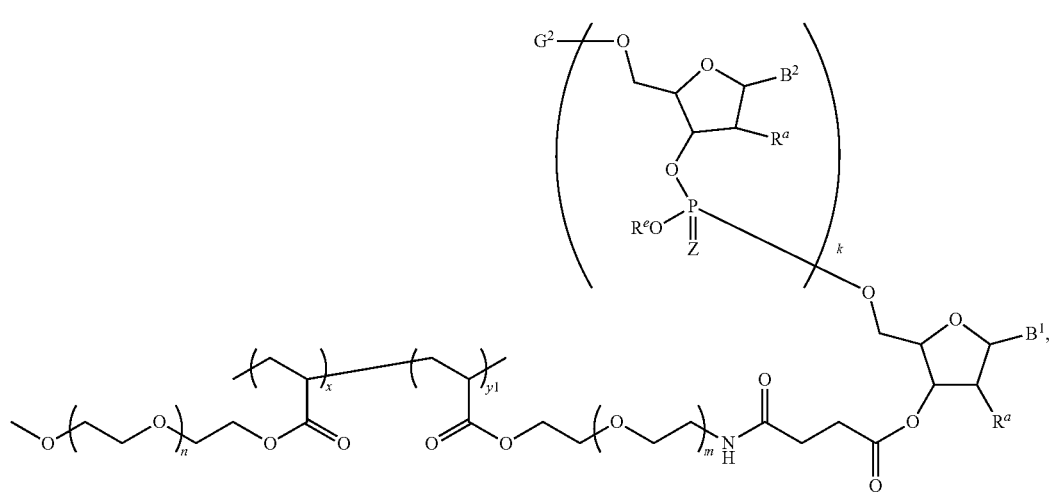

(VIa-4)

wherein each of m and n is independently an integer from about 2 to 200; each of m and n is independently an integer from about 2 to 200; and each of and each of x and $y^1$ is independently an integer from 1 to 50,000. If all reactive functional group of the PVH have been used in conjugating with the first nucleoside analog then y1 equals toy. If there are still certain reactive functional group remain unreacted, then the second bioconjugate may further comprises one or more repeating units of the structure:

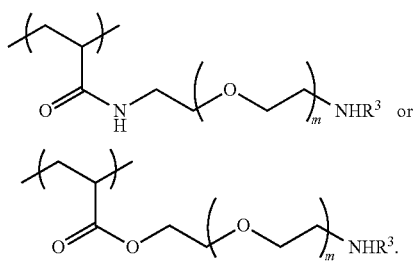

In some embodiments of the method described herein, $B^2$ is independently optionally protected adenine, optionally protected deaza adenine, optionally protected cytosine, optionally protected guanine, optionally protected deaza guanine, optionally protected thymine, or optionally protected uracil. In some embodiments, $B^2$ is

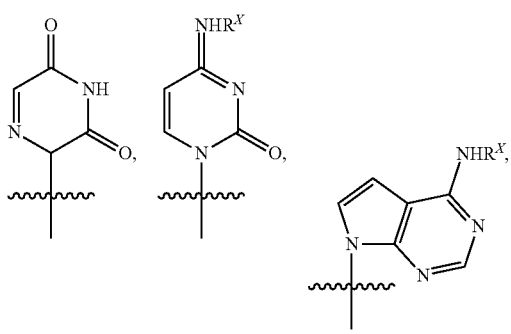

wherein $R^x$ is hydrogen, unsubstituted or substituted $C_1$-$C_6$ alkyl, or an amino protecting group, or the hydrogen in —$NHR^x$ is absent and $R^x$ is a divalent amino protecting group. In some embodiments of the method described herein, $G^2$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl, and 9-(4-methoxyphenyl)xanthen-9-yl. In some embodiments, $G^2$ is bis(4-methoxyphenyl)phenylmethyl (DMT).

In some embodiments of the method described herein, the method further comprises blocking unreacted 5' hydroxyl group in the 5' unblocked first bioconjugate prior to step (b). In some such embodiment, said blocking is performed by reacting the 5' hydroxyl group with acetic anhydride ($Ac_2O$).

In some embodiments of the method described herein, isolation or purification of the 5' unblocked second bioconjugate is achieved by precipitation, filtration, or dialysis. In further embodiments, the isolation/purification uses a regenerated cellulose membrane having a molecular weight cutoff (MWCO) from about 5 kDa to about 50 kDa, from about 6 kDa to about 40 kDa, about 7 kDa to about 30 kDa, or about 8 kDa to about 12 kDa. In some further embodiments, steps (a)-(d) are repeated multiple cycles until a desired length of oligonucleotide has been synthesized.

In some embodiments of the method described herein, steps (a)-(d) are repeated multiple cycles until one or more desired length of oligonucleotides have been synthesized. In some such embodiments, steps (a)-(d) are repeated at least about 2, 3, 4, 5, 6, 7, 8, 9, 10, 11, 12, 13, 14, 15, 16, 17, 18, 19 or 20 cycles. In some such embodiments, the oligonucleotide synthesized may comprises at least 2, 3, 4, 5, 6, 7, 8, 9, 10, 11, 12, 13, 14, 15, 16, 17, 18, 19 or 20 bases.

In some embodiments of the method described herein, the method further comprises removing the oligonucleotides from the PVH. In some such embodiments, the removing step includes a step of covalent chemical bond scission. In some embodiments, the removing step includes hydrolysis. In certain embodiments, the removing includes hydrolysis at a temperature from about 0° C. to about 80° C., or about 10° C. to about 60° C., or about 15° C. to about 30° C. In further embodiments, when the first nucleoside is covalently attached to the PVH through reaction of the 3'-succinic acid reacting with the amino group of the PVH, the amide bond formed between the first nucleoside and the PVH may be cleaved by hydrolysis.

In some embodiments of the method described herein, each of the first solvent and the second solvent comprise one or more non-protic polar solvents, or combinations thereof. In some embodiments, the one or more non-protic polar solvents comprise acetonitrile, tetrahydrofuran (THF), dimethylformamide (DMF), dimethyl sulfoxide (DMSO), dichloromethane (DCM), sulfolane, or combinations thereof. In one embodiment, the first solvent and/or the second solvent comprises acetonitrile. In another embodiment, the first solvent and/or the second solvent comprises a mixture of acetonitrile and sulfolane.

A general reaction scheme of the liquid phase oligonucleotide synthesis is illustrated in FIG. 1.

Additional embodiments of the present application relate to an oligonucleotide prepared by any of the methods described herein.

Polymeric Bioconjugate for Liquid Phase Oligonucleotide Synthesis

Several aspects of the present application relate to a polymeric bioconjugate for liquid phase synthesis. In some embodiments, the liquid phase synthesis comprises liquid phase oligonucleotide synthesis, liquid phase peptide synthesis, liquid phase polynucleotide (i.e., nucleic acid), synthesis or liquid phase small molecule synthesis. In some embodiments, the polymeric bioconjugate comprises or is a polymeric bioconjugate for liquid phase oligonucleotide synthesis. The polymeric bioconjugate is prepared from a polymer as described herein comprising one or more monomers to produce the polymer having one or more repeating units. The monomers may include acrylic or methacrylic acid esters (e.g., acrylate) or combinations thereof, where certain acrylate monomers contain a reactive ester group that allows for reaction with nucleoside or nucleotide analogs. The polymer of the polymeric bioconjugate may also contain repeating units of acrylic or methacrylic acid amides (e.g., acrylamide), or combination thereof. The polymer of the polymeric bioconjugate may comprise a linear polymer, a branched polymer, or a star-shaped polymer, or combinations thereof. The polymer of the polymeric bioconjugate may comprise a homopolymer, a block copolymer, or a random copolymer, or combinations thereof.

In some embodiments of the polymeric bioconjugate described herein, the polymeric bioconjugate comprises one or more repeating units of Formula (V):

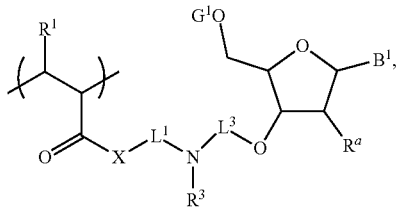

(V)

wherein X is $NR^4$, S, or O; each of $R^1$, $R^3$ and $R^4$ is independently H or $C_1$-$C_6$ alkyl; $L^1$ is a heteroalkylene linker comprising one or more oxygen atoms; $L^3$ is a cleavable heteroalkylene linker where one or more carbon atoms is replaced by O, S, N, C(=O) or C(=S); $B^1$ is a nitrogenous base described herein; $G^1$ is a 5' hydroxyl blocking group described herein; and $R^a$ is —H, —OH, halogen, —O—($C_1$-$C_6$ alkyl), —O—($C_1$-$C_6$ haloalkyl), or —OY, where Y is a 2' hydroxyl protecting group. In some such embodiments, $L^1$ comprises 3 to 5000 membered heteroalkylene. In some such embodiments, the non-limiting members of $L^1$ comprise carbon (C) and oxygen (O). In some embodiments, the moieties of $L^1$ comprise a functional group, nonlimiting examples of which include hydroxyl, alkoxy, ether, and carbonyl. In some embodiments, $R^3$ is H. In some such embodiments, the polymeric bioconjugate comprises a repeating unit of Formula (V) that is also represented by Formula (Va):

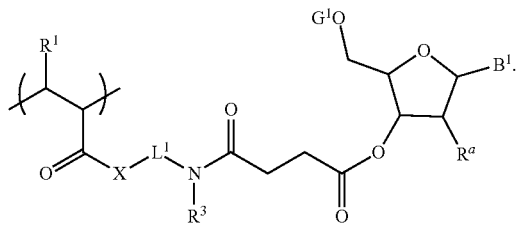

(Va)

In some embodiments, the polymeric bioconjugate comprises one or more acrylamide or acrylate repeating units of Formula (II):

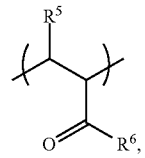

(II)

wherein: $R^5$ is H or $C_1$-$C_6$ alkyl; $R^6$ is —$NR^7R^8$ or —O-$L^2$-$R^9$; each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and $L^2$ is a heteroalkylene linker comprising one or more oxygen atoms. In some such embodiments, the molar ratio of repeating units of Formula (V) (including Formula (Va)) to the repeating units of formula (II) (including Formula (IIa) or (IIb)) is from about 1:200 to 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, from about 5:1 to about 1:5, from about 4:1 to about 1:4, from about 3:1 to about 1:3, from about 2:1 to about 1:2; or about 1:1. In some embodiments, the polymeric bioconjugate comprises the structure:

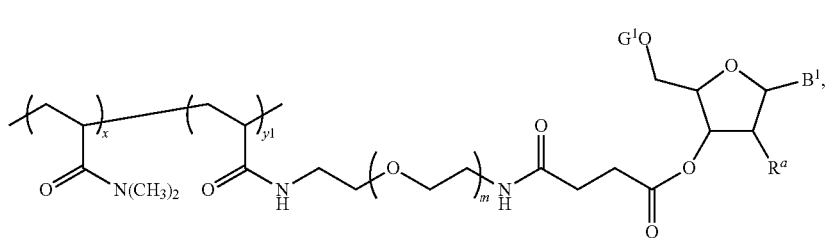
(Va-1)

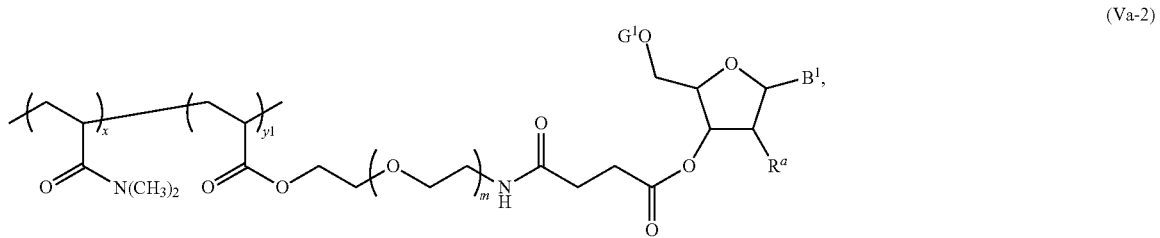
(Va-2)

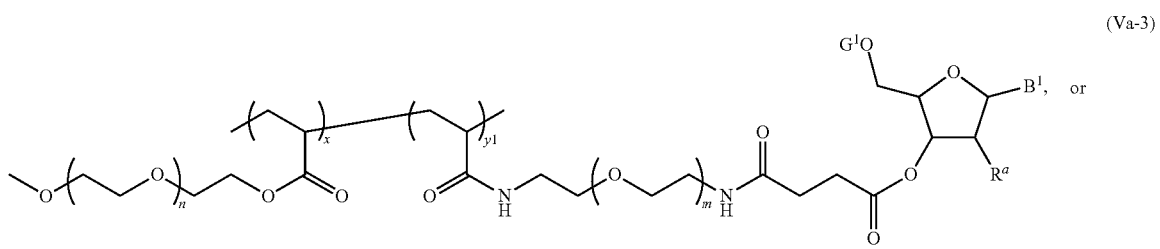
(Va-3) or

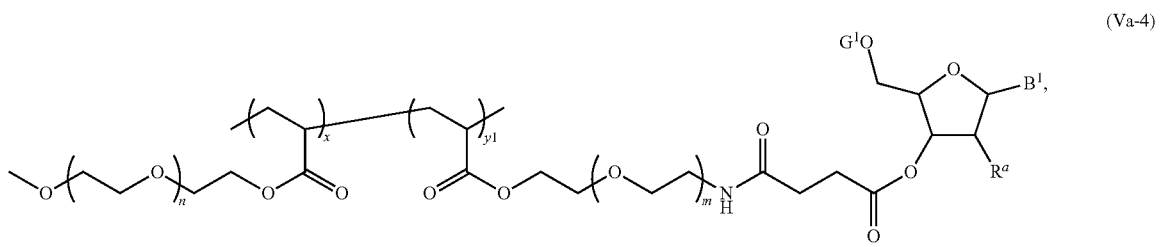
(Va-4)

wherein each of m and n is independently an integer from about 2 to 200; and each of x and $y^1$ is independently an integer from 1 to 50,000. In further embodiments, m is 5, 10, 20, 30, 40, 50, 60, 70, 80, 90, 100, 110, 120, 130, 140, 150, 160, 170, 180, 190, or 200. In further embodiments, n is 5, 10, 20, 30, 40, 50, 60, 70, 80, 90, 100, 110, 120, 130, 140, 150, 160, 170, 180, 190, or 200. In further embodiments, x is 5, 100, 500, 1,000, 2,000, 5,000, 10,000, 15,000, 20,000, 25,000, 30,000, 35,000, 40,000, 45,000, or 50,000. In further embodiments, $y^1$ is 5, 100, 500, 1,000, 2,000, 5,000, 10,000, 15,000, 20,000, 25,000, 30,000, 35,000, 40,000, 45,000, or 50,000. In some such embodiments, the polymeric bioconjugate includes a ratio of x to $y^1$ from about 100:1 to about 1:1, from about 50:1 to about 2:1, from about 20:1 to about 4:1 or from about 10:1 to about 5:1. In some embodiments, ratio of x to $y^1$ is about 50:1, 45:1, 40:1, 35:1, 30:1, 25:1, 20:1, 15:1, 10:1, or 5:1.

Additional embodiments of the polymeric bioconjugate comprises one or more repeating units of Formula (VI):

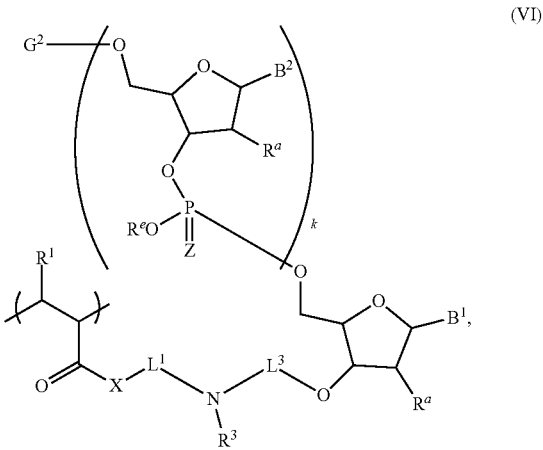
(VI)

wherein X is NR⁴, S, or O; each of $R^1$, $R^3$ and $R^4$ is independently H or $C_1$-$C_6$ alkyl; $L^1$ is a heteroalkylene linker comprising one or more oxygen atoms; $L^3$ is a cleavable heteroalkylene linker where one or more carbon atoms is replaced by O, S, N, C(=O) or C(=S); each of $B^1$ and $B^2$ is independently a nitrogenous base described herein; $G^2$ is a 5' hydroxyl blocking group described herein; and each $R^a$ is independently H, —OH, halogen, —O—($C_1$-$C_6$ alkyl), —O—($C_1$-$C_6$ haloalkyl), or —OY, where Y is a 2' hydroxyl protecting group; $R^e$ is unsubstituted $C_1$-$C_6$ alkyl or substituted $C_1$-$C_6$ alkyl; Z is O or S; and k is an integer from 1 to 500. In some such embodiments, $L^1$ comprises 3 to 5000 membered heteroalkylene. In some such embodiments, the non-limiting members of $L^1$ comprise carbon (C) and oxygen (O). In some embodiments, the moieties of $L^1$ comprise a functional group, nonlimiting examples of which include hydroxyl, alkoxy, ether, and carbonyl. In some embodiments, the moieties of $L^1$ increase the water solubility of the polymer. In some embodiments, $R^1$ and $R^3$ are H. In some such embodiments, $R^e$ is substituted $C_1$-$C_6$ alkyl. A nonlimiting example of a substituted $C_1$-$C_6$ alkyl suitable for use as $R^e$ includes —CH₂CH₂CN. In other embodiments, the polymeric bioconjugate comprises a repeating unit of Formula (VI) that is also represented by Formula (VIa):

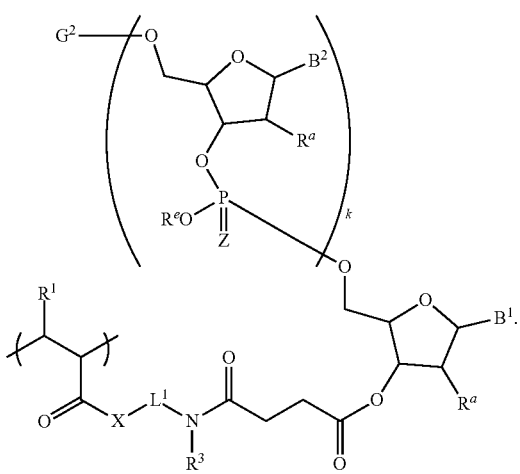

(VIa)

In some embodiments, the polymeric bioconjugate comprises one or more acrylamide or acrylate repeating units of Formula (II):

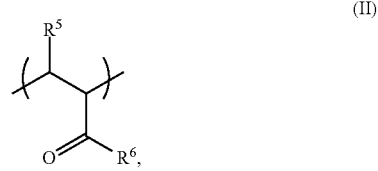

(II)

wherein $R^5$ is H or $C_1$-$C_6$ alkyl; $R^6$ is —NR⁷R⁸ or —O-$L^2$-R⁹; each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and $L^2$ is a heteroalkylene linker comprising one or more oxygen atoms. In some such embodiments, the molar ratio of repeating units of Formula (VI) (including Formula (VIa)) to the repeating units of formula (II) (including Formula (IIa) or (IIb)) is from about 1:200 to 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, from about 5:1 to about 1:5, from about 4:1 to about 1:4, from about 3:1 to about 1:3, from about 2:1 to about 1:2; or about 1:1. In some embodiments, the polymeric bioconjugate comprises the structure:

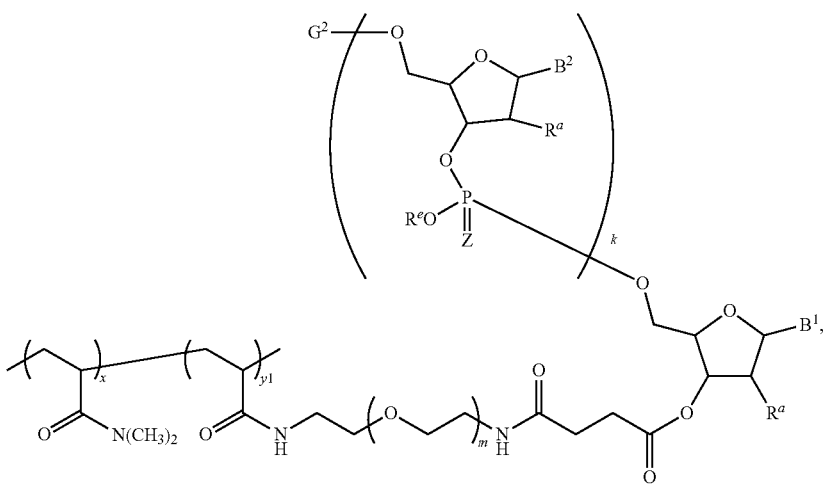

(VIa-1)

-continued

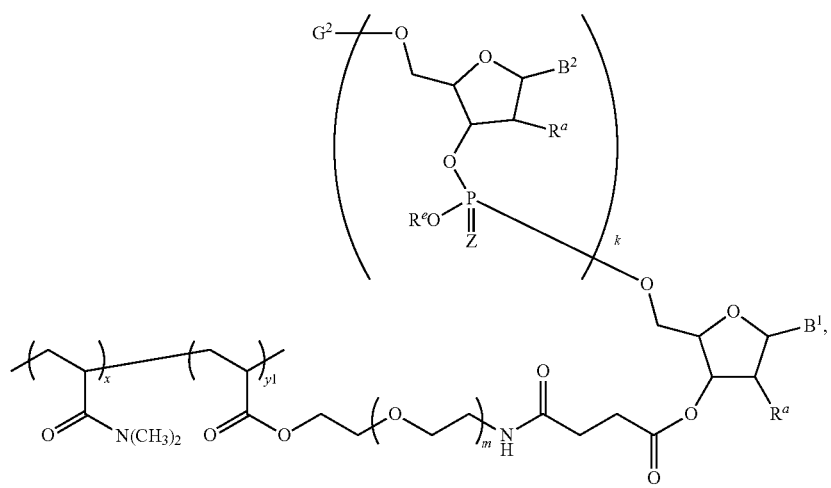

(VIa-2)

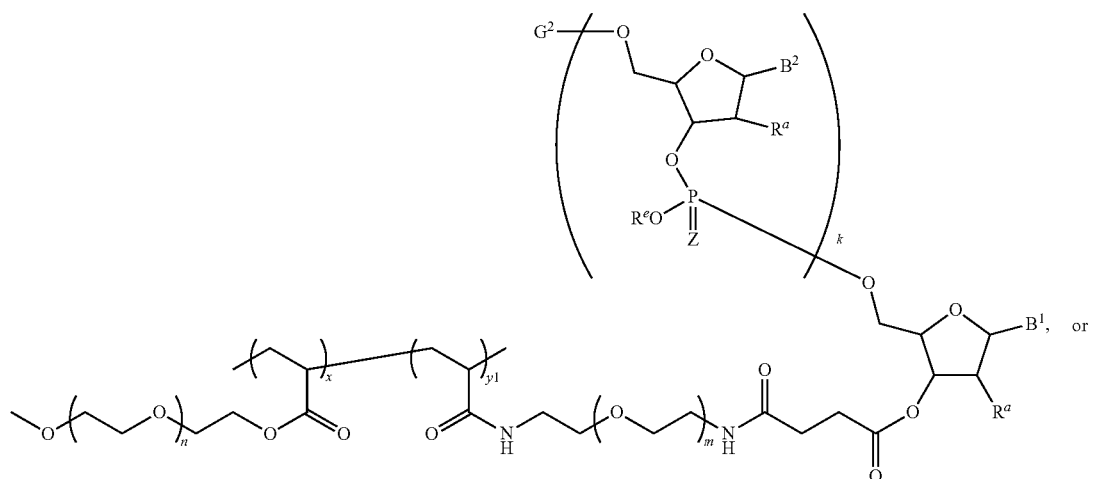

(VIa-3)

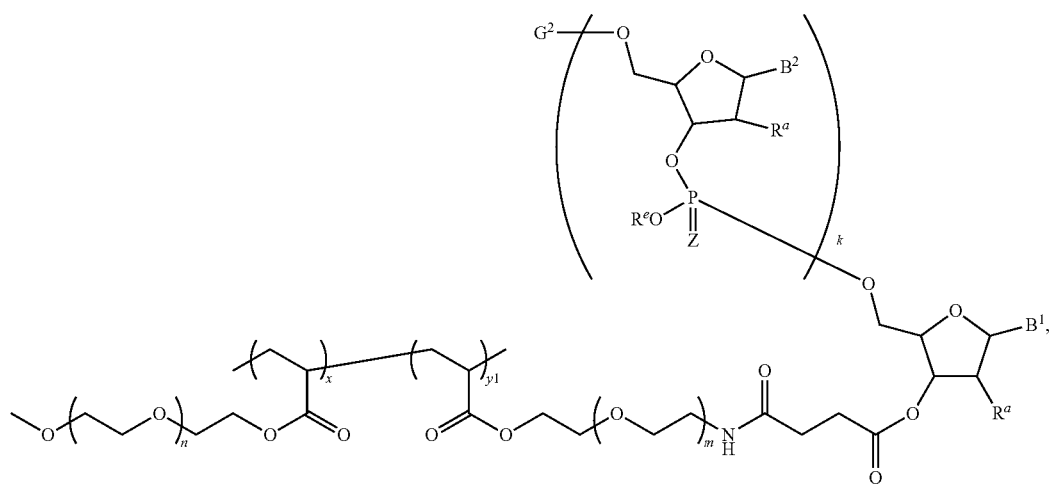

(VIa-4)

wherein each of m and n is independently an integer from about 2 to 200; each of m and n is independently an integer from about 2 to 200; and each of and each of x and $y^1$ is independently an integer from 1 to 50,000. In further embodiments, m is 5, 10, 20, 30, 40, 50, 60, 70, 80, 90, 100, 110, 120, 130, 140, 150, 160, 170, 180, 190, or 200. In further embodiments, n is 5, 10, 20, 30, 40, 50, 60, 70, 80, 90, 100, 110, 120, 130, 140, 150, 160, 170, 180, 190, or 200. In further embodiments, x is 5, 100, 500, 1,000, 2,000, 5,000, 10,000, 15,000, 20,000, 25,000, 30,000, 35,000, 40,000, 45,000, or 50,000. In further embodiments, $y^1$ is 5, 100, 500, 1,000, 2,000, 5,000, 10,000, 15,000, 20,000, 25,000, 30,000, 35,000, 40,000, 45,000, or 50,000. In some such embodiments, the polymeric bioconjugate includes a ratio of x to $y^1$ from about 50:1 to about 5:1. In some embodiments, ratio of x to $y^1$ is about 50:1, 45:1, 40:1, 35:1, 30:1, 25:1, 20:1, 15:1, 10:1, or 5:1.

In any embodiments of the polymeric bioconjugates described herein, the bioconjugate may further comprises one or more repeating units of the structure:

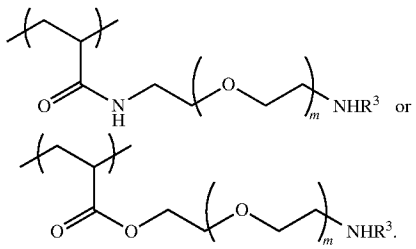

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

General Procedure for DMT Loading Measurement

An UV/Vis spectrophotometric method is used to determine the DMT loading (µmol/g) of a 5'-DMT protected nucleotide conjugated on a Polyvalent Hub (PVH). The sample is dissolved in acetonitrile (AcN) containing toluenesulfonic acid (TSA). The acid cleaves off the DMT protective group and its loading is quantitatively are determined. Agilent 8453 UV-Visible spectrophotometer, Agilent UV-Visible ChemStation software Rev. A.10.0, and Agilent UV-Visible rectangular cell 10 mm, 3.5 mL (P/N 5061-3387) are used for the measurement.

- A master batch of TSA solution in AcN is prepared by dissolving 8.0 g of TSA in 500 mL of HPLC grade AcN. The resulting solution is stable under ambient temperature for 4 weeks.
- Launch the Agilent UV-Visible ChemStation software and select Fixed Wavelength(s) of 498 nm.
- Acquire a blank spectrum using the TSA/AcN solution.
- Accurately weigh out 20.0-26.0 mg of the nucleotide-conjugated PVH sample and transfer it into 100 mL of TSA/AcN solution.
- Vortex for 2 minutes and allow any insoluble materials settle to the bottom in 10-15 minutes.
- Transfer the supernatant to a dry cuvette (Agilent UV-Visible rectangular cell 10 mm, 3.5 mL).
- Scan the sample solution and take the absorbance value at 498 nm.

DMT loading on the CPG support is determined using the following equation:

$$\text{Loading } (\mu\text{mole/gram}) = \frac{\text{Absorbance (498 nm)} \times \text{Sample Volume (mL)}}{76.5 \ (\text{mL} * \text{cm}^{-1} * \mu\text{mole}^{-1}) \times \text{Sample Weight (g)}}$$

Use the 5-digit number from the 498 nm Absorbance value.
Sample Volume is 100 mL.
The extinction coefficient ε for DMT is estimated 76.5 mL/cm*µmole.
Convert sample weight from mg to gram.

Example 1. Preparation of poly(NH$_2$-PEG-co-DMA) having 1.25 mol % of NH$_2$-PEG

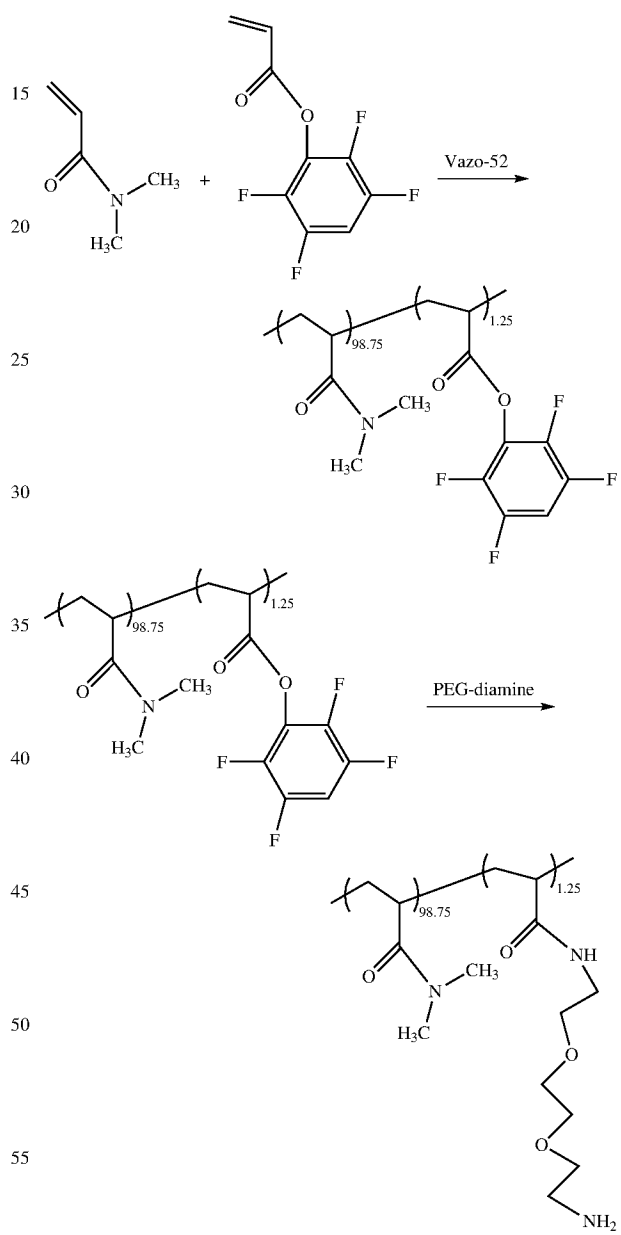

Into a 250-mL three-necked round bottom flask containing 80 mL of dry acetonitrile (ACN), 5.16 g (52.05 mmol) of N,N-dimethylacrylamide (DMA) and 0.167 g (0.758 mmol) of 2,3,5,6-tetrafluorophenyl acrylate (TFPA) were dissolved. The mixture was bubbling with ultra-pure argon at 50 ml/min for 75 minutes under constant stirring. To this deoxygenated solution 26.5 mg (0.116 mmol) of Vazo-52 was added and the polymerization was conducted at 55±2°

C. for 21 hours under ultra-pure argon with flow rate of 20 mL/min. The reaction was cooled to ambient temperature. The ACN was removed under reduced pressure and the residue re-dissolved in 30 mL of methylethyl ketone (MEK) at ambient temperature. The polymer was precipitated by adding the MEK solution into 800 mL of anhydrous n-hexane to provide 4.50 g (84% yield) of poly(TFPA-co-DMA). $^1$H-NMR integration indicated that the copolymer contained 1.25 mol % of TFPA, and GPC Light Scattering gave Mw of 66.8 KDa. The numbers 98.75 and 1.25 for the DMA repeating unit and the TFPA repeating unit of the copolymer refer to monomer ratio of DMA and TFPA (i.e., the DMA is about 98.75 mol % and TFPA is about 1.25 mol %).

Figure 2A:
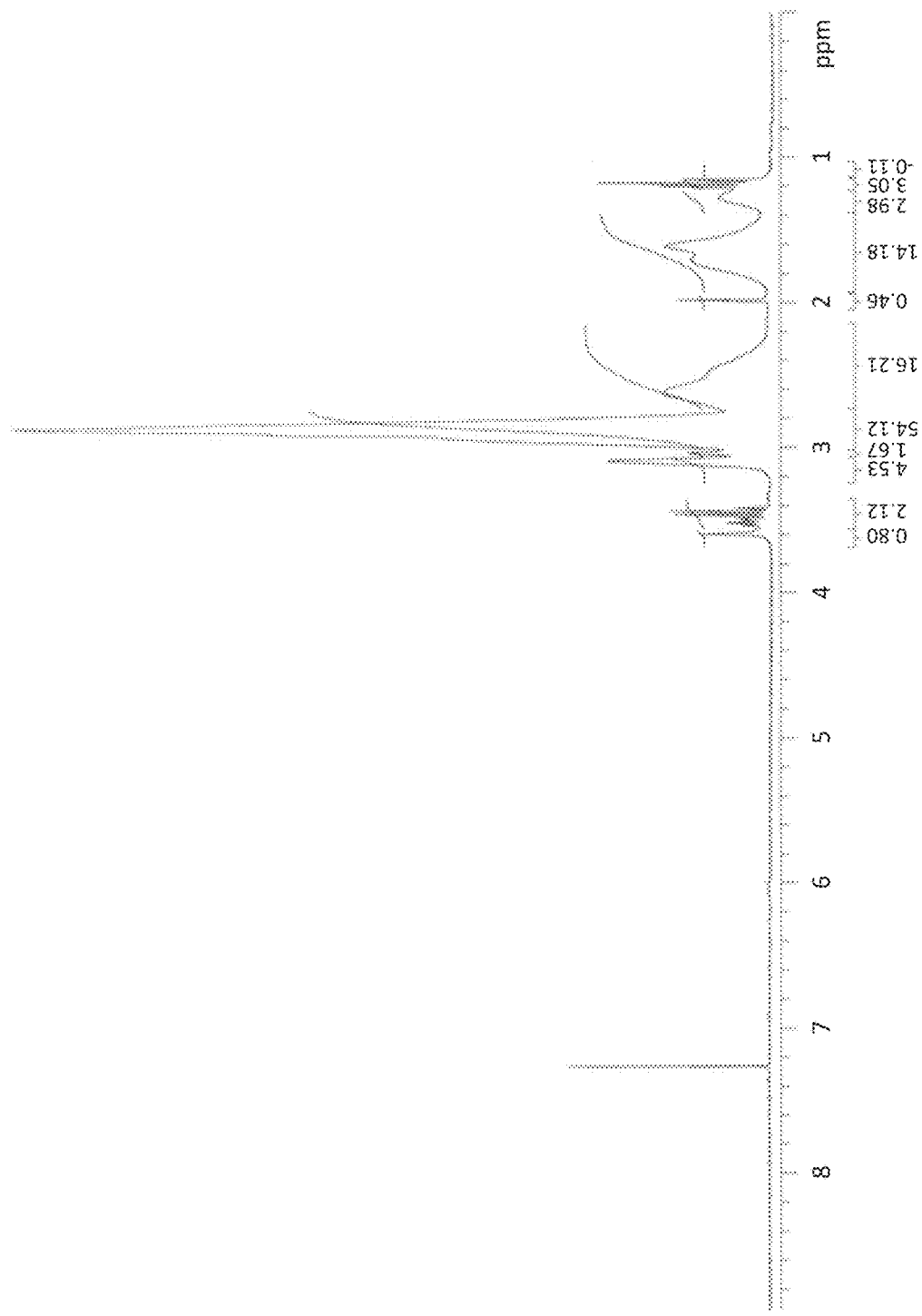
FIG. 2A is a $^1$H NMR spectrum measured in $CDCl_3$ of a poly($NH_2$-PEG-co-DMA) with 1.25 mol % of amino-PEG pendants according to an embodiment of the present application.

Into 10 mL of dry ACN, 1.0 g of the above poly(TFPA-co-DMA), 214 mg of 2,2-(ethylenedioxy)bis(ethylamine) and 297.0 mg of triethylamine were dissolved. The resulting solution was vortexed overnight at ambient temperature. The reaction product was precipitated in diethyl ether to provide dimethylacrylamide copolymer having amino-PEG pendants, i.e., poly(NH$_2$-PEG-co-DMA). $^1$H-NMR integration indicated that the copolymer contained 1.25 mol % of amino-PEG pendants (see FIG. 2A).

Example 2. Conjugation of DMT-dT-3'-succinate onto poly(NH$_2$-PEG-co-DMA) (1.25 mol %)

Figure 2B:
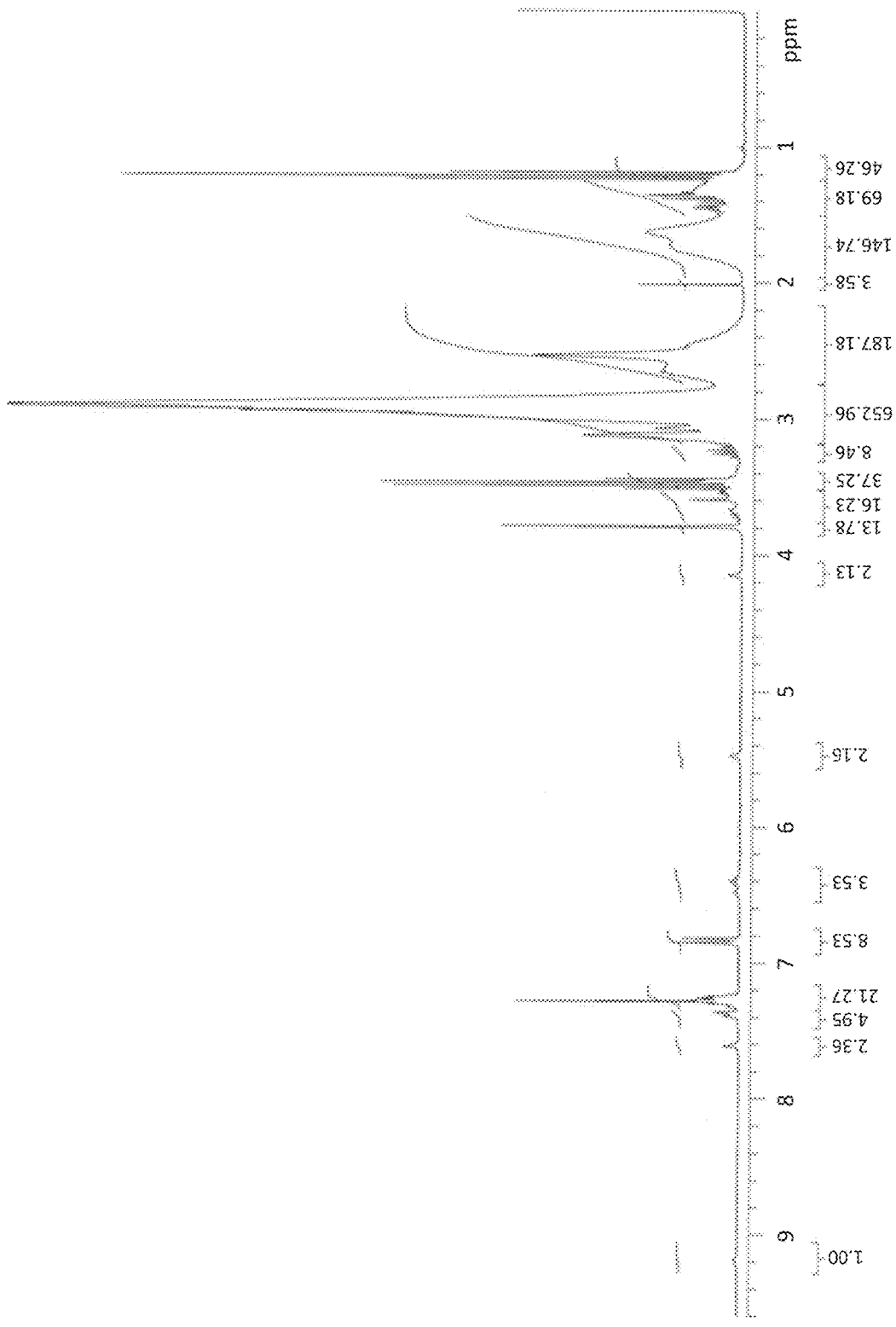
FIG. 2B is a $^1$H NMR spectrum measured in $CDCl_3$ of a DMT-dT conjugated poly($NH_2$-PEG-co-DMA) with 1.25 mol % of amino-PEG pendant according to an embodiment of the present application.

Into 4 mL acetonitrile, 200 mg of poly(NH$_2$-PEG-co-DMA) prepared in Example 1, 37 mg DMT-dT-3'-succinate TEA salt, 20.8 mg HBTU, and 9.7 mg diisopropylethylamine were dissolved. The resulting solution was vortexed overnight at ambient temperature. The reaction product was precipitated in diethyl ether to provide 190 mg (88% yield) of dT-3'-succinate conjugated copolymer comprising a 5'-DMT protective group, i.e., DMT-dT-3'-succinate conjugated poly(—NH$_2$-PEG-co-DMA) (see FIG. 2B). GPC (RID) gave Mw of 105 KDa.

Example 3. Preparation of poly(NH$_2$-PEG-co-DMA) having 5 mol % of NH$_2$-PEG

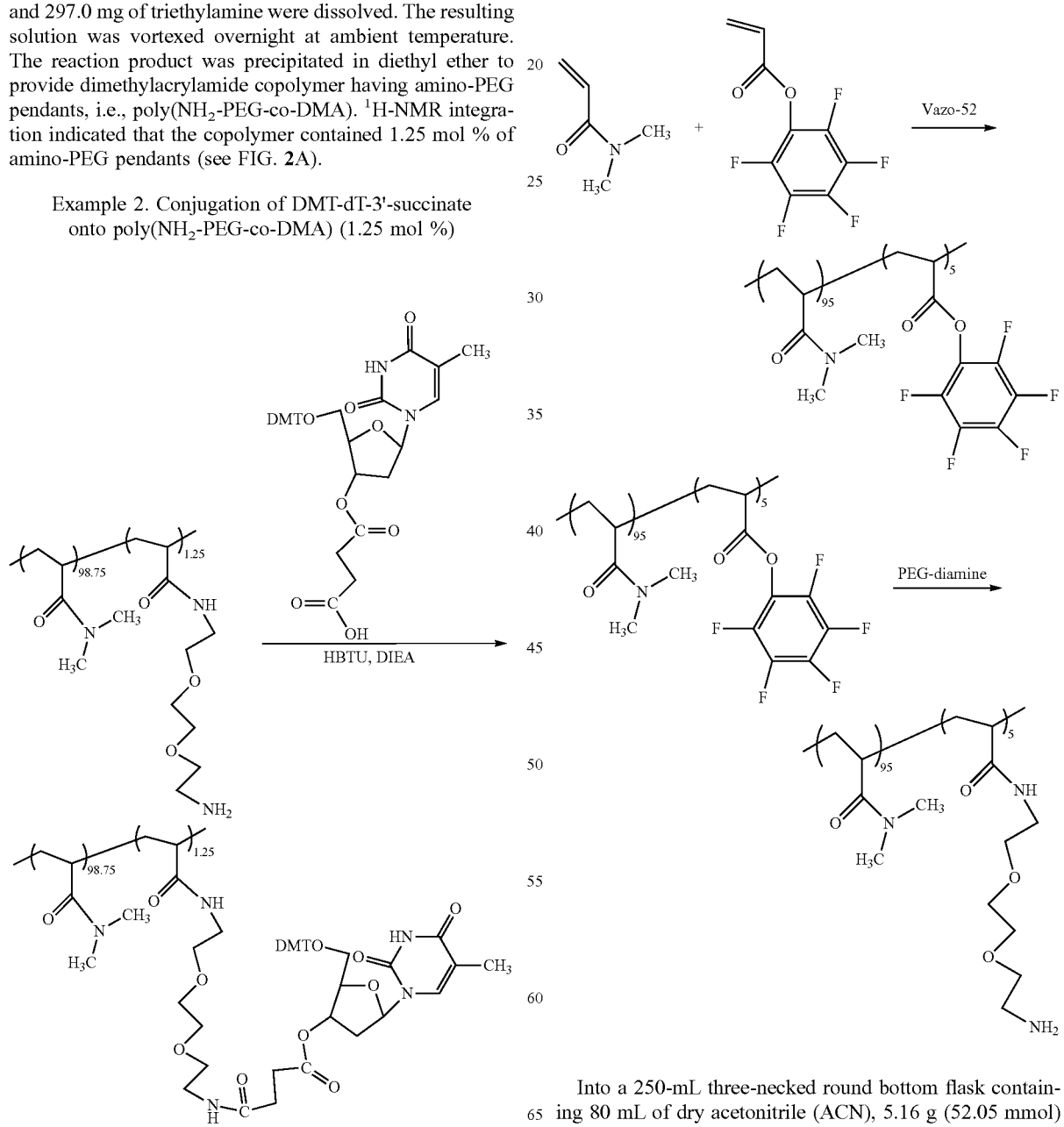

Into a 250-mL three-necked round bottom flask containing 80 mL of dry acetonitrile (ACN), 5.16 g (52.05 mmol) of N,N-dimethylacrylamide (DMA) and 0.652 g (3.03 mmol) of 2,3,5,6-pentafluorophenyl acrylate (PFPA) were dissolved. The mixture was bubbling with ultra-pure argon at 50 ml/min for 75 minutes under constant stirring. To this deoxygenated solution 27.3 mg (0.120 mmol) of Vazo-52 was added and the polymerization was conducted at 55±2° C. for 21 hours under ultra-pure argon with flow rate of 20 mL/min. The reaction was cooled to ambient temperature. The ACN was removed under reduced pressure and the residue re-dissolved in 30 mL of methylethyl ketone (MEK) at ambient temperature. The mixture was precipitated by adding the MEK solution into 800 mL of anhydrous n-hexane to provide 2.5 g (43% yield) of poly(DMA-co-PFPA), $^1$H-NMR integration indicated 5 mol % of PFPA in the copolymer. The numbers 95 and 5 for the DMA repeating unit and the TFPA repeating unit of the copolymer refer to monomer ratio of DMA and TFPA (i.e., the DMA is about 95 mol % and TFPA is about 5 mol %).

Into 10 mL of dry ACN, 1.0 g of the above poly(DMA-co-PFPA), 1.07 g of 2,2-(ethylenedioxy)bis(ethylamine) 1.54 g of triethylamine were dissolved. The resulting solution was vortexed overnight at ambient temperature. The reaction product was precipitated in diethyl ether to provide poly(NH$_2$-PEG-co-DMA) having about 5 mol % amino-PEG pendants.

Example 4. Conjugation of DMT-dT-3'-succinate onto poly(NH$_2$-PEG-co-DMA) (5 mol % NH$_2$-PEG)

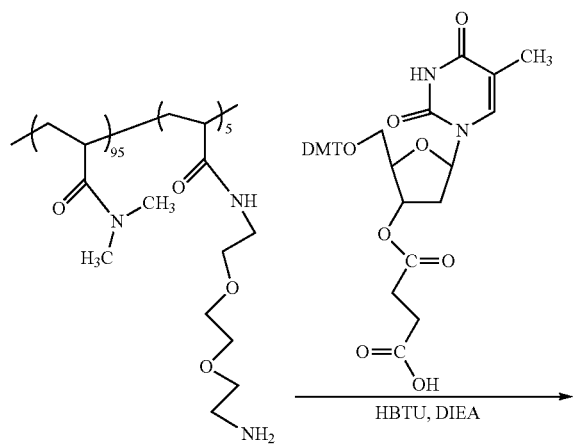

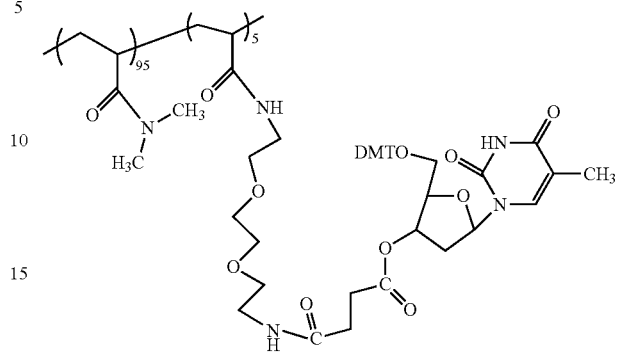

Into 4 mL acetonitrile, 200 mg poly(NH$_2$-PEG-co-DMA) prepared in Example 3, 135 mg DMT-dT-3'-succinate TEA salt, 104 mg HBTU, and 27 mg diisopropylethylamine were dissolved. The resulting solution was vortexed overnight at ambient temperature. The reaction product was precipitated in diethyl ether to provide 250 mg (96% yield) of DMT-dT-3'-succinate conjugated poly(NH$_2$-PEG-co-DMA). The numbers 95 and 5 for the DMA repeating unit and the PEG-NH$_2$ repeating unit of the copolymer refer to monomer ratio of DMA and PEG-NH$_2$ (i.e., the DMA is about 95 mol % and PEG-NH$_2$ is about 5 mol %). FIG. 3A illustrate $^1$H NMR spectra taken in chloroform-d1 for the DMT-dT conjugated poly(NH$_2$-PEG-co-DMA).

Example 5. Preparation of DMT-dTdTdT-3'-succinate Conjugated poly(NH$_2$-PEG-co-DMA)

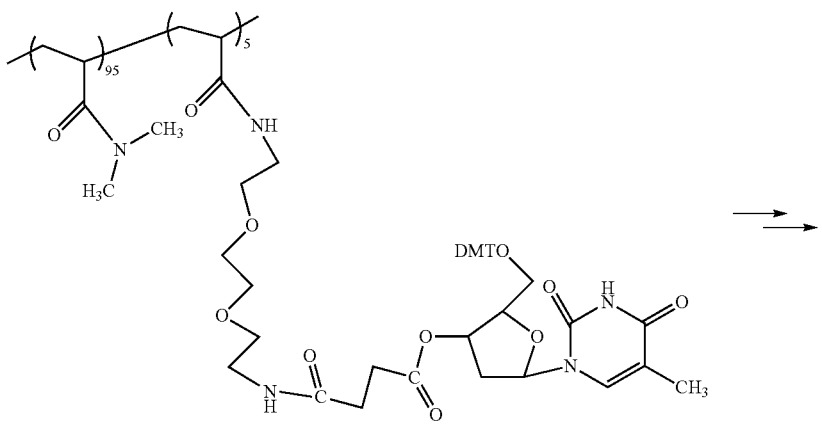

-continued

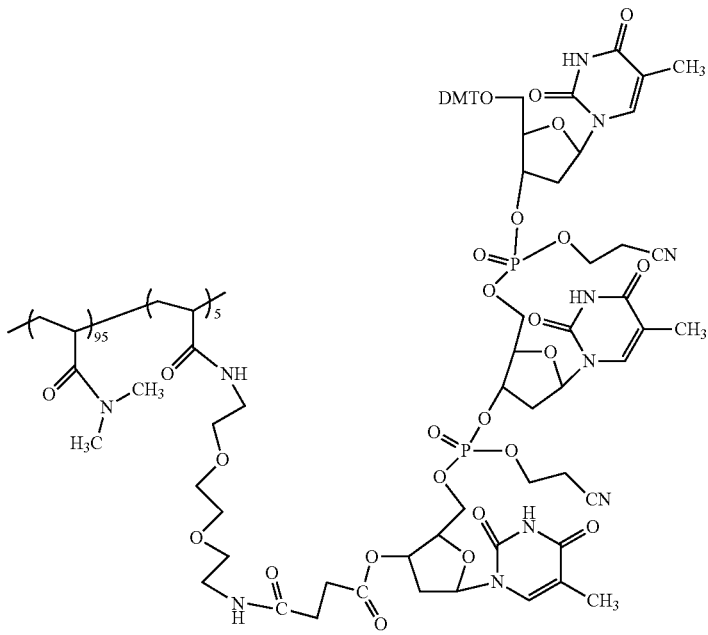

Deprotection: A mixture of 100 mg of DMT-dT-3'-succinate conjugated poly(NH$_2$-PEG-co-DMA) prepared in Example 4, 150.6 mg of trichloroacetic acid (TCA), 64.3 mg of triethyl silane (TES), and 297 µL of dichloromethane (DCM) was shaken for about 10 minutes at ambient temperature. The reaction product was then precipitated in diethyl ether to provide the deprotected dT-3'-succinate conjugated poly(NH$_2$-PEG-co-DMA). Coupling and oxidation: To the deprotected bioconjugate was added 1.7 mL of 0.25 M 5-(ethylthio)tetrazole (ETT) solution (55 mg) and 91.9 mg of DMT-dT phosphoramidite under stirring. After 60 mins of constant stirring, 32 mg of 3-chloroperbenzoic acid (mCPBA) was added as a powder. The mixture was further stirred for another 10 mins. The solution was precipitated by diethyl ether to provide the DMT protected bioconjugate having two dT nucleobases DMT-dTdT-3'-succinate conjugated poly(NH$_2$-PEG-co-DMA). The deprotection procedure using TCA and TES was repeated on DMT-dTdT-3'-succinate conjugated poly(NH$_2$-PEG-co-DMA) to provide the deprotected bioconjugate having two dT nucleobases dTdT-3'-succinate conjugated poly(NH$_2$-PEG-co-DMA). Another cycle of coupling and oxidation as described herein provided the DMT protected bioconjugate having three dT nucleobases DMT-dTdTdT-3'-succinate conjugated poly(NH$_2$-PEG-co-DMA) with DMT loading of 135 µmol/g.

Figure 3B:
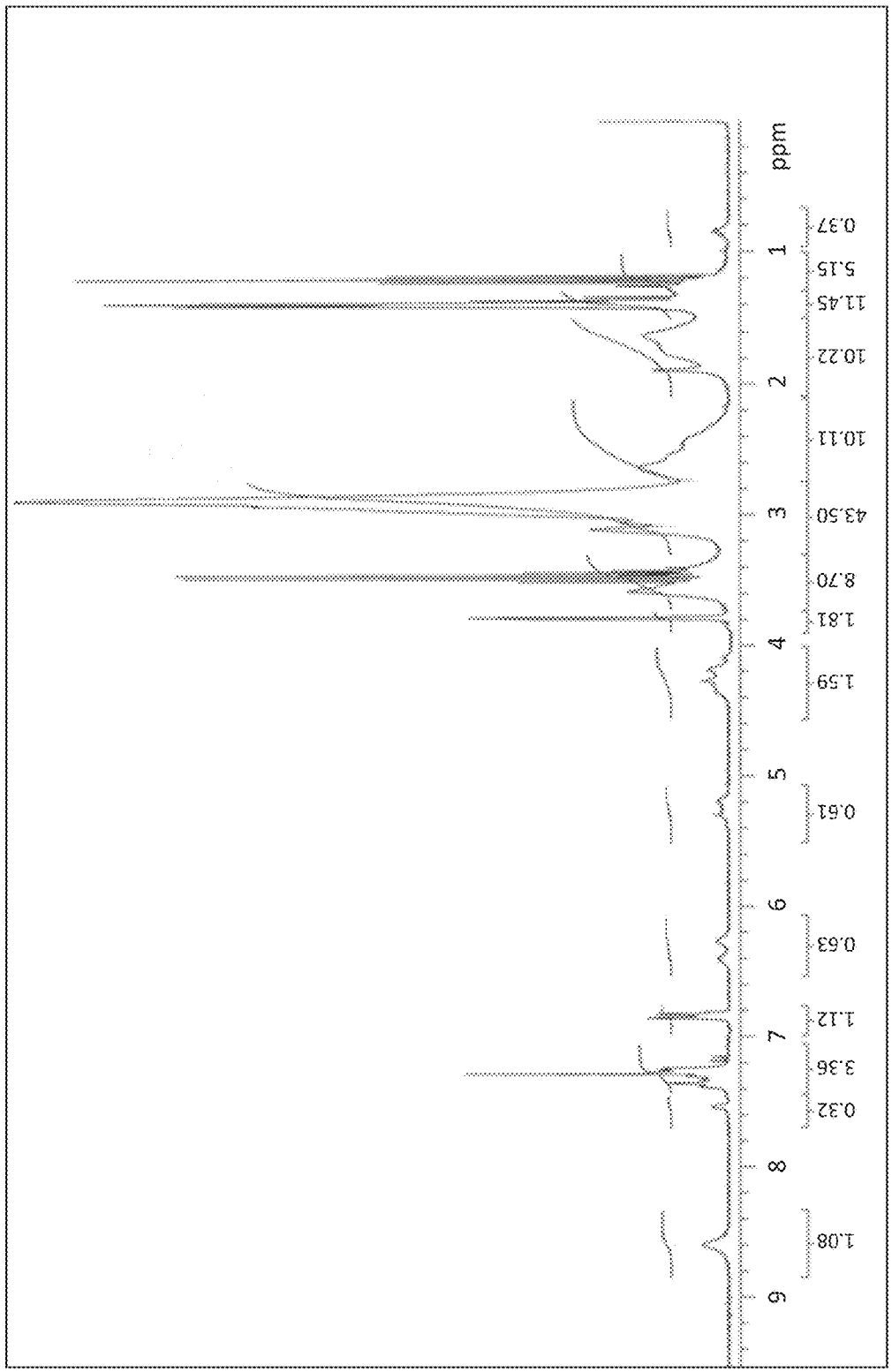
FIG. 3B is a $^1$H NMR spectrum measured in $CDCl_3$ of a DMT-dT-dT conjugated poly($NH_2$-PEG-co-DMA) with 5 mol % of amino-PEG pendant according to an embodiment of the present application.
Figure 3C:
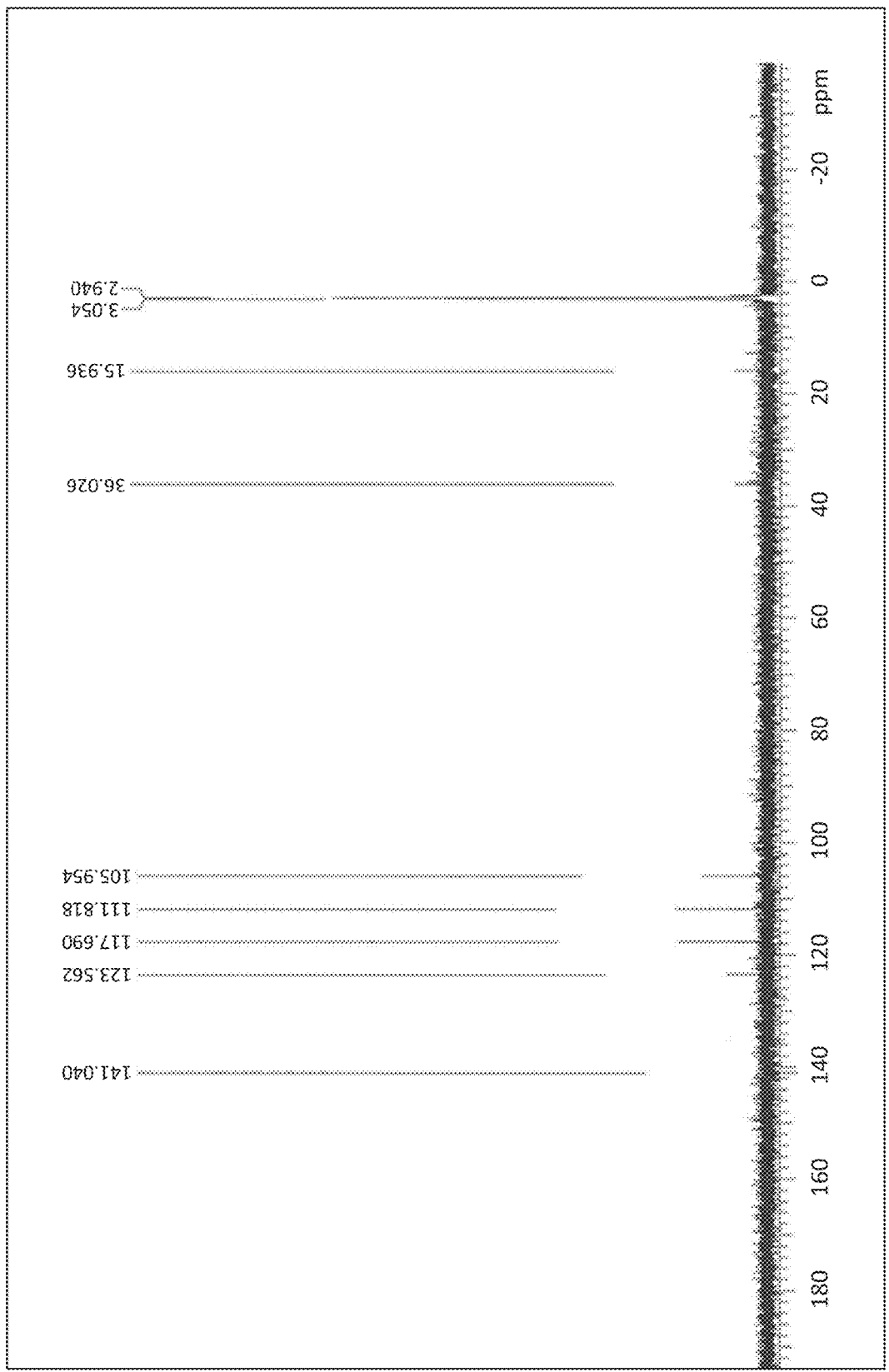
FIG. 3C is a $^{31}$P NMR spectrum measured in $CDCl_3$ of a DMT-dT-dT conjugated poly($NH_2$-PEG-co-DMA) with 5 mol % of amino-PEG pendant according to an embodiment of the present application.
Figure 3D:
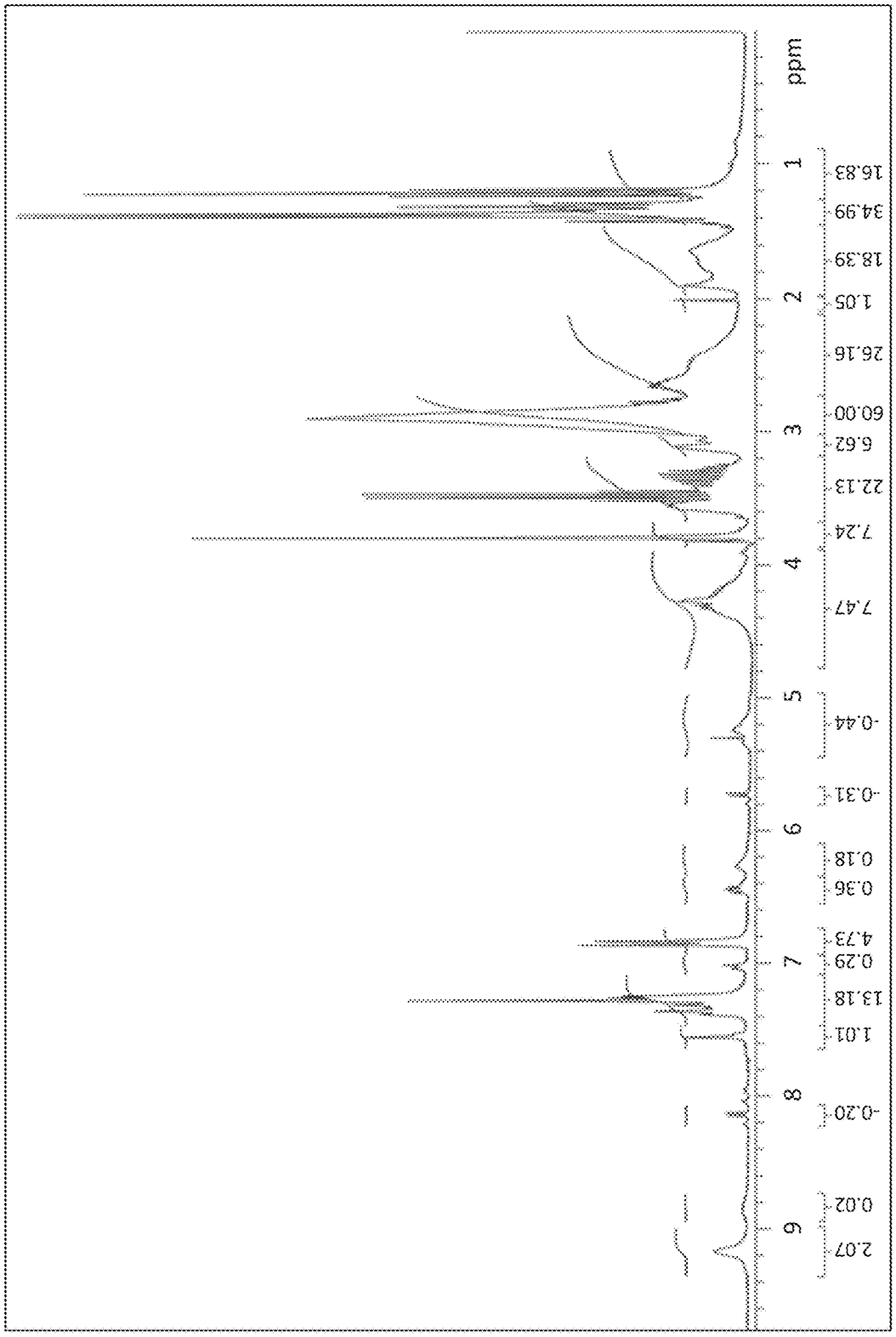
FIG. 3D is a $^1$H NMR spectrum measured in $CDCl_3$ of a DMT-dTdTdT conjugated poly($NH_2$-PEG-co-DMA) with 5 mol % of amino-PEG pendant according to an embodiment of the present application.
Figure 3E:
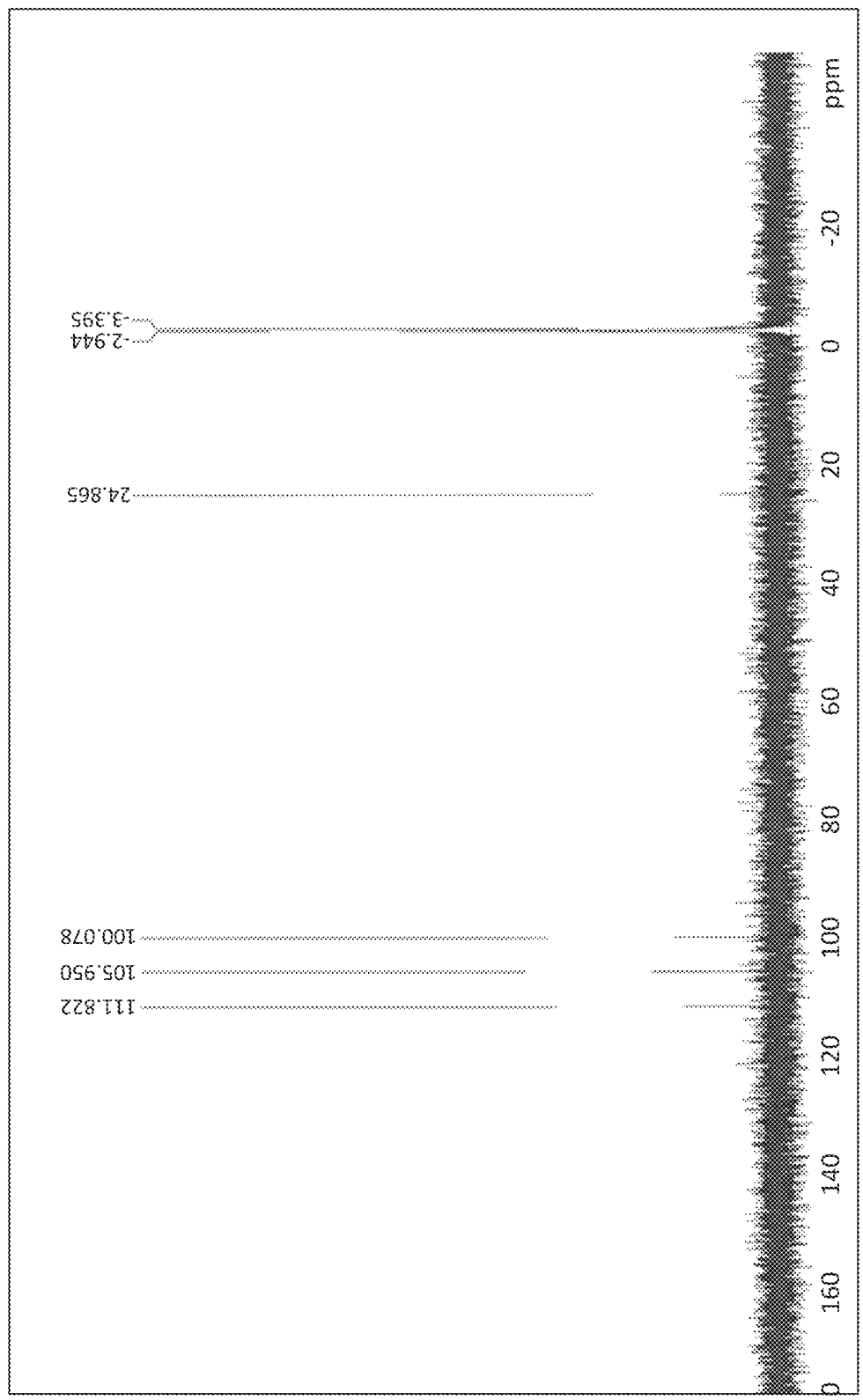
FIG. 3E is a $^{31}$P NMR spectrum measured in $CDCl_3$ of a DMT-dTdTdT conjugated poly($NH_2$-PEG-co-DMA) with 5 mol % of amino-PEG pendant according to an embodiment of the present application.

FIGS. 3B and 3C illustrate $^1$H and $^{31}$P NMR spectrum taken in chloroform-d1 of the DMT-dTdT conjugated poly(NH$_2$-PEG-co-DMA) prepared in Example 5. FIGS. 3D and 3E illustrate $^1$H and $^{31}$P NMR spectrum taken in chloroform-d1 of the DMT-dTdTdT conjugated poly(NH$_2$-PEG-co-DMA) prepared in Example 5.

Example 6. Preparation of poly(NH$_2$-PEG$_{3.4k}$ acrylate-co-MeO-PEG)

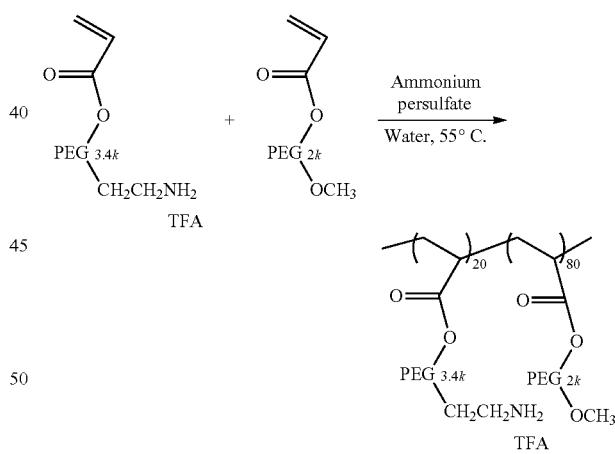

Into a 100-mL three-necked round bottom flask containing 40 mL dry acetonitrile (ACN), 0.213 g (0.063 mmol) of acrylate-PEG-amine and 0.5 g (0.147 mmol) methoxypoly (ethylene glycol) were dissolved. The mixture was bubbling with ultra-pure argon at 50 ml/min for 75 minutes under constant stirring. To this deoxygenated solution 10 mg (0.044 mmol) of ammonium persulfate was added and the polymerization was conducted at 55±2° C. for 21 hours under ultra-pure argon with flow rate of 20 mL/min. The reaction was cooled to ambient temperature. The mixture was collected and dialysis (MWCO 10 KDa) against water. The solution was then lyophilized to provide 384 mg (yield of 54%) poly(NH$_2$-PEG$_{3.4k}$ acrylate-co-MeO-PEG). The numbers 20 and 80 for the $NH_2$-$PEG_{3.4k}$ acrylate repeating unit and the PEG-MeO repeating unit of the copolymer refer to monomer ratio of $NH_2$-$PEG_{3.4k}$ acrylate and PEG-MeO (i.e., $NH_2$-$PEG_{3.4k}$ acrylate is about 20 mol % and PEG-MeO is about 80 mol %).

Example 7. Conjugation of DMT-dT-3'-succinate onto poly($NH_2$-$PEG_{3.4k}$ acrylate-co-MeO-PEG)

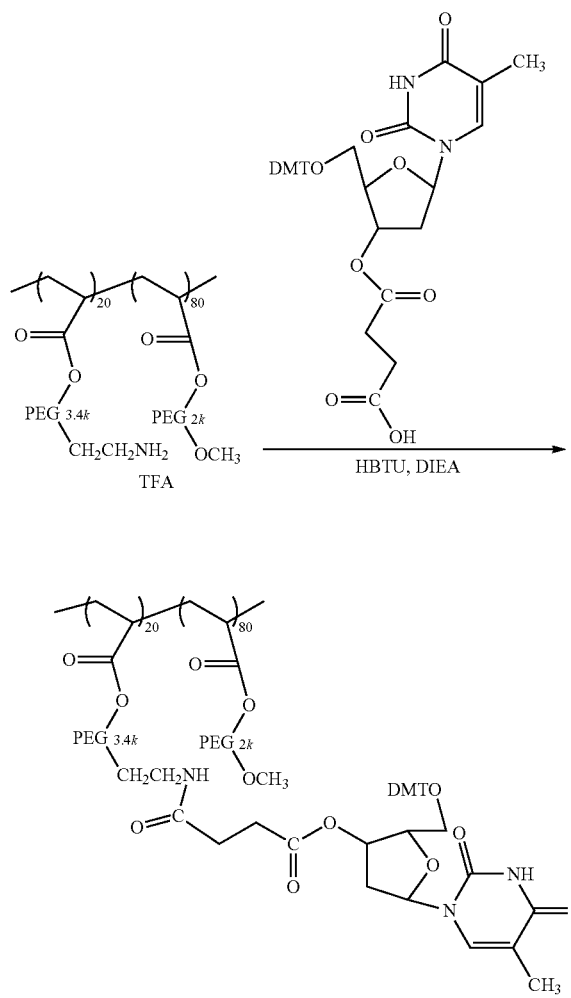

Figure 4:
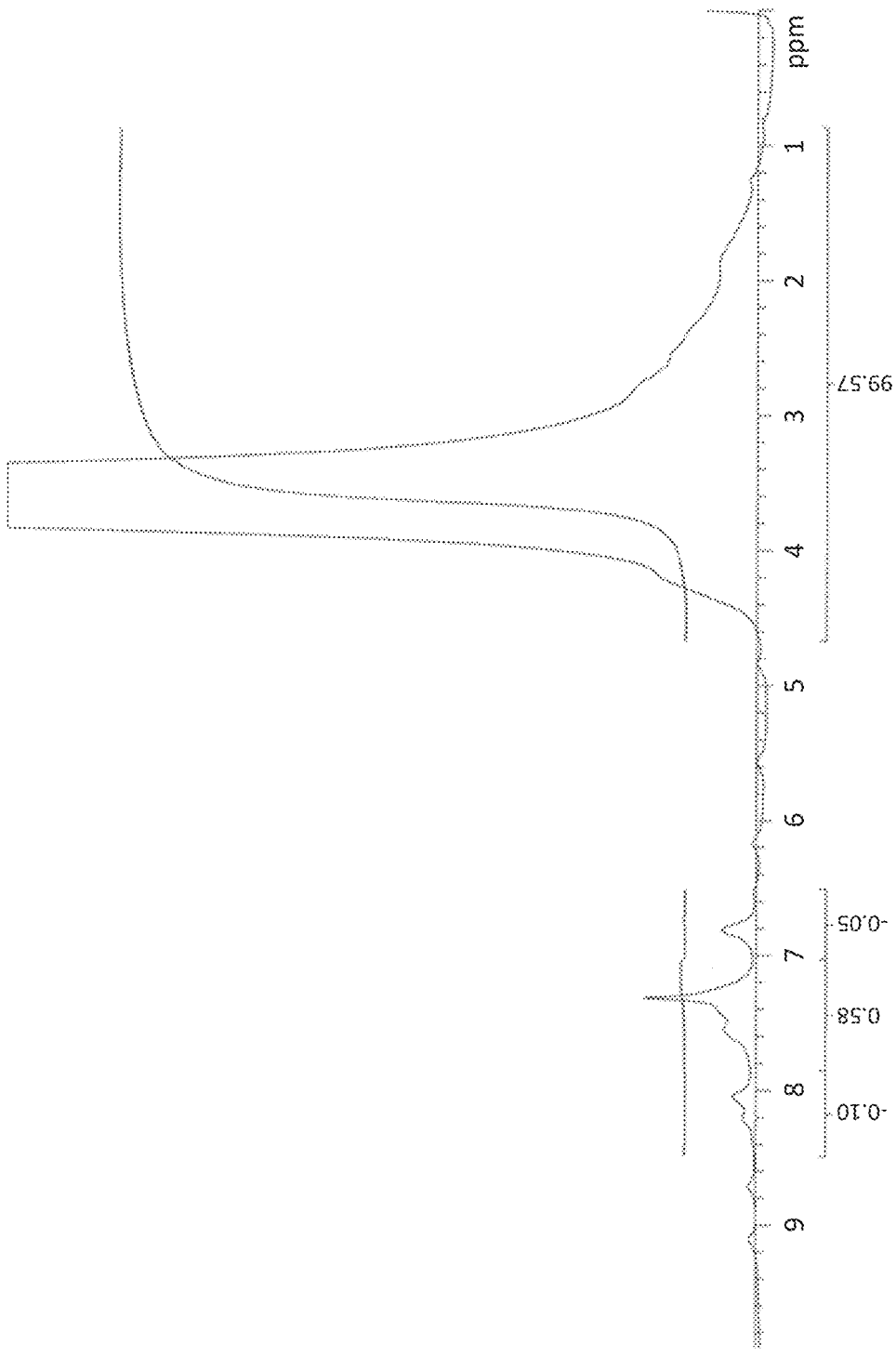
FIG. 4 is a $^1$H NMR spectrum of a DMT-dT conjugated poly($NH_2$-$PEG_{3.4k}$ acrylate-co-MeO-PEG) copolymer according to an embodiment of the present application.

Into 2 mL of acetonitrile, 250 mg poly($NH_2$-$PEG_{3.4k}$ acrylate-co-MeO-PEG) prepared in Example 6, 32.7 mg DMT-dT-3'-succinate TEA salt, 18.3 mg HBTU and 11.4 mg diisopropylethylamine were dissolved. The resulting solution was vortexed (200 RPM) overnight at ambient temperature. The reaction product was precipitated in diethyl ether to provide the DMT protected bioconjugate having a 5'-DMT protective group: DMT-dT-3'-succinate conjugated poly($NH_2$-$PEG_{3.4k}$ acrylate-co-MeO-PEG). FIG. 4 illustrates the $^1$H NMR spectrum of the DMT-dT conjugated poly($NH_2$-$PEG_{3.4k}$ acrylate-co-MeO-PEG) prepared in Example 7.

Example 8. Preparation of poly($NH_2$-$PEG_{3.4k}$ acrylate) Homopolymer

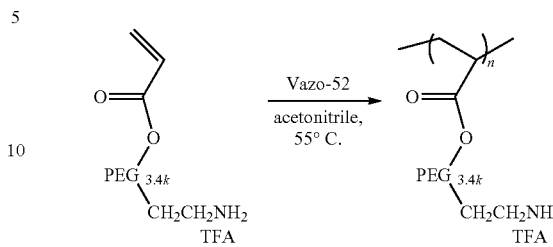

Into a 100-mL three-necked round bottom flask containing 40 mL of dry acetonitrile (ACN), 1 g (0.294 mmol) of acrylate-PEG-amine was dissolved. The mixture was bubbling with ultra-pure argon at 50 ml/min for 75 minutes under constant stirring. To this deoxygenated solution 96 mg (0.42 mmol) of Vazo-52 was added and the polymerization was conducted at 55±2° C. for 21 hours under ultra-pure argon with flow rate of 20 mL/min. The reaction was cooled to ambient temperature. The reaction product was precipitated in diethyl ether to provide 900 mg (yield of 90%) poly($NH_2$-$PEG_{3.4k}$ acrylate) homopolymer.

Example 9. Conjugation of DMT-dT-3'-succinate onto poly($NH_2$-$PEG_{3.4k}$ acrylate) Homopolymer

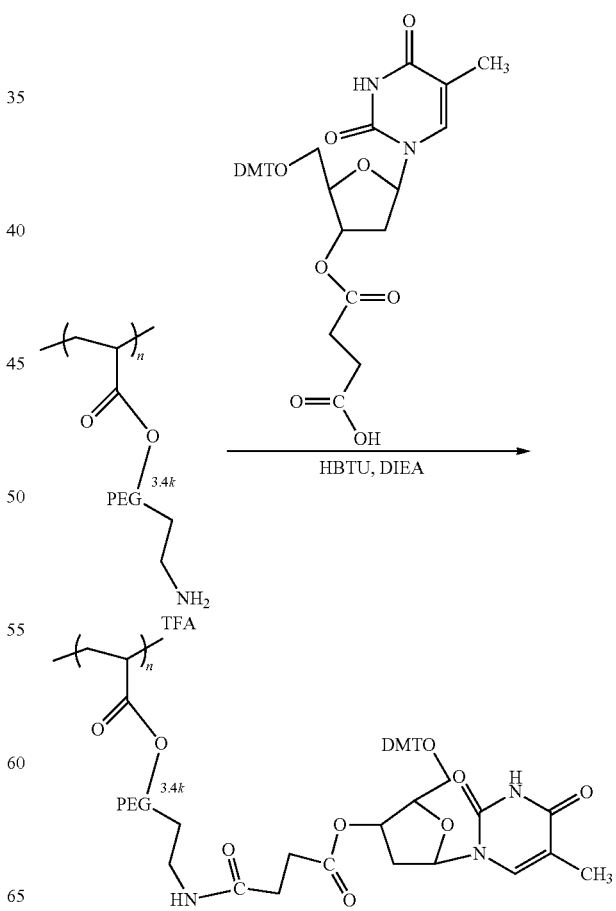

Figure 5A:
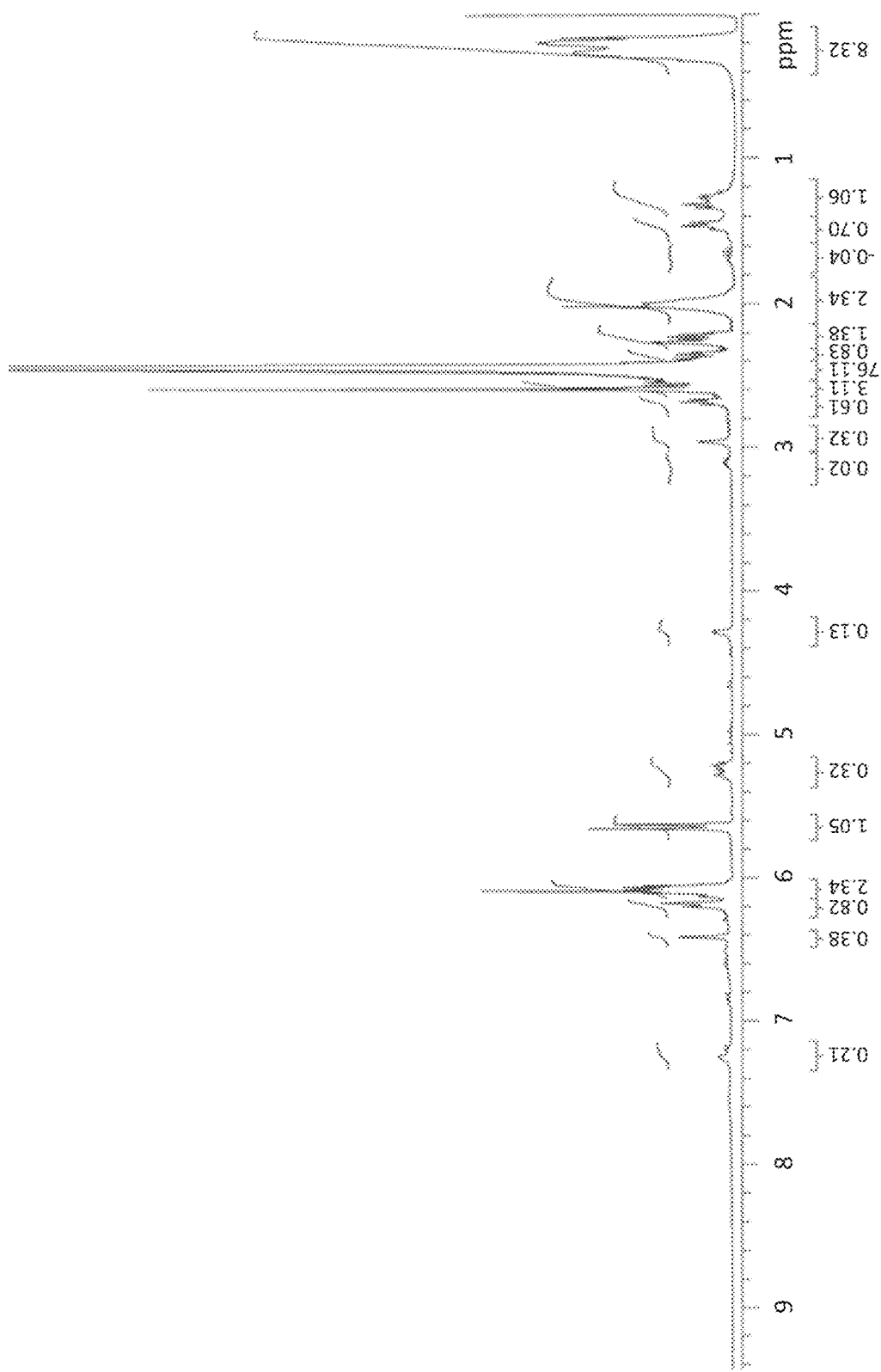
FIG. 5A is a $^1$H NMR spectrum measured in $CDCl_3$ of a poly($NH_2$-$PEG_{3.4k}$ acrylate) homopolymer-dT conjugate according to an embodiment of the present application.

Into 5 mL acetonitrile, 847 mg of poly(NH$_2$-PEG$_{3.4k}$ acrylate) homopolymer prepared in Example 8, 372 mg DMT-dT-3'-succinate TEA salt, 208 mg HBTU and 129 mg diisopropylethylamine were dissolved. The resulting solution was vortexed (200 rpm) overnight at ambient temperature. The reaction product was precipitated in diethyl ether to provide the DMT protected bioconjugate having a 5'-DMT protective group; DMT-dT-3'-succinate conjugated poly(NH$_2$-PEG$_{3.4k}$ acrylate) homopolymer with DMT loading of 235 µmol/g. FIG. 5A illustrates $^1$H NMR spectra taken in acetonitrile-d3 of the DMT-dT conjugated poly(NH$_2$-PEG$_{3.4k}$ acrylate) homopolymer prepared in Example 9.

Example 10. Preparation of DMT-dTdTdT-3'-succinate Conjugated poly(NH$_2$-PEG$_{3.4k}$ Acrylate) Homopolymer

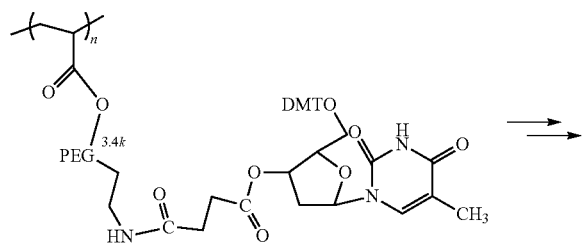

Deprotection: A mixture of 1.06 g of the of DMT-dT-3'-succinate conjugated poly(NH$_2$-PEG$_{3.4k}$ acrylate) homopolymer prepared in Example 9, 1.02 g of trichloroacetic acid (TCA), 434 g of triethyl silane (TES), and 1.7 mL of dichloromethane (DCM) was vortexed at 200 rpm for about 10 minutes at ambient temperature. The reaction product was then precipitated in diethyl ether to provide the deprotected bioconjugate dT-3'-succinate conjugated poly(NH$_2$-PEG$_{3.4k}$ acrylate) homopolymer. Coupling and oxidation: To the deprotected bioconjugate was added 11.9 mL (385 mg) of 0.25 M ETT solution and 620 mg of DMT-dT phosphoramidite under stirring. After 60 mins of constant stirring, 396 mg of 3-chloroperbenzoic acid (mCPBA) was added as a powder. The mixture was further stirred for another 10 minutes at ambient temperature. The solution was precipitated by diethyl ether to provide the DMT protected bioconjugate having two dT nucleobases DMT-dTdT-3'-succinate conjugated poly(NH$_2$-PEG$_{3.4k}$ acrylate) homopolymer with a DMT loading of 305 µmol/g. The deprotection procedure using TCA and TES was repeated to provide the deprotected bioconjugate having two dT nucleobases dTdT-3'-succinate conjugated poly(NH$_2$-PEG$_{3.4k}$ acrylate) homopolymer. Another cycle of coupling and oxidation as described herein provided the DMT protected bioconjugate having three dT nucleobases DMT-dTdTdT-3'-succinate conjugated poly(NH$_2$-PEG$_{3.4k}$ acrylate) homopolymer with DMT loading of 365 µmol/g.

Figure 5B:
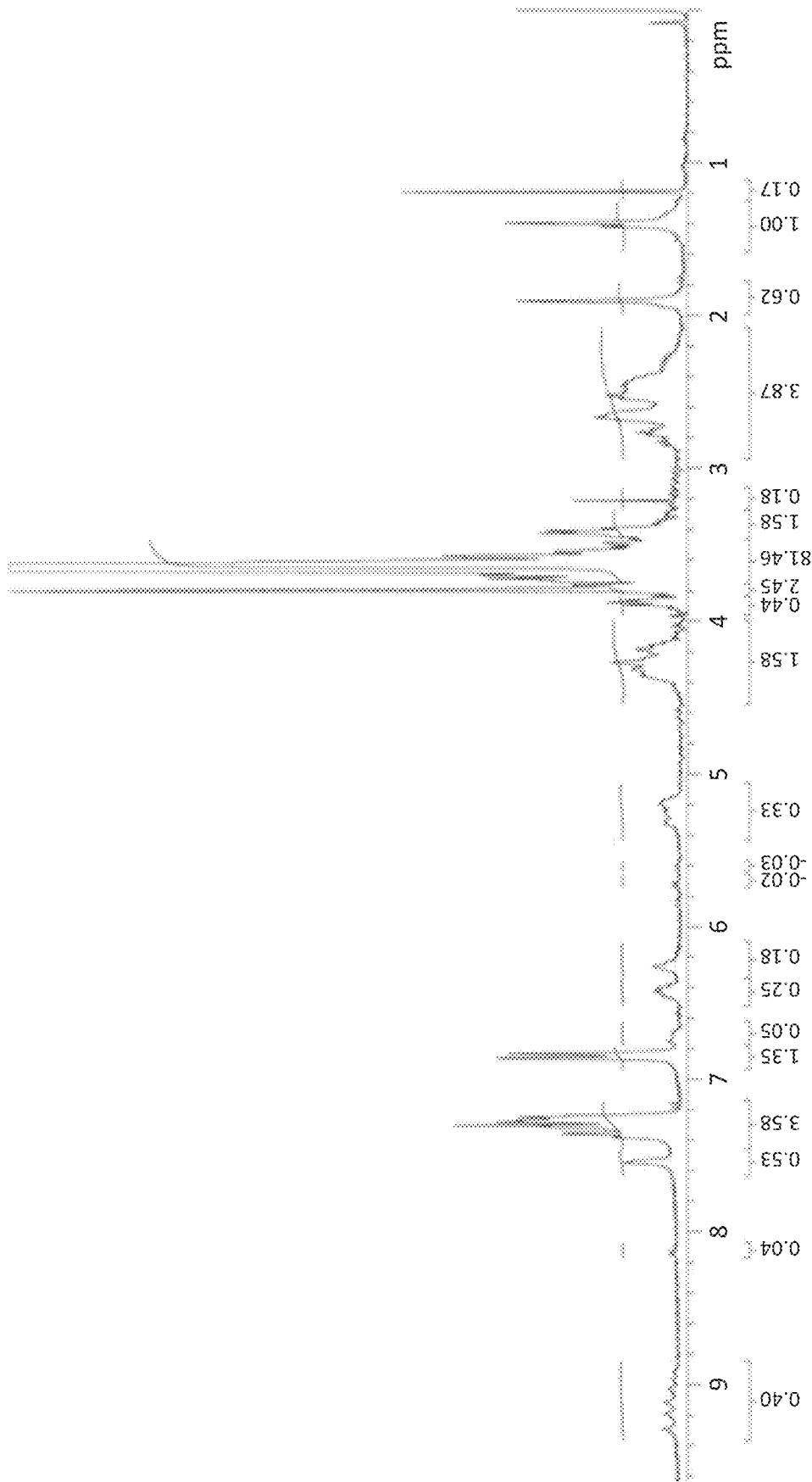
FIG. 5B is a ¹H NMR spectrum measured in CDCl₃ of a poly(NH₂-PEG$_{3.4k}$ acrylate) homopolymer-dT-dT conjugate according to an embodiment of the present application.
Figure 5C:
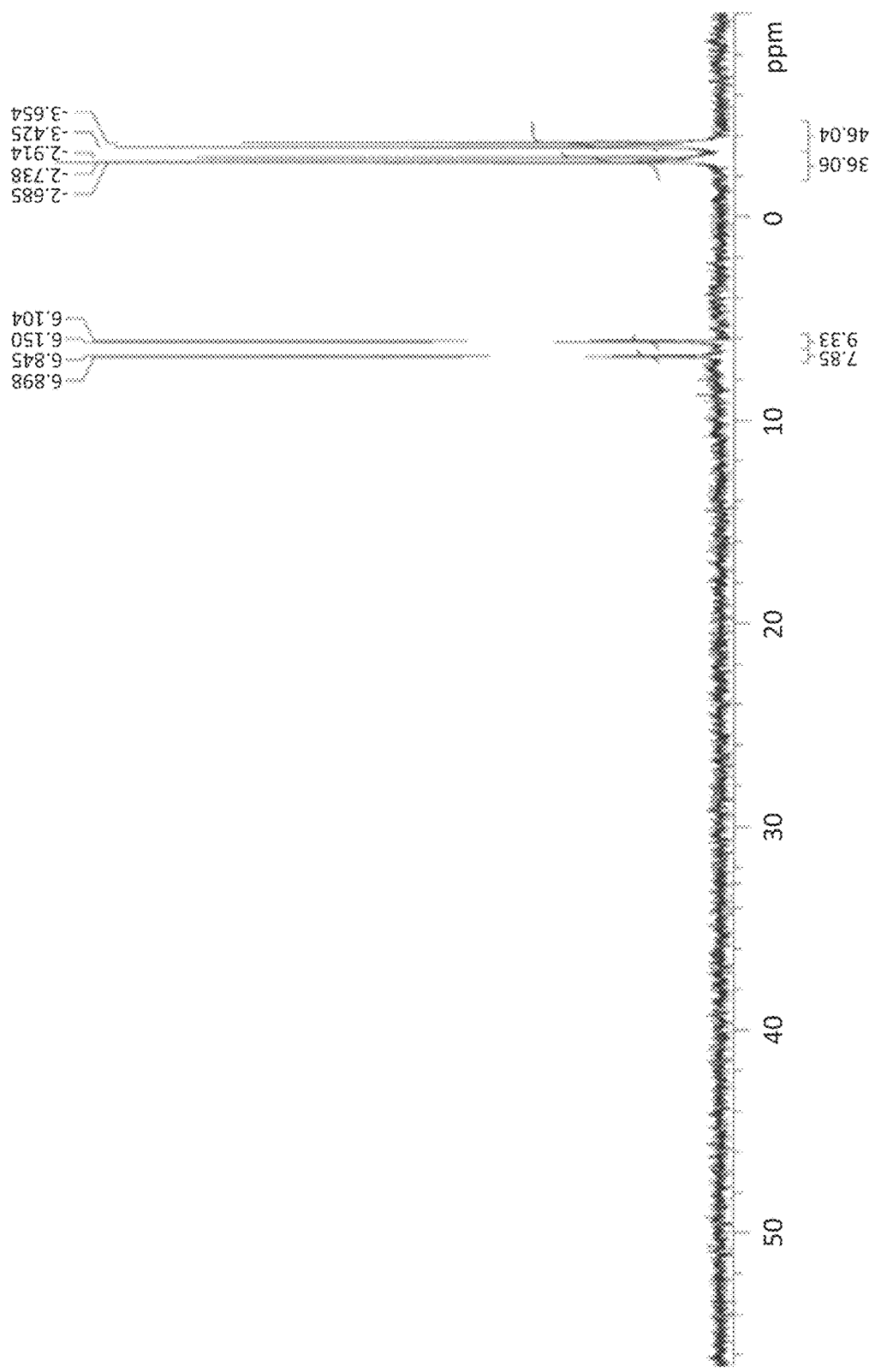
FIG. 5C is a ³¹P NMR spectrum measured in CDCl₃ of a poly(NH₂-PEG$_{3.4k}$ acrylate) homopolymer-dT-dT conjugate according to an embodiment of the present application.
Figure 5D:
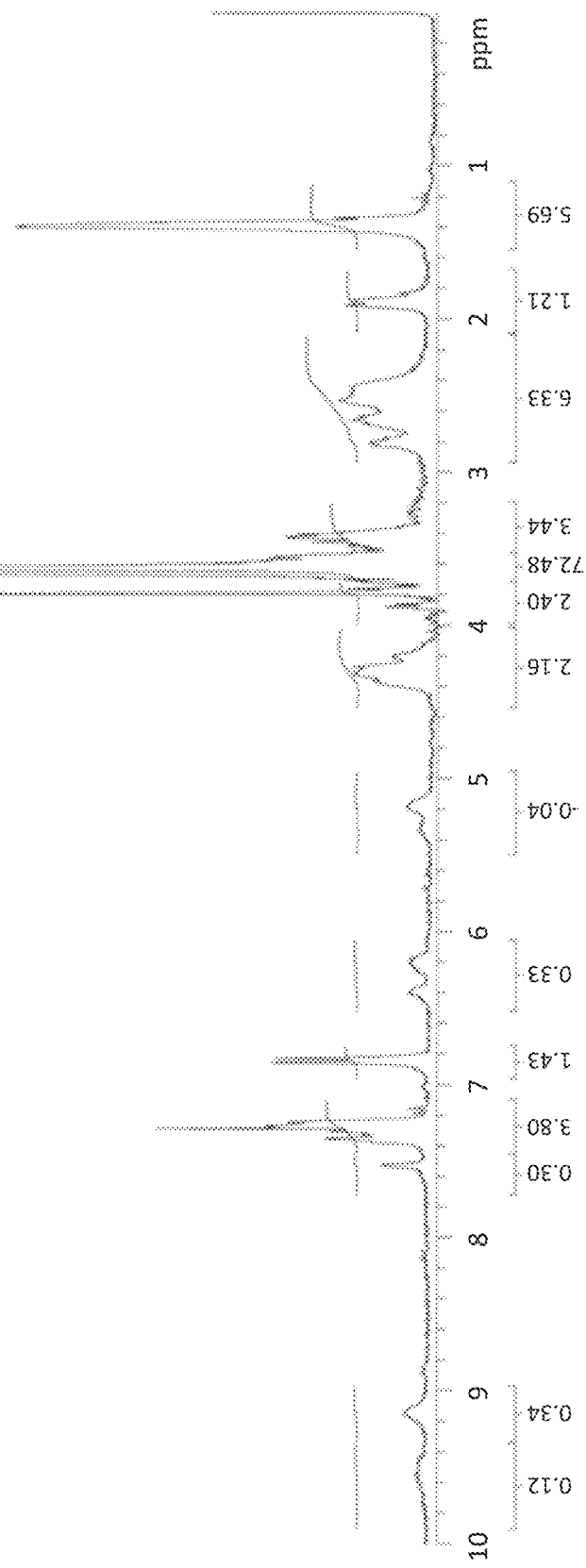
FIG. 5D is a ¹H NMR spectrum measured in CDCl₃ of a poly(NH₂-PEG$_{3.4k}$ acrylate) homopolymer-dT-dT-dT conjugate according to an embodiment of the present application.
Figure 5E:
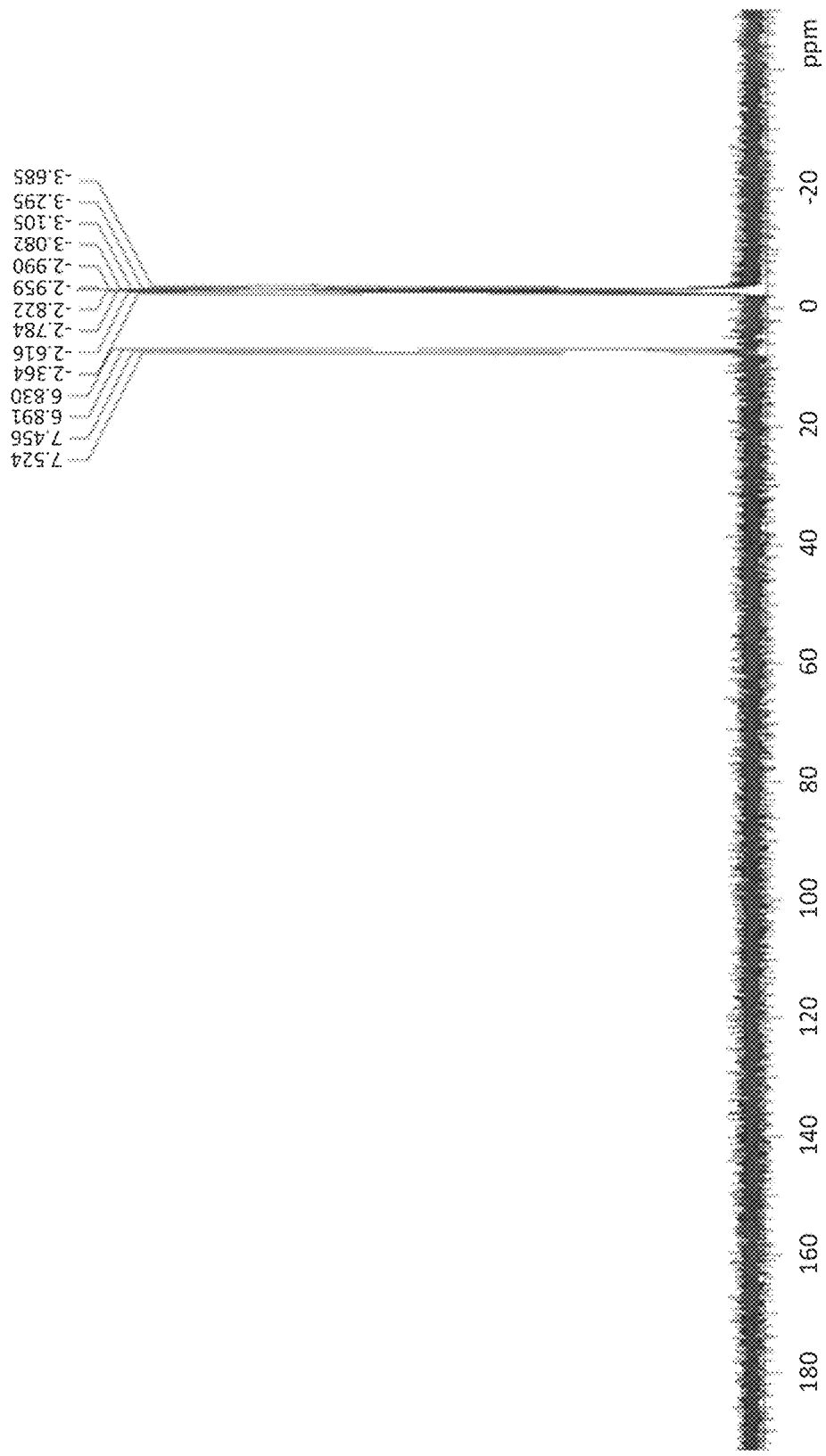
FIG. 5E is a ³¹P NMR spectrum measured in CDCl₃ of a poly(NH₂-PEG$_{3.4k}$ acrylate) homopolymer-dT-dT-dT conjugate according to an embodiment of the present application.

FIGS. 5B and 5C illustrate $^1$H and $^{31}$P NMR spectrum taken in chloroform-d1 of the DMT-dTdT conjugated poly (NH$_2$-PEG$_{3.4k}$ acrylate) homopolymer prepared in Example 10. FIGS. 5D and 5E illustrate $^1$H and $^{31}$P NMR spectrum taken in chloroform-d1 of the DMT-dTdTdT conjugated poly(NH$_2$-PEG$_{3.4k}$ acrylate) homopolymer prepared in Example 10.

Example 11. Preparation of DMT-dAdTdTdT-3'-succinate Conjugated poly(NH$_2$-PEG$_{3.4k}$ Acrylate) Homopolymer

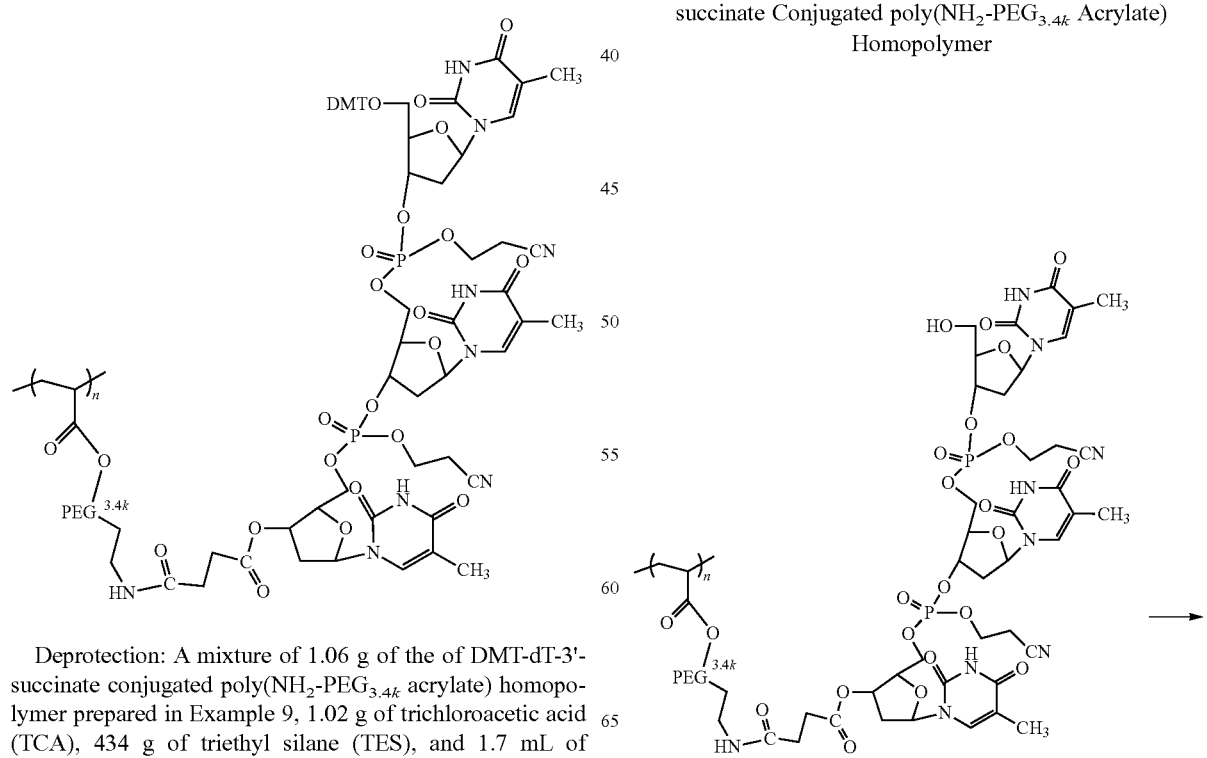

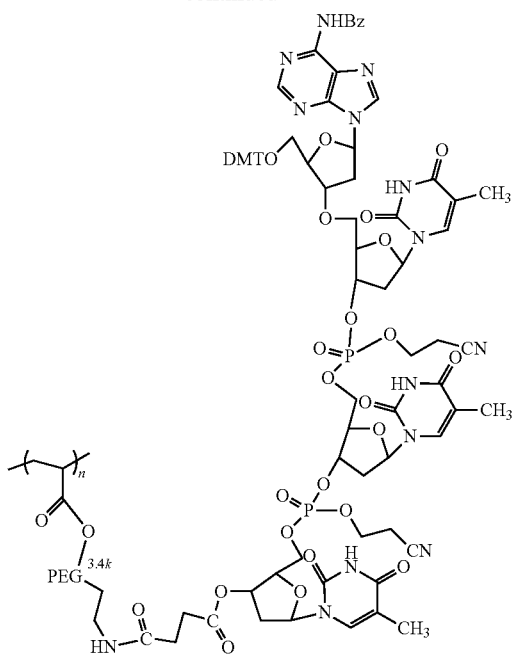

The DMT protected bioconjugate DMT-dTdTdT-3'-succinate conjugated poly(NH$_2$-PEG$_{3.4k}$ acrylate) homopolymer prepared in Example 10 was deprotected using TCA and TES as described herein to provide OH-dTdTdT-3'-succinate conjugated poly(NH$_2$-PEG$_{3.4k}$ acrylate) homopolymer. Coupling and oxidation: To 100 mg of the dTdT-3'-succinate conjugated poly(NH$_2$-PEG$_{3.4k}$ acrylate) homopolymer in a 15-mL tube was added 1.08 mL (35 mg) 0.25 M ETT solution and 58 mg DMT-dA phosphoramidite under constant stirring for around 60 minutes, and then 36 mg mCPBA was added as a powder. The mixture was further stirred for another 10 minutes. The solution was precipitated from diethyl ether to provide the DMT protected bioconjugate having one dA nucleobase and three dT nucleobases DMT-dAdTdTdT-3'-succinate conjugated poly(NH$_2$-PEG$_{3.4k}$ acrylate) homopolymer.

Figure 5F:
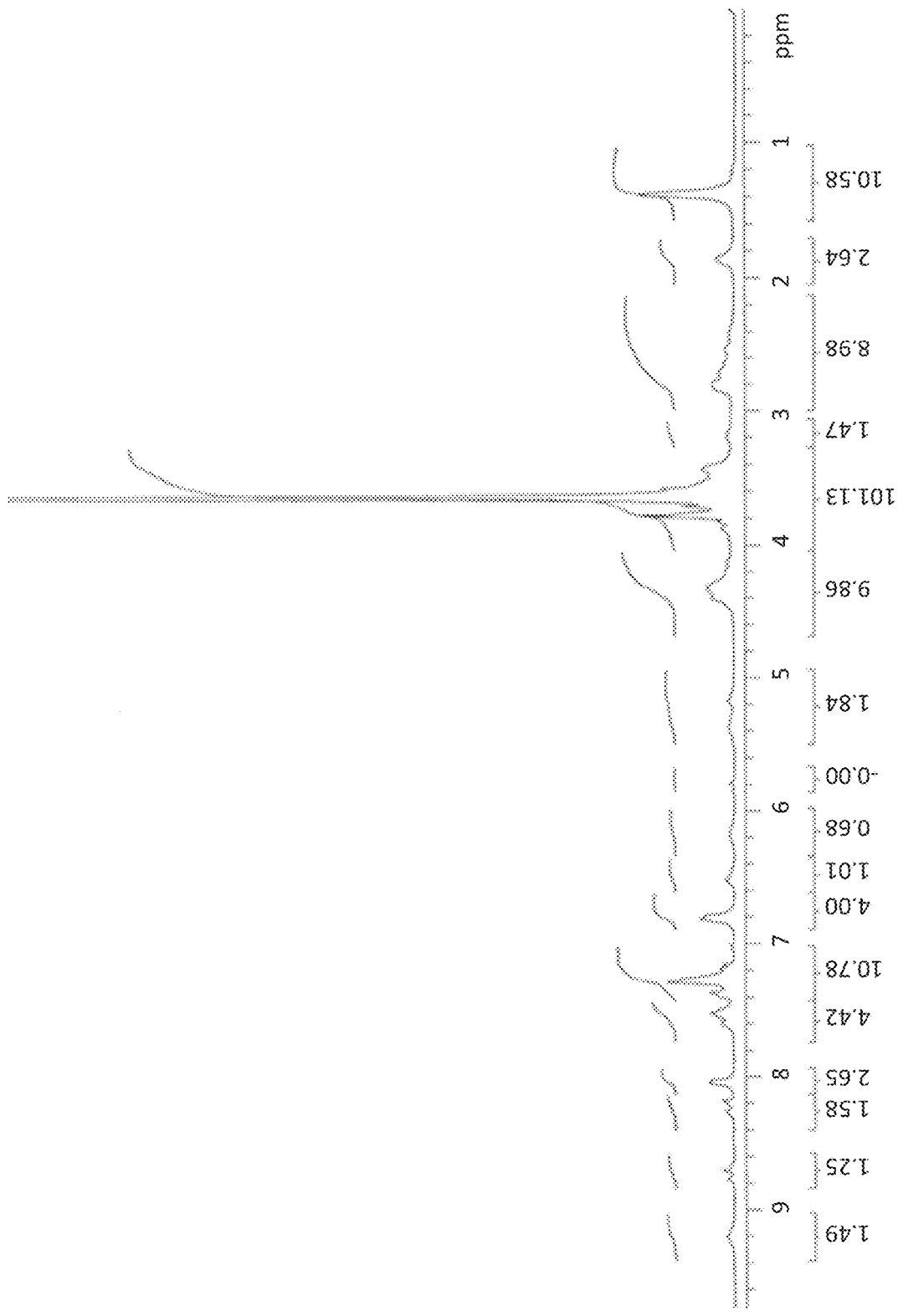
FIG. 5F is a ¹H NMR spectrum measured in CDCl₃ of a poly(NH₂-PEG$_{3.4k}$ acrylate) homopolymer-dT-dT-dT-dA conjugate according to an embodiment of the present application.
Figure 5G:
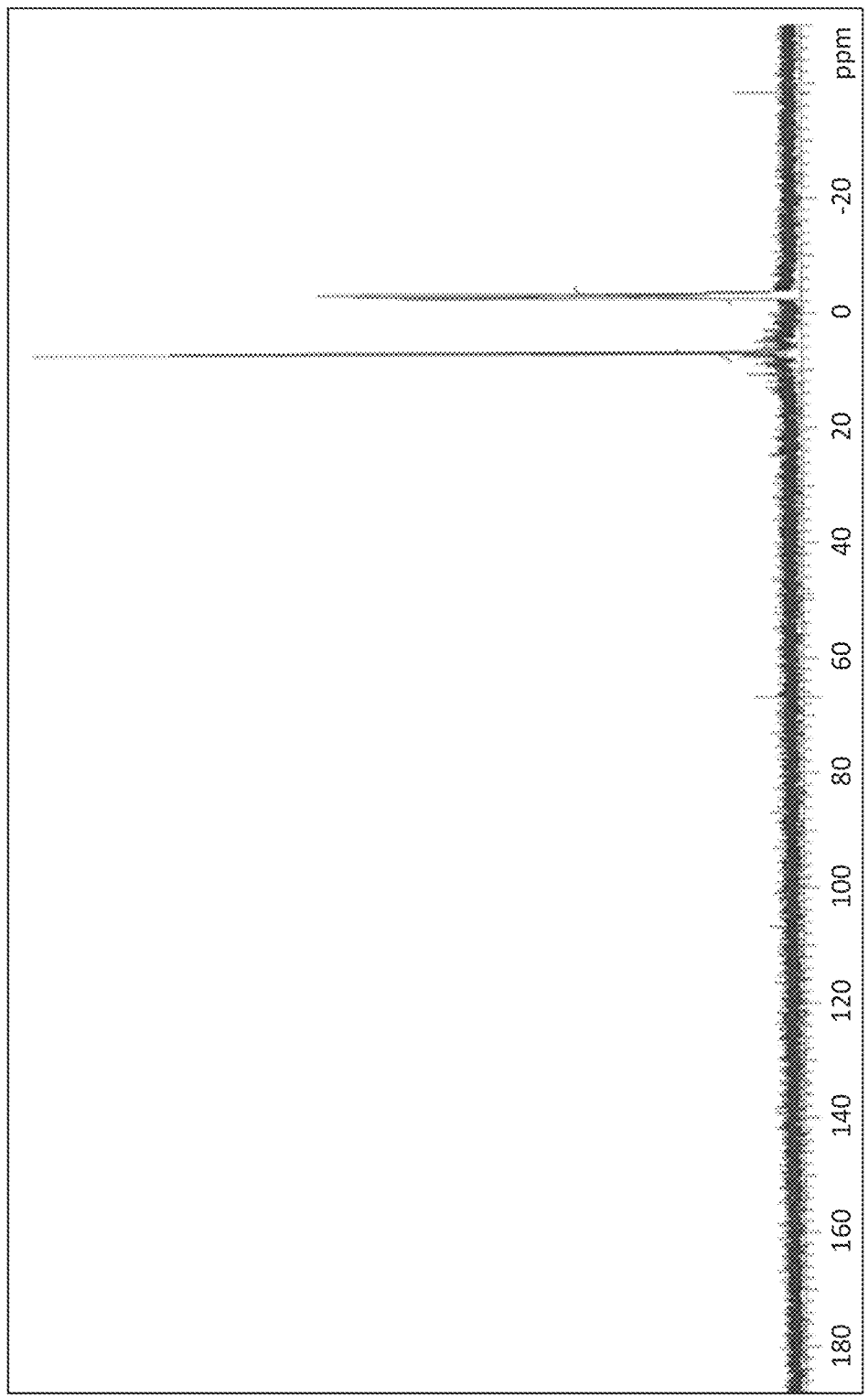
FIG. 5G is a ³¹P NMR spectrum measured in CDCl₃ of a poly(NH₂-PEG$_{3.4k}$ acrylate) homopolymer-dT-dT-dT-dA conjugate according to an embodiment of the present application.

FIGS. 5F and 5G illustrate $^1$H and $^{31}$P NMR spectrum taken in chloroform-d1 of the DMT-dAdTdTdT conjugated poly(NH$_2$-PEG$_{3.4k}$ acrylate) homopolymer prepared in Example 11.

Example 12. Preparation of poly(DMA-co-NH$_2$-PEG$_{3.4k}$ acrylate) and Conjugates Thereof

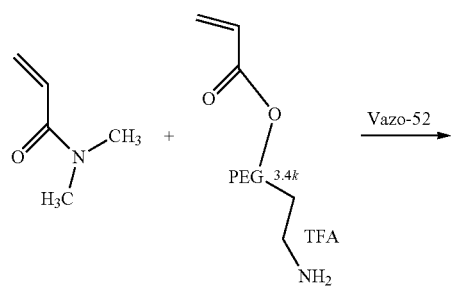

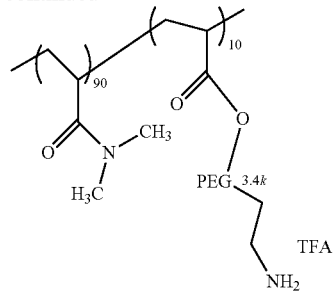

Into a 100-mL three-necked round bottom flask containing 40 mL of dry acetonitrile (ACN), 800 mg (0.235 mmol) of Acrylate-PEG-amine and 212 mg (2.139 mmol) of purified N,N-dimethylacrylamide (DMA) were dissolved. The mixture was bubbling with ultra-pure argon at 50 ml/min for 75 minutes under constant stirring. To this deoxygenated solution 96 mg of Vazo-52 in 1 mL of anhydrous ACN was injected and the polymerization was conducted at 55±2° C. for 21 hours under ultra-pure argon with flow rate of 20 mL/min. The reaction was cooled to ambient temperature and the reaction product was precipitated in diethyl ether to give 806 mg (79.6% yield) of the copolymer. The numbers 90 and 10 for th DMA repeating unit and NH$_2$-PEG$_{3.4k}$ acrylate repeating unit the copolymer refer to monomer ratio of DMA and NH$_2$-PEG$_{3.4k}$ acrylate (i.e., NH$_2$-PEG$_{3.4k}$ acrylate is about 10 mol % and DMA is about 90 mol %).

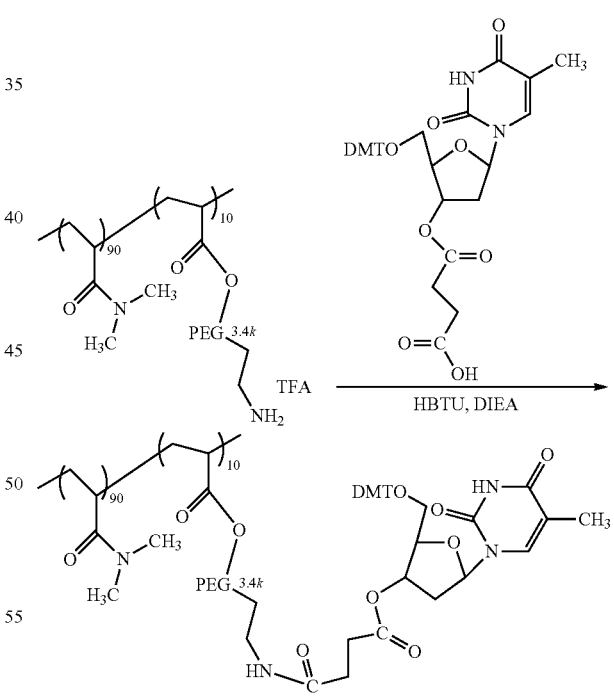

Into 4 mL acetonitrile, 773 mg poly(DMA-co-aminoPEG$_{3.4k}$ acrylate), 353 mg DMT-dT-3'-succinate TEA salt, 197 mg HBTU, and 122 mg Diisopropylethylamine were dissolved. The resulting solution was vortexed overnight at ambient temperature. The reaction product was precipitated in diethyl ether to give 704 mg (80% yield) the first dT conjugate comprising a 5'-DMT protective group. DMT loading=196 µmol/g.

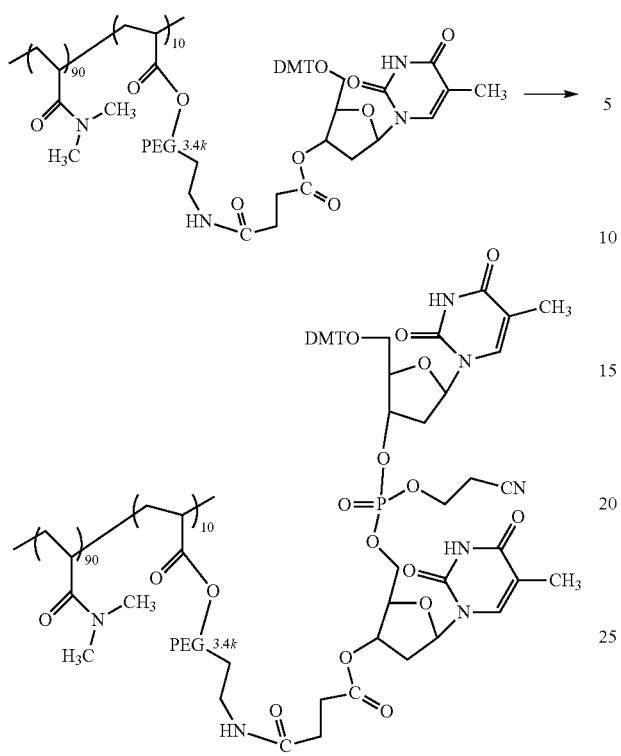

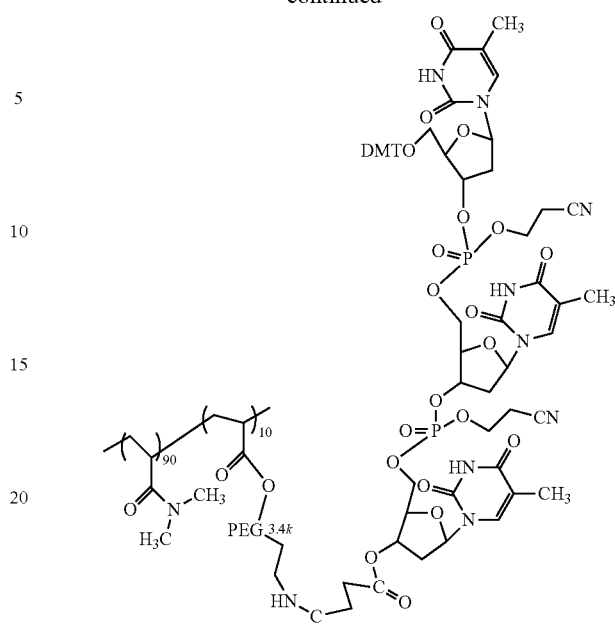

Deprotection: A mixture of 654 mg of poly(DMA-co-aminoPEG$_{3.4K}$ acrylate)-dT, 542 mg of trichloroacetic acid (TCA), 218 mg of triethyl silane (TES), and 904 µL of dichloromethane (DCM) was shaken for about 10 minutes at ambient temperature. The reaction product was then precipitated in diethyl ether to give the DMT deprotected conjugate.

Coupling and oxidation: To the above obtained dT conjugate was added 6.33 mL of 0.25 M ETT (5-(Ethylthio) tetrazole) solution (205 mg) and 342 mg of DMT-dT phosphoramidite under stirring. After 60 mins of constant stirring, 175 mg of 3-Chloroperbenzoic acid (mCPBA) was added as a powder. The mixture was further stirred for another 10 mins. The solution was precipitated by diethyl ether to give the consecutive second dT conjugate comprising a 5'-DMT protective group. DMT loading=203 µmol/g.

Deprotection: A mixture of 630 mg of poly(DMA-co-aminoPEG$_{3.4K}$ acrylate)-dT-dT, 487 mg of trichloroacetic acid (TCA), 196 mg of triethyl silane (TES), and 812 µL of dichloromethane (DCM) was shaken for about 10 minutes at ambient temperature. The reaction product was then precipitated in diethyl ether to give the DMT deprotected conjugate.

Figure 6:
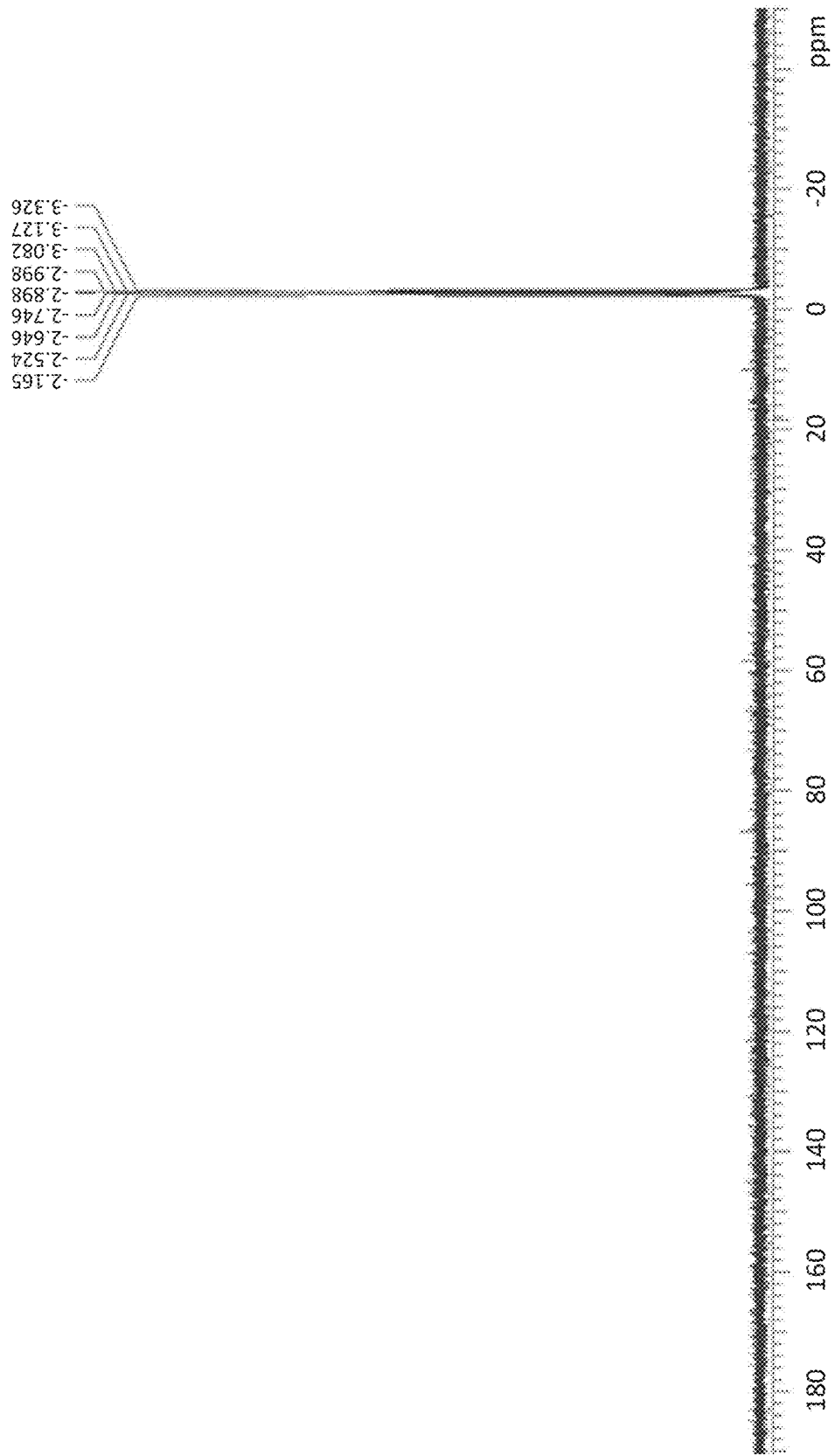
FIG. 6 is a ¹⁹P NMR spectrum of a poly(DMA-co-aminoPEG$_{3.4K}$ acrylate) copolymer-dT-dT-dT conjugate according to an embodiment of the present application.

Coupling and oxidation: To the above obtained dT conjugate was added 6.33 mL of 0.25 M ETT (5-(Ethylthio) tetrazole) solution (176 mg) and 283 mg of DMT-dT phosphoramidite under stirring. After 60 mins of constant stirring, 181 mg of 3-Chloroperbenzoic acid (mCPBA) was added as a powder. The mixture was further stirred for another 10 mins. The solution was precipitated by diethyl ether to give the consecutive third dT conjugate comprising a 5'-DMT protective group, DMT loading=185 µmol/g. FIG. 6 is a $^{19}$P-NMR of poly(DMA-co-aminoPEG$_{3.4K}$ acrylate)-dT-dT-dT.

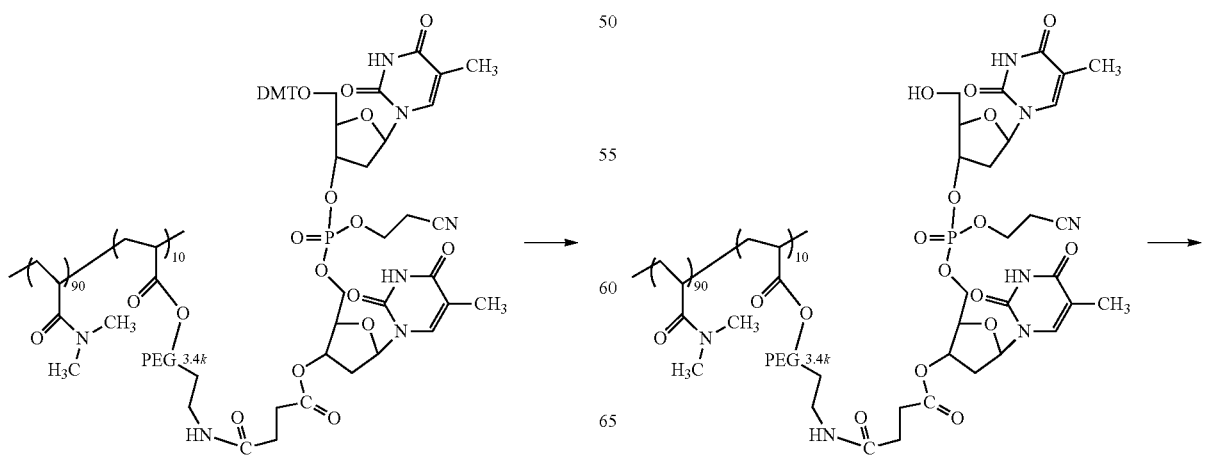

-continued

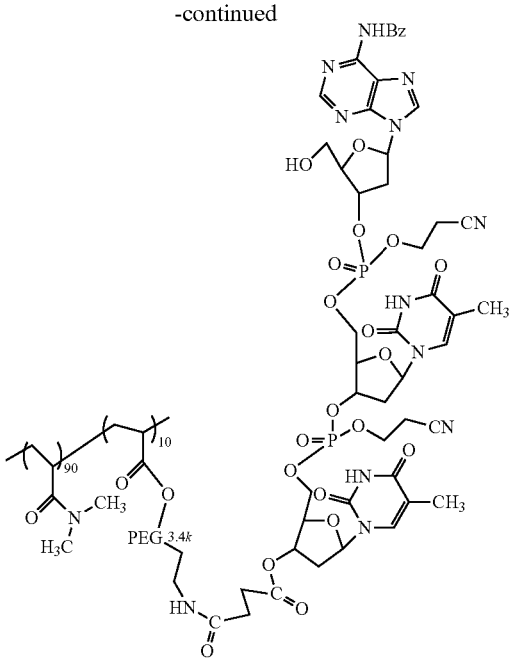

Coupling and oxidation: To 50 mg poly(DMA-co-aminoPEG$_{3.4K}$ acrylate)-dT-dT(OH) was added 0.48 mL of 0.25 M ETT (5-(Ethylthio)tetrazole) solution (13.3 mg) and 26 mg of DMT-dA phosphoramidite under stirring. After 60 mins of constant stirring, 14 mg of 3-Chloroperbenzoic acid (mCPBA) was added as a powder. The mixture was further stirred for another 10 mins. The solution was precipitated by diethyl ether to give dimethylacrylamide copolymer with the consecutive dT-dT-dA conjugate.

Deprotection: A mixture of above poly(DMA-co-aminoPEG$_{3.4K}$ acrylate)-dT-dT-dA conjugate, 354 mg of dichloroacetic acid (DCA), 115 mg of triethyl silane (TES), and 590 µL of dichloromethane (DCM) at 0° C. was shaken for about 10 minutes. The reaction product was then precipitated in diethyl ether to give the DMT deprotected conjugate.

Example 13. General Procedure for the Cleavage of Oligo Conjugated onto PVH

A mixture of 200 µL molecular biology grade water and 1.0 mg of an oligo comprising a PVH bioconjugate prepared as described in Example 5, 10, 11, 12 was vortexed for 30 second at ambient temperature to give a clear solution. An aliquot of 40 µL of this solution was added to a 2-mL microtube and 160 µL of AMA solution (30% ammonia:40% methylamine 1:1 v/v) was added. The mixture was placed in a heating block at 55° C. for 5 hours. The reaction mixture was dried under reduced pressure at 55° C. for 2 hours. The dried residue containing the cleaved oligos (e.g., T, TT, TTT, ATT or ATTT) was dissolved in 200 µL molecular biology grade water (5× dilution) for subsequent HPLC analysis.

Example 14. General Procedure for the Cleavage of Oligo Conjugated onto PVH by Ethanol Precipitation An aliquot of 50 µL of 2M sodium acetate was added to the solution of the cleaved oligo prepared in Example 13 and vortexed to mix well. Then, cold ethanol was added to this solution drop-wise until the solution turns cloudy. It was followed by adding cold ethanol with constant vortexing till the total volume reached 1 mL. The suspension was centrifuged to collect the precipitated oligo as a pellet. The pellet was dissolved in 200 µL molecular biology grade water for subsequent HPLC analysis.

Example 15. HPLC-Analysis of Oligo Cleaved from Conjugated PVH

An aliquot of 10 µL of the solution of the cleaved oligo prepared in Example 13 was used for HPLC analysis with Waters BEH C18 column (2.5 um 50*4.6 mm). Solvent A is 50 mM TEAA and solvent B is acetonitrile (ACN). The gradient used was 5-40% solvent B in 20 min, followed by 40-90% solvent B in 20 min for a total 40 min with a flow rate at 0.7 mL/min. HPLC profiles were directly compared with control samples. Control samples were a variety of oligo sequences synthesized by standard solid phase synthesis method, for example, T, TT, TTT, ATT, and ATTT, which were also cleaved and deprotected by AMA.

Figure 7A:
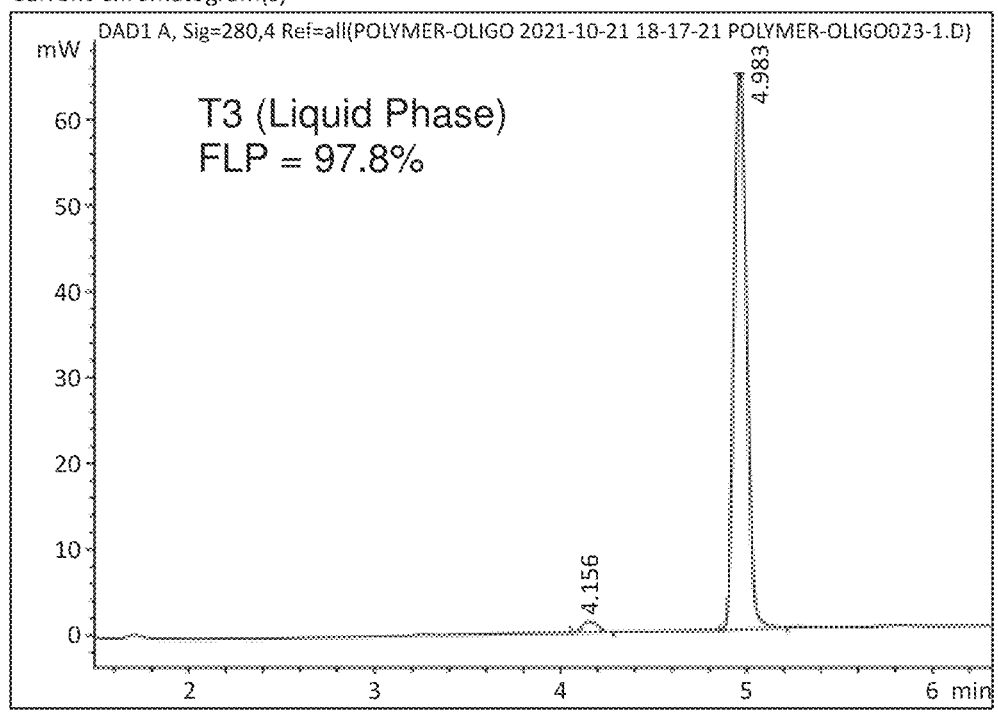
FIG. 7A is an HPLC profile of an oligonucleotide synthesized by the liquid phase method disclosed herein according to an embodiment of the present application.
Figure 7B:
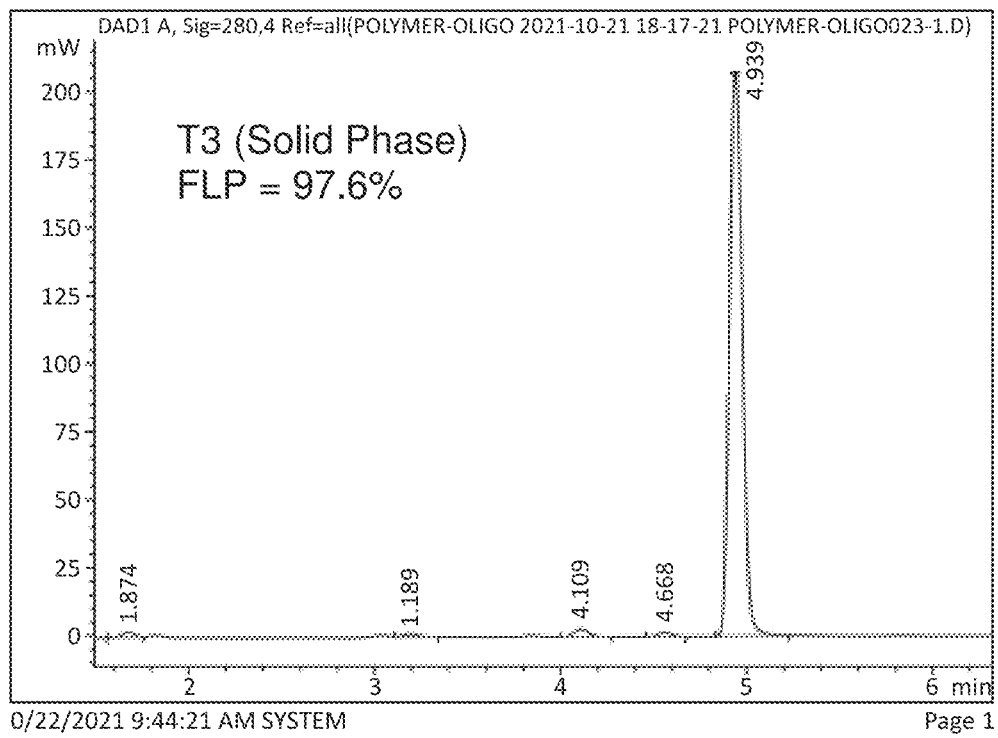
FIG. 7B is an HPLC profile of an oligonucleotide synthesized by solid phase method.

The cleaved oligos exited from the HPLC column within 12% of ACN at the first 5 minutes. The HPLC profiles of dT-dT-dT (OH) (T3) synthesized by the liquid phase method disclosed in Example 12 and T3 synthesized by solid phase method are displayed in FIGS. 7A and 7B, respectively. The retention times were the same. Full-length product (FLP) purity obtained by liquid phase synthesis is about 97.8%, which was comparable to the purity of 97.6% obtained by the solid phase synthesis. The full-length product dT-dT-dA (OH) obtained from Example 12 had about 78% purity. The results confirmed the feasibility of the liquid phase oligo synthesis disclosed herein.

While the present application has been described with reference to the specific embodiments thereof, it should be understood by those skilled in the art that various changes may be made and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

Column 61, Lines 50-57 (approx.), Claim 4, delete " " and insert -- --. 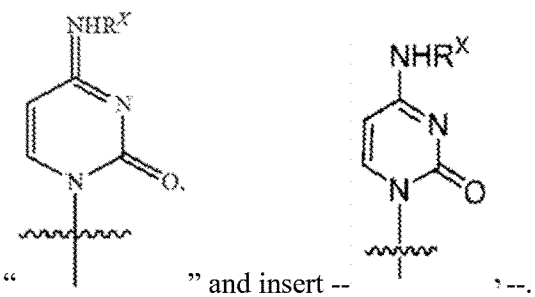

What is claimed is:

1. A method for preparing an oligonucleotide by liquid phase oligonucleotide synthesis, comprising:

dissolving a polyvalent hub (PVH) comprising a copolymer comprising one or more acrylamide or acrylate repeating units, and one or more repeating units of Formula (I) in a first solvent to form a reaction matrix,

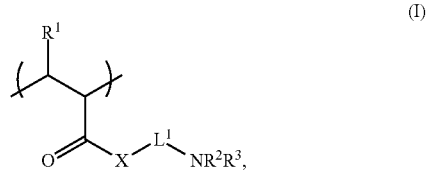

(I)

wherein:
X is NR$^4$, S, or O;
each of R$^1$, R$^2$, R$^3$ and R$^4$ is independently H or C$_1$-C$_6$ alkyl; and
L$^1$ is a heteroalkylene linker comprising one or more oxygen atoms; and reacting the PVH with one or more nucleoside analogs to form a first bioconjugate comprising a structure of Formula (III):

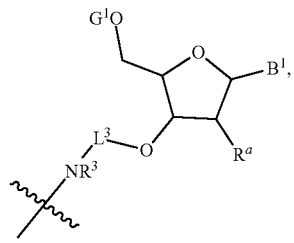

(III)

wherein
B¹ is a nitrogenous base;
G¹ is a 5' hydroxyl blocking group;
$R^a$ is —H, —OH, halogen, —O—($C_1$-$C_6$ alkyl), —O—($C_1$-$C_6$ haloalkyl), or —OY, where Y is a 2' hydroxyl protecting group; and
L³ is a cleavable heteroalkylene linker where one or more carbon atoms is replaced by O, S, N, C(=O) or C(=S).

2. The method of claim 1, wherein the structure of Formula (III) is also represented by Formula (IIIa):

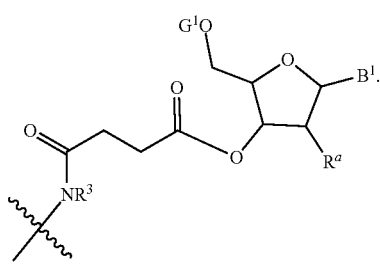

(IIIa)

3. The method of claim 1, wherein B¹ is independently optionally protected adenine, optionally protected deaza adenine, optionally protected cytosine, optionally protected guanine, optionally protected deaza guanine, optionally protected thymine or optionally protected uracil.

4. The method of claim 3, wherein B¹ is,

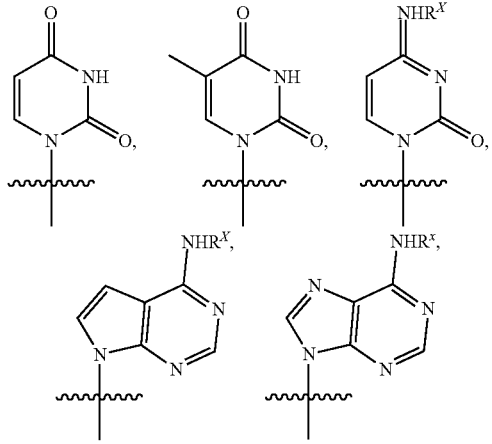

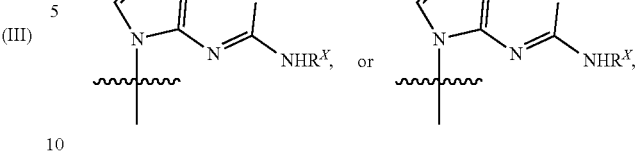

wherein $R^x$ is hydrogen, unsubstituted or substituted $C_1$-$C_6$ alkyl, or an amino protecting group, or the hydrogen in —NHR$^x$ is absent and $R^x$ is a divalent amino protecting group.

5. The method of claim 1, wherein G¹ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

6. The method of claim 1, wherein the PVH has an average molecular weight from about 5 kDa to about 1000 kDa; or from about 10 kDa to about 100 kDa.

7. The method of claim 1, further comprising:
removing the 5' hydroxyl blocking group (G¹) to form a 5' unblocked first bioconjugate; and
isolating the 5' unblocked first bioconjugate.

8. The method of claim 7, wherein the isolation of the 5' unblocked first bioconjugate is achieved by precipitation, dialysis or filtration with a membrane comprising a regenerated cellulose.

9. The method of claim 7, further comprising:
(a) reacting the 5' unblocked first bioconjugate with one or more nucleoside phosphoramidite analogs in a second solvent to form a second bioconjugate comprising the structure of Formula (IV):

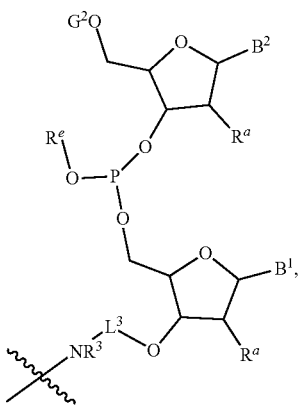

(IV)

wherein
G² is a 5' hydroxyl blocking group;
B² is a nitrogenous base; and
$R^e$ is a phosphite protecting group;
(b) oxidizing the phosphite moiety in Formula (IV);
(c) removing the 5' blocking group G² to form a 5' unblocked second bioconjugate comprising the structure of Formula (IV'):

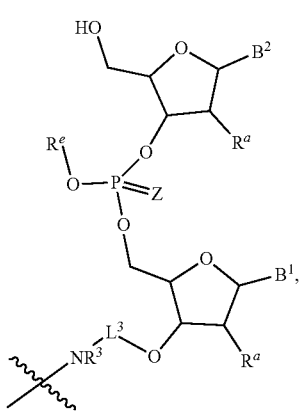

(IV')

wherein

Z is O or S; and (d) isolating the 5' unblocked second bioconjugate.

10. The method of claim 9, wherein the structure of Formula (IV) is also represented by (IVa) and the Formula (IV') is also represented by Formula (IV'a):

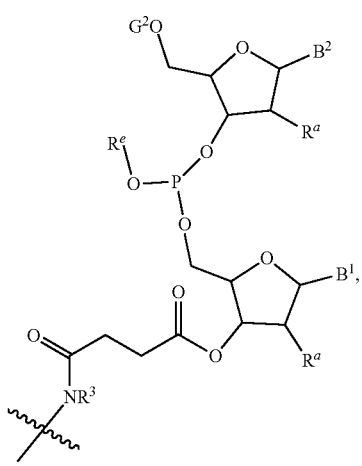

(IVa)

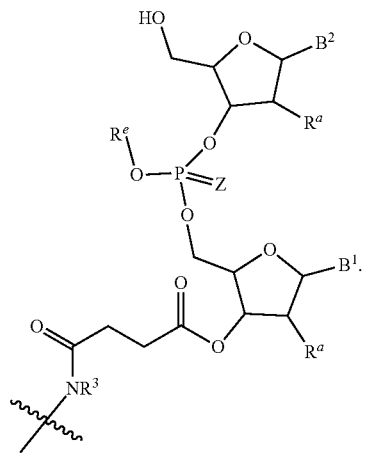

(IV'a)

11. The method of claim 9, further comprising blocking unreacted 5' hydroxyl group in the 5' unblocked first bioconjugate prior to step (b).

12. The method of claim 9, wherein $B^2$ is independently optionally protected adenine, optionally protected deaza adenine, optionally protected cytosine, optionally protected guanine, optionally protected deaza guanine, optionally protected thymine, or optionally protected uracil.

13. The method of claim 9, wherein $G^2$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

14. The method of claim 9, wherein said isolation of the 5' unblocked second bioconjugate is achieved by precipitation, filtration, or dialysis using a regenerated cellulose membrane having a molecular weight cutoff (MWCO) from about 5 kDa to about 50 kDa.

15. The method of claim 9, wherein steps (a)-(d) are repeated multiple cycles until one or more desired length of oligonucleotides have been synthesized.

16. The method of claim 15, further comprising removing the oligonucleotides from the PVH.

17. The method of claim 9, wherein each of the first solvent and the second solvent comprise one or more non-protic polar solvents, wherein the one or more non-protic polar solvents comprise acetonitrile, tetrahydrofuran (THF), dimethylformamide (DMF), dimethyl sulfoxide (DMSO), dichloromethane (DCM), or sulfolane, or combinations thereof.

18. An oligonucleotide prepared by the method according to claim 15.

19. The method of claim 1, wherein $R^1$ is H.

20. The method of claim 1, wherein the repeating unit of Formula (I) is also represented by Formula (Ia):

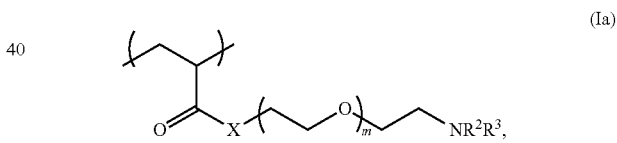

(Ia)

wherein m is an integer of 1 to 1000; or wherein the repeating unit of Formula (I) is also represented by Formula (Ib):

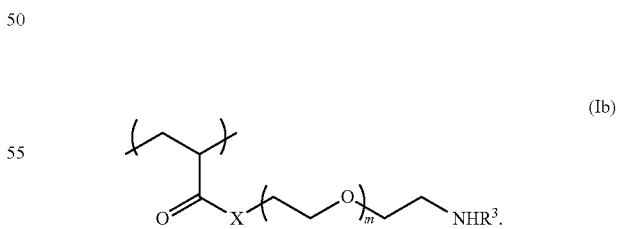

(Ib)

21. The method of claim 20, wherein X is NH and m is 2.

22. The method of claim 20, wherein X is O, and m is from about 10 to 200.

23. The method of claim 1, wherein the copolymer comprises the one or more acrylamide or acrylate repeating unit of Formula (II):

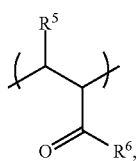
(II)

wherein
- $R^5$ is H or $C_1$-$C_6$ alkyl;
- $R^6$ is —$NR^7R^8$ or —O-$L^2$-$R^9$;
- each of $R^7$, $R^8$ and $R^9$ is independently optionally substituted $C_1$-$C_6$ alkyl, optionally substituted phenyl, or $R^7$ and $R^8$ together with the nitrogen atom to which they are attached form an optionally substituted 5 or 6 membered heterocyclyl; and
- $L^2$ is a heteroalkylene linker comprising one or more oxygen atoms.

24. The method of claim 23, wherein $R^5$ is H.

25. The method of claim 23, wherein $R^6$ is —$NR^7R^8$, and the repeating unit of Formula (II) is also represented by Formula (IIa):

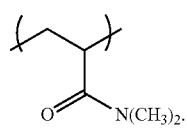
(IIa)

26. The method of claim 23, wherein $R^6$ is —O-$L^2$-$R^9$, and the repeating unit of Formula (II) is also represented by Formula (IIb):

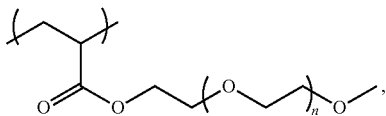
(IIb)

wherein n is an integer of 1 to 1000.

27. The method of claim 1, wherein the copolymer comprises:

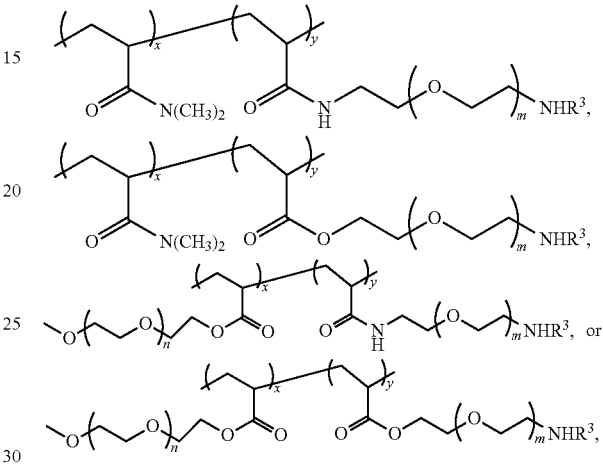

wherein each of m and n is independently an integer from about 2 to 200; and each of x and y is independently an integer from 1 to 50,000.

28. A first bioconjugate comprising a structure of Formula (III) prepared by the method according to claim 1.

* * * * *

UNITED STATES PATENT AND TRADEMARK OFFICE
CERTIFICATE OF CORRECTION

PATENT NO. : 11,851,454 B2
APPLICATION NO. : 18/146279
DATED : December 26, 2023
INVENTOR(S) : Gaomai Yang et al.

Page 1 of 3

It is certified that error appears in the above-identified patent and that said Letters Patent is hereby corrected as shown below:

In the Specification

Column 2, Lines 12-19 (approx.), delete " 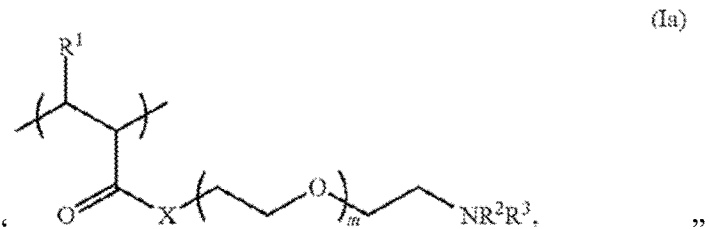 "
and insert -- 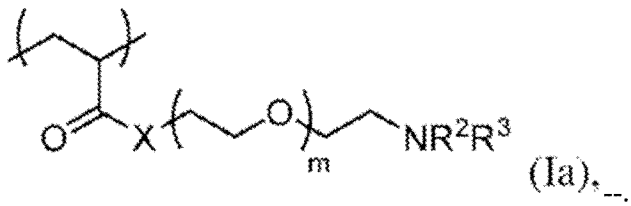 --.

Column 2, Lines 38-45 (approx.), delete "  " and insert
-- 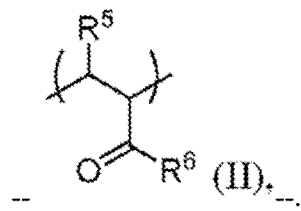 --.

Signed and Sealed this
Seventh Day of May, 2024

Katherine Kelly Vidal
*Director of the United States Patent and Trademark Office*

CERTIFICATE OF CORRECTION (continued)
U.S. Pat. No. 11,851,454 B2

Column 2, Lines 60-65 (approx.), delete "  " and insert --  --.

Column 20, Line 13 (approx.), delete "p-toluensulfonic" and insert -- p-toluenesulfonic --.

Column 25, Line 53 (approx.), delete "yl" and insert -- $y^1$ --.

Column 29, Lines 45-61 (approx.), delete " 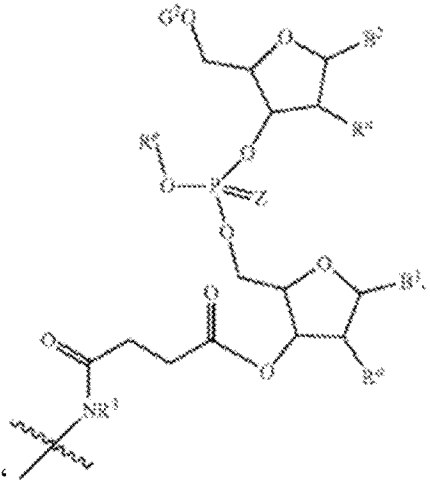 " and insert -- 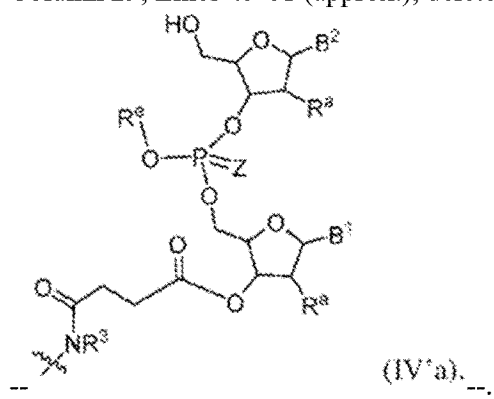 --.

CERTIFICATE OF CORRECTION (continued)
U.S. Pat. No. 11,851,454 B2

Column 33, Lines 55-63 (approx.), delete " " and insert -- --. 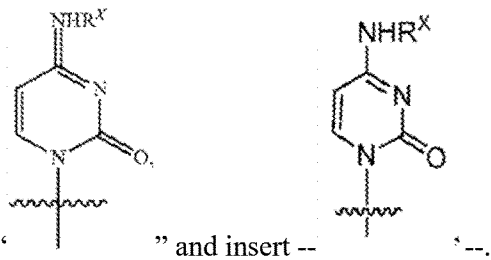

Column 43, Line 37 (approx.), delete "is quantitatively are" and insert -- is quantitatively --.

Column 53, Line 63 (approx.), delete "of the of" and insert -- of the --.

In the Claims